US006143872A

United States Patent [19]
Barbour et al.

[11] Patent Number: 6,143,872
[45] Date of Patent: Nov. 7, 2000

[54] BORRELIA BURDORFERI OSP A AND B PROTEINS AND IMMUNOGENIC PEPTIDES

[75] Inventors: Alan George Barbour, San Antonio, Tex.; Sven Bergstrom; Lennart Hansson, both of Umea, Sweden

[73] Assignee: Symbicom Aktiebolag, S-Umea, Sweden

[21] Appl. No.: 08/479,017

[22] Filed: Jun. 6, 1995

Related U.S. Application Data

[62] Continuation-in-part of application No. 08/079,601, Jun. 22, 1993, Pat. No. 5,523,089, which is a continuation of application No. 07/924,798, Aug. 6, 1992, abandoned, which is a continuation of application No. 07/422,881, Oct. 18, 1989, abandoned, and a division of application No. 08/137,175, filed as application No. PCT/US92/08972, Oct. 22, 1992, Pat. No. 5,777,095, which is a continuation-in-part of application No. 07/779,185, Oct. 22, 1991, abandoned.

[30] Foreign Application Priority Data

Oct. 24, 1988 [DK] Denmark ................................. 5902/88

[51] Int. Cl.$^7$ ............................. C07K 1/00; C07K 16/00; A61K 39/00; A61K 39/02
[52] U.S. Cl. .......................... 530/359; 530/350; 530/806; 424/185.1; 424/190.1; 424/193.1; 424/197.11; 424/201.1; 424/202.1; 424/203.1; 514/2
[58] Field of Search .................................... 530/350, 359, 530/806; 424/185.1, 190.1, 193.1, 197.11, 201.1, 202.1, 203.1; 514/2

[56] References Cited

U.S. PATENT DOCUMENTS

| | | | |
|---|---|---|---|
| 4,888,276 | 12/1989 | Shelbourne | 435/7 |
| 5,178,859 | 1/1993 | Simon et al. | . |
| 5,523,089 | 6/1996 | Bergstrom et al. | 424/262.1 |
| 5,582,990 | 12/1996 | Bergstrom et al. | . |
| 5,688,512 | 11/1997 | Bergstrom et al. | 424/234.1 |

FOREIGN PATENT DOCUMENTS

| | | |
|---|---|---|
| 0418827 | 3/1991 | European Pat. Off. . |
| WO91/09952 | of 0000 | WIPO . |
| WO91/13096 | of 0000 | WIPO . |
| WO93/04175 | of 0000 | WIPO . |
| WO-A-900441 | 5/1990 | WIPO . |
| WO 91/09870 | 7/1991 | WIPO . |
| WO-A-9200055 | 1/1992 | WIPO . |

OTHER PUBLICATIONS

Calderwood et al, "Iron regulation of shiga like toxin expression in Escherichia coli is mediated by the fur locus", J. Bacteriol. 169(10):4759–4764, Oct. 1987.

Vlasuk et al, "Effects of the complete removal of basic amino acid residues from the signal peptide on secretion of lipoprotein in Escherichia coli", J. Biol. Chem. 258(11):7141–7148, Jun. 1983.

Jonsson et al, "Heterogeneity of outer membrane proteins in Borrelia burgdorferi: comparison of Osp operons of three isolates of different geographic origins", Inf. Immun. 60(5):1845–1853, May 1992.

Bockenstedt et al, "Inability of truncated recombinant Osp A proteins to elicit protective immunity to Borrelia burgdorferi in mice", J. Immunol. 151:900–906, Jul. 1993.

Guy et al., "Detection of Borrelia burgdorferi in patients with Lyme diseae by the polymerase chain reaction.", J Clin Pathol. 1991 Jul.; 44(7): 610–611.

Gyllensten, U. in "PCR technology—principles and application for DNA amplification". pp. 45–60, 1989.

Nucleotide sequence search printout (EMBL, GenBank, N–GeneSeq.) (Nov. 9, 1992).

Fellinger et al., "Sequence of the complete osp operon encoding two major outer membrane proteins of European *Borrelia burgdorferi* isolate (B29)",Gene, 120, 127–128, 1992.

Rosa et al., "Molecular analysis of the major outer surface protein locus from a divergent *Borrelia burgdorferi* isolate from Europe", Curr. Communications in Cell and Mol. Biol. 5 (Schutzer ed.) Cold Spring Harbor Press, Cold Spring Habor, New York, Date Not Available.

Zumstein et al., "Genetic polymorphism of the gene encoding the outer surface protein A (OspA) of *Borrelia burgdorferi*", Med. Microbiol. Immunol., 181, 57–70, 1992.

Asbrink, E. & A Hovmark. 1985. Successful cultivation of spirochetes from skin lesions of patients with erythema chronicum mirgran Afzelius and acrodermatitis chronica atrophican. Acta. Path. Microbiol. Immunol. Scand. Sect. B, 93: 161–163.

Barbour et al., The Yale Journal of Biology and Med. 57: 581–586, 1984.

Barbour, A.G. 1984. Isolation and cultivation of Lyme disease spirochetes. Yale J. Bil. Med. 57: 71–75.

Barbour, A.G. 1984. Immunochemical analyis of Lyme disease spirochetes. Yale J. Biol. Med. 57: 581–586.

Barbour, A.G. 1988. Plasmid Analysis of *Borrelia burgdorferi*, the Lyme Disease Agent. Journal of Clinical Microbiology 26: 475–478.

Barbour, A.G. 1989. Antigenic variation in relapsing fever Borrelia species: genetic aspects. In Berg, D.E. & Howe, M.M. (eds): Mobile DNA, Washington, D.C. American Society for Microbiology, pp. 783–789.

Barbour, A.G. & C.F. Garon. 1987. Linear plasmids of the bacterium *Borrelia burgdorferi* have covalently closed ends. Science 237: 409–411.

(List continued on next page.)

*Primary Examiner*—Jeffrey Fredman
*Attorney, Agent, or Firm*—Frommer Lawrence & Haug LLP; William S. Frommer; Thomas J. Kowalski

[57] ABSTRACT

Disclosed and claimed are isolated polypeptides consisting of amino acid sequences derived form ospA and/or ospB of various *B. burgdorferi* or portions thereof and methods of making and using the same.

124 Claims, 22 Drawing Sheets

OTHER PUBLICATIONS

Barbour, A.G., R.A. Heiland & T.R. Howe. 1985. Heterogeneity of major proteins in Lyme disease borreliae: a molecular analysis of North American and European isolates. J. Infect. Dis. 153: 478–484.

Barbour, A.G. & M.E. Schrumpf. 1986. Polymorphism of major surface proteins of *Borrelia burgdorferi*. Zentralbl. Bakteriol. Parasitenkd. Infektionskr. Hyg. Abt. 1 Orig. Reihe A. 263: 83–91.

Barbour, A.G., S.L. Tessier & S.F. Hayes. 1984. Variation in a major surface protein of Lyme disease spirochetes. Infect. Immun. 45: 94–100.

Barbour, A.G., Sl.L. Tessier & W.J. Todd. 1983. Lyme disease spirochetes and Ixodes ticks share a common surface antigenic determinant defined by a monoclonal antibody. Infect. Immun. 41: 795–804.

Barbour, A.G., N. Burman, C.J. Carter, T. Kitten & S. Bergström. 1991. Variable antigen genes of the relapsing fever agent *Borrelia hermsii* are activated by promoter addition. Mol. Microbiol. 5: 489–493.

Barbour, A.G., C.J. Carter, N. Burman, C.S. Freitag, C.F. Garon & S. Bergström. 1991. Tandem insertion sequence-–like elements define the expression site for variable antigen genes of *Borrelia hermsii*. Infect. Immun. 59: 390–397.

Barstad et al Journal of Exp. Med. 161:1302–1314, 1986.

Bergström, S., K. Robbins, M. Koomey & J. Swanson. 1986. Piliation control mechanism in *Neisseria gonorrhoeae*. Proc. Natl. Acad. Sci. USA 83: 479–486.

Bergström, S., V.G. Bundoc & A.G. Barbour. 1989. Molecular analysis of linear plasmid–encoded major surface proteins, OspA and OspB, of the Lyme disease spirochete *Borrelia burgdorferi*. Mol. Microbiol. 3: 479–486.

Brandt, M.E., B.S. Riley, J.D. Radolf & M.V Norgard. 1990. Immunogenic integral membrane proteins of *Borrelia burgdorferi* are lipoproteins. Infect. Immun. 58: 983–991.

Bundoc, V.G. & A.G. Barbour. 1989. Clonal polymorphism of outer membrane protein OspB of *Borrelia burgdorferi*. Infect. Immun. 57: 2733–2741.

Burman, N., S. Bergström, B.I. Restrepo & A.G. Barbour. 1990. The variable antigens Vmp7 and Vmp21 of the relapsing fever bacterium *Borrelia hermsii* are structurally analogous to the VSG proteins of the African trypanosome. Mol. Microbiol. 4: 1715–1726.

Coleman et al. Journal of Infect. Dis. 155: 756–765, 1987.

Coleman et al. Zbl. Bakt. Hyg. A 263: 123–126, 1986.

Craft, J.E., D.K. Fischer, G.T. Shimamoto & A.C. Steere. 1986. Antigens of *Borrelia burgdorferi* recognized during Lyme disease. Appearance of a new IgM response and expansion of the IgG response late in illness. J. Clin. Invest. 78: 934–939.

Cunningham et al., Annals of the New York Academy of Sciences 539: 371–378, 1988.

Fikrig, E., S.W. Barthold, F.S. Kantor & R.A Flavell. 1990. Protection of mice against the Lyme Disease agent by immunizing with recombinant OspA. Science 250: 553–556.

Fikrig et al., Impact & Immunity 60: 773–777. 1992.

Harr, R., P. Fällman, M. Häggström, L. Wahlström & P. Gustafsson. 1986. Geneus, a computer system for DNA and protein sequence analysis containing an information retrieval system for the EMBL data library. Nucl. Acids. Res. 11: 273–284.

Hoheisel, J. & F.M. Pohl. 1986. Simplified preparation of unidirectional deletion clones. Nucl. Acids Res. 14. 3605.

Howe, T.R., F.W. LeQuier & A.G. Barbour. 1986. Organization of genes encoding two outer membrane proteins of the Lyme disease agent with a single transcriptional unit. Infect. Immun. 54. 207–212.

Howe, T.R., L.W. Mayer & A.G. Barbour. 1985. A single recombinant plasmid expressing two major outer surface proteins of the Lyme disease spirochete. Science 227: 645–646.

Huynh, T.U., R.A. Young & R.W. Davis. 1985. Construction and screening cDNA libraries in Agt10 and Agt11. In DNA Cloning, vol. 1, ed. Glover, D.M. IRL Press Limited, Oxford, England, pp. 56–110.

Inouye, M. & S. Halegoua. 1980. Secretion and membrane localization of proteins in *Escherichia coli*. Crit. Rev. Biochem. 7: 339–371.

Jameson, B.A. & H. Wolf. 1988. The antigenic index: a novel algorithm for predicting antigenic determinants. Comput. Appl. Biosci. 4: 181–186.

Kyruchechnikov, V.N., E. I. Korenberg, S.V. Scherbakov, Yu.V. Yovalevsky & M.L. Levin. 1988. Identification of Borrelia isolated in the USSR form *Ixodes persulcatus* schulze ticks. J. Microbiol. Epidemiol. Immunobiol. 12: 41–44.

Loenen, W.A.M. & W.J. Brammer. 1980. A bacteriophage lambda vector for cloning large DNA fragments made with several restriction enzymes. Gene 20: 249–259.

Luft et al., Annals of the New York Academy of Sciences 559: 398–399. Date Not Available.

Malloy, D.C. , R.K. Nauman & H. Paxton. 1990. Detection of *Borrelia burgdorferi* using the polymerase chain reaction. J. Clin. Microbiol. 28: 1089–1093.

Maniatis, T.E., E.F. Fritsch & J. Sambrook. 1982. Molecular cloning: A laboratory manual. Cold Spring Harbor, New York, Cold Spring Harbor, N.Y. USA Laboratory Press.

Marx et al., Annals of the New York Acad. of Sciences 539:398–399, 1988.

Meier, J.T., M.I. Simon & A.G. Barbour. 1985. Antigenic variation is associated with DNA rearrangements in a relapsing fever borrelia. Cell 41: 403–409.

Nielsen, S.L., K.K.Y. Young & A.G. Barbour. 1990. Detection of *Borrelia burgdorferi* DNA by the polymerase chain reaction. Mol. Cell. Probes. 4: 73–79.

Plasterk, R.H.A., M.I. Simon & A.G. Barbour. 1985. Transportation of structural genes to an expression sequence on a linear plasmid causes antigenic variation in the bacterium *Borrelia hermsii*. Nature 318: 257–263.

Postic, D., C. Edlinger, C. Richaud, F. Grimont, Y. Durfresne, P. Perolat, G. Baranton & P.A.D. Grimont. 1990. Two genomic species in *Borrelia burgdorferi*. Res. Microbiol. 141: 465–475.

Rosa, P.A. & T.G. Schwan. 1989. A specific and sensitive assay for the Lyme disease spirochete *Borrelia burgdorferi* using the polymerase chain reaction. J. Infect. Dis. 160: 1018–1029.

Rosa, P.A., D. Hogan & T.G. Schwan. 1991. Polymerase chain reaction analyses identify two distinct classes of *Borrelia burgdorferi*. J. Clin. Microbiol. 29: 524–532.

Rosenberg, M. & O. Court. 1979. Regulatory sequences involved in the promotion and termination of transcription. Ann. Rev. Genet. 13: 256–275.

Sanger, F., S. Nicklen & A.R. Coulson. 1977. DNA sequencing with chain–terminating inhibitors. Proc. Natl. Acad. Sci. USA 74: 5463–5467.

Saunders, S.E. & J.F. burke. 1990. Rapid isolation of miniprep. DNA for double strand sequencing. Nucl. Acids. Res. 18: 4948.

Schaible, U.E., M.D. Kramer, K. Eichman, M. Modolell, C. Museteanu & M.M. Simon. 1990. Monoclonal antibodies specific for the outer surface protein A (OspA) of *Borrelia burgdorferi* prevent Lyme borreliosis in severe combined immunodeficiency (scid) mice. Proc. Natl. Acad. Sci. USA 87: 3768–3772.

Schubach, W.H., S. Mudri, R.J. Dattwyler & B.J. Luft. 1991. Mapping antibody–binding domains of the major outer surface membrane protein (OspA) of *Borrelia burgdorferi*. Infect Immun. 59: 1991–1915.

Schwan, T.G. & W. Burgdorfer. 1987. Antigenic changes of *Borrelia burgdorferi* as a result of in vitro cultivation. J. Infect. Dis. 156: 852–853.

Schwan, T.G., W. Burgdorfer & C.F. Garon. 1988. Changes in infectivity and plasmid profile of the Lyme disease spirochete, *Borrelia burgdorferi*, as a result of in vitro cultivation. Infect. Immun. 56: 1831–1836.

Stiernstedt, G. 1985. Tick–borne Borrelia infection in Sweden, Scand. J. Infect. Dis. Suppl. 45: 1–70.

Wallich, R., U.E. Schaible, M.M. Simon, A. Heiberger & M.D. Kramer. 1989. Cloning and sequencing of the gene encoding the outer surface protein A (OspA) of a European *Borrelia burgdorferi* isolate. Nucl. Acids. Res. 17: 8864.

Williams, J.G. & P.J. Mason. 1985. Hybridization in the analysis of RNA. In Nucleic acid hybridization. Hames, B.D. & S.J. Higgins (eds), Oxford: IRL Press, pp. 139–160.

Wilske, B., V. Preac–Mursic, G. Schierz, R. Kuhbeck, A.G. Barbour & M. Kramer. 1988. Antigenic variability of *Borrelia burgdorferi*. Ann. N.Y. Acad. Sci. 539: 126–143.

Wilske et al., Research Microbiol. 143: 583–596, 1992.

van Gabain, A., J.G. Belasco, J.L. Schotttel, A.C.Y. Chang & S.N. Cohen. 1983. Decay of mRNA in *Escherichia coli*: investigation of the fate of specific segments of transripts. Proc. Natl. Acad. Sci. USA 80: 653–657.

von Heijne, G. 1983. Patterns of amino acids near signal sequence cleavage sites. Eur. J. Biochem. 133: 17–21.

Wu, H.C. & M. Tokunaga. 1986. Biogenesis of lipoproteins in bacteria. In Current Topics in Microbiology and Immunology, vol. 125, pp. 127–157.

Arnhem, N. & Levenson, C.H. 36, Oct. 1, 1990 C&EN special report. Polymerase Chain Reaction.

Sambrook, J. et al. Molecular Cloning, a laboratory manual. Date Not Available.

Old, R.W. and Primrose, S.B. Principles of Gene Manipulation, a textbook. Date Not Available.

Gray, M.R., Colot, H.V., Guarente, L. and Rosbach, M. 1982. Open reading frame cloning: identification, cloning and expression of open reading from DNA. Proc. Natl. Acad. Sci. USA 79: 6598–6602.

Löwenadler, B., Nilsson, B. , Abrahmsén, L., Moks, T., Ljungquist, L., Holmgren, E., Paleus, S., Josephson, S., Philipson, L. and Uhlén, M. 1986. Production of specific antibodies against protein A fusions. EMBO J. 5: 2393–2398.

Löwenadler, B., Jansson, B., Paleus, S., Holmgren, E., Nilsson, B., Moks, T., Palm, G., Josephson, S., Philipson, L. and Uhlén, M. 1987. A gene fusion system for generating antibodies against short peptides. Gene 58: 87–97.

Löwenadler, B., Svennerholm, A.–M., Gidlund, M., Holmgren, E., Krook, K., Svanholm, C. Ulff, S. and Josephson, S. 1990. Enhanced immunogenicity of recombinant peptide fusions containing multiple copies of a heterologous T helper epitope. Eur. J. Immunol. 20: 1541–1545.

Löwenadler, B., Lake, M., Elmblad, A., Holmgren, E., Holmgren, J., Karlström, A. and Svennerholm, A.–M. 1991. A recombinant *Escherichia coli* heat–stable enterotoxin (STa) fusion protein eliciting anti–Sta neutralizing antibodies. FEMS Microbiol. Lett. 82: 271–278.

Nakamura, K., Masui, Y. and Inouye, M. 1982. Use of a lac promoter–operator fragment as a transcriptional control switch for expression of the constitutive 1pp gene in *Escherichia coli*. J. Mol. Appl. Gen. 1: 289–299.

Smith, D.B. and Johnson, K.S. 1988. Single–step purification of polypeptides expressed in *Escherichia coli* as fusions with glutathione S–transferase. Gene 67: 31–40.

Yansura, D.G. 1990. Expression as trpe fusion. In Methods in Enzymology. Ed. Goeddel, D.V. vol. 185: 161–166.

Hanahan, D. (1983) J. Mol. Biol. 166:557.

von Heijne, G. The structure of signal peptides from bacterial lipoproteins. Protein Engineering vol. 2, No. 7 pp. 531–534, 1989.

Nakamura, K., Inouye, M. DNA sequence of the gene for the outer membrane lipoprotein of *E. coli*: an extremely AT–rich promoter. Cell 1979; 18:1109–17.

Bergström, Sven and Maria Jonsson, "Molecular characteristics and genetic organization of the osp–operon from different *Borrelia burgdorferi* isolates", abstract from ASM Meeting 5–7 May 1991.

Jonsson, Maria and Sven Bergström, "Molecular characteristics and genetic organization of the osp–operon from different European *Borrelia burgdorferi* strains", abstract from international conference on Lyme borreliosis in 1990.

Debue et al., Res. in Microbiol., 142(5), 565–572, 1991.

Dunn et al., Protein expression and purification, 1, 159–168, 1990.

Persing et al., J. Clin. Microbiol., 28(3), 566–572, 1990.

Mw B31 ACAI lp90

30.0-

Mw B31 ACAI lp90

46.0-

30.0-

```
B31   AAACTTAA TTGA AGTTATTATCATTTTA TTTTTTT
N40   -------- ---- --------------- -------
ZS7   -------- ---- --------------- -------
ACAI  -T--C---T--A- -A-------------T-------
Ip90  -T-TA--- --T-G-A---------------- -------
```

```
                 -35                          -10
B31   TCAATTTTCTATTTGTTATTTGTTAATCTTATAATATAA
N40   ---------------------------------------
ZS7   ---------------------------------------
ACAI  -T-----------------------A--G-------C-----
Ip90  -T-----G-----------------------G-------C-----
```

```
             +1                240
B31   TTATACTTGTATTAAGTTATATTAATAT      AAAAG
N40   ---------------------------      -----
ZS7   ---------------------------      -----
ACAI  ---------------------------AATATA-----
Ip90  -----T---------------------AATATA-----
```

```
      RBS            ospA
B31   GAGAATATATTATGAAAAAATATTTATTGGGAATAGGTC
N40   --------------------------------------
ZS7   --------------------------------------
ACAI  --------------------------------------
Ip90  --------------------------------------
```

FIG. 3A-1

```
                           80
B31   TAATATTAGCC TTAATAGCAT GTAAGCAAAATGTTAGC
N40   ------------------------------------------
ZS7   ------------------------------------------
ACAI  ---------------------C--------------------
Ip90  ----------A-------------------------------

120
B31   AGCCTTGACGAGAAAAACAGCGTTTCAGTAGATTTGCCT
N40   ---------------------------------------
ZS7   ---------------------------------------
ACAI  --------T--A---------C-----------------
Ip90  --------T--A-----T------------------A---

160
B31   GGTGAAATGAAAGTTCTTGTAAGCAAAGAAAAAAACAA
N40   -----------C--------------------------
ZS7   -----------C--------------------------
ACAI  -----G---------------------T----------G----
Ip90  ----G----C-----------------T----------G----

200
B31   AGACGGCAAGTACGATCTAATTGCAACAGTAGACAAGCT
N40   ---------------------------------------
ZS7   ---------------------------------------
ACAI  -------T------AG-----AG---------------A-
Ip90  ---T--T--A---AG------G-----------------
```

FIG. 3A-2

```
                            240
B31   TGAGCTTAAAGGAACTTCTGATAAAACAATGGATCTG
N40   ------------------------------------
ZS7   ------------------------------------
ACAI  -----A-----------------G-------T----
Ip90  ----------------------------C--T----

280
B31   GAGTACTTGAAGGCGTAAAAGCTGACAAAAGTAAAGTA
N40   --------------------------------------
ZS7   --------------------------------------
ACAI  ----G--------TAC------A---------------C-
Ip90  --ACA--------T-A------A---------------C-

320
B31   AAATTAACAATTTCTGACGATCTAGGTCAAACCACACTT
N40   ---------------------------------------
ZS7   ---------------------------------------
ACAI  ----------------G--------------A--A---------T-C
Ip90  ----------------G----G---------A--A---------T--

360
B31   GAAGTTTTCAAAGAAGATGGCAAAACACTAGTATCAAAA
N40   ---------------------------------------
ZS7   ---------------------------------------
ACAI  ----C--------------------------T----G----G-
Ip90  ---A-C-------------------------T-----------
```

FIG. 3A-3

```
                                          400
B31  AAAGTAACTTCCAAAGACAAGTCATCAACAGAAGAAAA
N40  ---------------------------------------
ZS7  ---------------------------------------
ACAI -------G---T--------AA------------T----T
Ip90 -------CCTT----------------------------

440
B31  ATTCAATGAAAAAGGTGAAGTATCTGAAAAAATAATAAC
N40  ---------------------------------------
ZS7  ---------------------------------------
ACAIG---------------T-G----C-----CC--G--
Ip90------C-C---G--------C------------C----GT

480
B31  AAGAGCAGACGGAACCAGACTTGAATACACAGGAATTAA
N40  --------------------------------A------
ZS7  --------------------------------A------
ACAI------A-A-T--------A---------T----A---G--
Ip90------A-T-------------------AC--A--

520
B31  AAGCGATGGATCTGGAAAAGCTAAAGAGGTTTTAAAAGG
N40  ---------------------------------------
ZS7  -------------------------------------A-
ACAI---------A-C----------------A---------AA
Ip90------AA-A-C------------------A----------A
```

FIG. 3A-4

```
B31   CTATGTTCTTGAAGGAACTCTAACTGCTGA      560
                                         AAAAA
N40   -----------------------------      -----
ZS7   -------------T---------------      -----
ACAI  --T-AC-------AAG--G--AA------      T---G
Ip90  --T--C--------------G--------CGGC  ----
```

```
                                         600
B31   CAACATTGGTGGTTAAAGAAGGAACTGTTACTTTAAGCA
N40   ---------------------------------------
ZS7   ---------------------------------------
ACAI  T-------AA--A----------C-------------T-
Ip90  ------AAAA----C-----C--T---GT----------
```

```
                                         640
B31   AAAATATTTCAAAATCTGGGGAAGTTTCAGTTGAACTTA
N40   ---------------------------------------
ZS7   ---------------------------------------
ACAI  -GG-A---G----------A-----AA------CT----
Ip90  --C-C--------C-----A---A-AA--------G---
```

```
                                         680
B31   ATGACACTGACAGTAGTGCTGCTACTAAAAAAACTGCAGC
N40   ----------------------------------------
ZS7   ----------------------------------------
ACAI  ---------A---C--C-CAG----------------GC--
Ip90  -----T------C--C-CAG-----------------G-A-
```

FIG. 3A-5

```
B31   TTGGAATTCAGGCACTTCAACTTTAACAATTACTGTA
N40   ------------------------------------
ZS7   ------------------------------------
ACAI  A---G------AAA------T-------------G---T
Ip90  A---G------AAG------C-------------G---T

720
B31   AACAGTAAAAAAACTAAAGACCTTGTGTT TACAAAAGAA
N40   ---------------------------- -----------
ZS7   ---------------------------- -----------
ACAI  -----C-------------C-C-A---- ----T---C--
Ip90  --T--CCG-------C----A-------A-- C---------

760
B31   AACACAATTACAGTACAACAATACGACTCAAATGGCACC
N40   ---------------------------------------
ZS7   ---------------------------------------
ACAI  G-------A--T-------A----------CGCA--T---
Ip90  G-------A----------A-----------GCA------

800
B31   AAATTAGAGGGGTCAGCAGTTGAAATTACAAAACTTGAT
N40   ---------------------------------------
ZS7   ---------------------------------------
ACAI  --T-----A--CA-------C--------A--C-------
Ip90  --TC----A--CAA------C-----------CG---A-A
```

FIG. 3A-6

```
                840                        *** RBS
B31   GAAATTAAAAACGCTTT        AAAATAAGGAG
N40   ----------------         -------
ZS7   ----------------         -------
ACAI  ---C------------GAAAT    -----------
Ip90  ---C-----G-T-----        ------G----
```

FIG. 3A-7

```
         ospB              880
B31  AATTTATGA     GATTATTAATAGGATTTGCTTTAGCG
ACAI ---------AACA--AT---C---T---------G-TA
Ip90 -G-------AAAA--AT---C--------------TA 920
B31  TTAGCTTTAATAGGATGTGCACAAAAAGGTGCTGAGTC
ACAI --------------CG---T-T---------A-----C-
Ip90 --------------C------G------------G-----C-

960
B31      AATTGGTTCTCAAAAAGAAAATGATCTAAACCTTG
ACAI AAA--G-AC---A---G-CC-T-------A-G-AA--A
Ip90     ----C-C--------A-G--G---

1000
B31  AAGACTCTAGTAAAAAATCACATCAAAACGCTAAACAA
ACAI T-A----  --   -C--TA---CAA--G--T-----A--
Ip90 ------TA-AA---G-TCA-A-AG-CG--T-----A--

1040
B31  GACCTTCCTGCGGTGACAGAAG    ACTCAGTGTCTTTG
ACAI --T---A---TTT-AG------AAA----T--AC--C-A
Ip90 --T-------TT---A-------    --A-G---AAG--A

1080
B31  TTTAATGGTAATAAAATTTTTGTAAGCAAAGAAAAAAA
ACAI --------C-----------C-----------------
Ip90 ------AAC---G-------CA-C--------------
```

FIG. 3B-1

```
                                                            1120
B31  TAGCTCCGGCAAATATGATTTAAGAGCAACAATTGATCA
ACA1 -TCTG-T--T--------G-------------G-----AC
Ip90 -GAAGA--AT--------A-------T---T-G--G--CA--

1160
B31  GGTTGAACTTAAAGGAACTTCCGATAAAAACAATGGTTC
ACA1 -------G---------GGT---T--C--G--T-----A--
IP90 -------G----------CCT---T--G--G--T-C----G-

1200
B31  TGGAACCCTTGAAGGTTCAAAGCCTGACAAGAGTAAAGTA
ACA1 ---C-AG---------A---AG----------C--------
Ip90 ----GAG----------T---AG--------A--C-------

1240
B31  AAATTAACAGTTTCTGCTGATTTAAACACAGTAACCTTAG
ACA1 GC-A-G---A--G---AC---C----T---A----TG---
Ip90 -C-A-G TTG-------AC---C----T---A----TA---

1280
B31  AAGCATTTGATGCCAGCAACCAAAAAATTTCAAGTAAAGT
ACA1 --A---A-------A-----TA-------C-GG---G----
Ip90 --A---A----C-A-------A-------------CC----

1320
B31  TACTAAAAAACAGGGGTCAATAACAGAGGAAACTCTCAAA
ACA1 -GT----------A------G---T-A-A---T--TA----
Ip90 GG------------A---C--------A-----TA----
```

FIG. 3B-2

```
B31   GCTAATAAATTAGACTCAAAGAAATTAACAAGATCAAACG
ACAI  -- --- -- -- -- -- -- -- - - A- - -A -- -- - - -GA - -- - -
Ip 90 A --- G -- -- -- -AG-G--- - - -- --A-- --- --- -- ---TA

B31   GAACTACACTTGAATACTCACAAATAACAGATGCTGACAA
ACAI  A- - --- - -- -- -- - --- T -- -G --- -G -- -- --T--AG - --
Ip 90 AT- - -- - -A ---- --- TA - -G --- -G -- -- -C--- -- --

B31   TGCTACAAAAGCAGTAGAAACTCTAAAAAATAGCATTAAG
ACAI  - - A -- -- - -- -- -- -- -- -- --- --- -- --G -T- -- -- A
Ip 90 --- -T-- --- -- --- G- - -- -- --- --- -- --G -T--C - CC

B31   CTTGAAGGAAGTCTTGTAGTCGGAAAAACAACAGTGGAAA
ACAI  -- A -- -- - -- --- --- T-GT - -- - -- -- --C --AA - -T
Ip 90 - -- --- --- -- -- -- -- ----GT - -- - -- -- - -CT- AAC - -

B31   TTAAAGAAGGTACTGTTACTCTAAAAAGAGAAATTGAAAA
ACAI  - A- C -- - -- -- --- A ---- AT-- -C --- --- - --A- --C -
Ip 90 -A- --- -G - -C --- - --- - T-- -- -- A --- - --T- --- -

B31   AGATGGAAAAGTAAAAGTCTTTTTGAA
ACAI  - -- --- - -- -- -- -- A ---AC --A --
Ip 90 - -C --- - C --- -- --C --- ---- AG -
```

FIG. 3B-3

```
                    1560
B31  TGACACTGCA    GGTTCTAACAAAA
ACAI ---T---A--TCT---AG--CT----
Ip90 --------AGTA--G---CT----

1600
B31  AAACAGGTAAATGGGAAGACAGTACTAGCACTTTAACA
ACAI ------CA-C----A-C--A-C-----A---A------
Ip90 -----C-GT----A-C--T-C-T-------C------

1640
B31  ATTAGTGCTGACAGCAAAAAAACTAAAGATTTGGTGTT
ACAI ---------------T-----------------T-----
Ip90 G----------AC----------------------C-----

1680
B31  CTTAACAGATGGTACAATTACAGTACAACAATACAACA
ACAI ---------------C-----------GC---TG---
Ip90 ------C-----A--------------A-T--T----

1720
B31  CAGCTG GAACCAGCCTAGAAGGATCAGCAAGTGAAATT
ACAI ----A--T--T-AA--T--G--CAACT----------
Ip90 A---A--C--T-CA--T-----TAA-----C--------

1750         ***
B31  AAAAATCTTTCAGAGCTTAAAAACGCTTTAAAATAATA
ACAI ---G------G---CA------GCT------------C-
Ip90 ---G------GA--CA------GCA------------
```

FIG. 3B-4

```
B31    TATAAGTAAACCCCCTACA  AGGCATCAGCTAGTGTA
ACAI  --A---------AT-------TC---TAATA-CTT----
Ip90  -G---A------AT---G--  -A----T---C-A-- C

B31    TA TACACAAGTAGCG TCCTGA  ACGGAA CCT TTCCCGT
ACAI  --CA--TT--AA-TT-AAT-T-T-TTTTT-AA--TGTTA
Ip90  -GCA--CT--AA-TT-AAT-T-T-TTTTT-AA--TGTTA

B31    TTTCCAGGA TCTGATC TTCCA TGTGACCTCCG GAAGCT
ACAI  C---TG--- AAGTC---    -G-A---T-T---  T-T-
Ip90  C---T--A- AAGTC--G     G-A---T-TT---  T-T-

B31    GACTCT
ACAI  -TT-A-
Ip90  -TT-A-
```

FIG. 3B-5

```
B31    MKKYLLGIGLILALIACKQNVSSLDEKNSVSVDLPGEMKVLVSKEKNKDGKYDLI
N40    ------------------------------------N-----------------
ZS7    ------------------------------------N-----------------
ACAI   ----------------------A------------------D------S-K
Ip90   ----------------------------------G-Q----D------S-M

B31    ATVDKLELKGTSDKNNGSGVLEGVKADKSKVKLTISDDLGQTTLEVFKEDGKTLV
N40    -----------------------------------------------------
ZS7    -------I---------------T-D----A----A---SK--F--L------
ACAI   ---------D-------------T-E-T--A----AE--SK--F--I------
Ip90   ------------------------------------------------------

B31    SKKVTSKDKSSTEEKFNEKGEVSEKIITRADGTRLEYTGIKSDGSGKAKEVLKGY
N40    ------------------------------------E-----------------
ZS7    --R--S----T--D-M-----L-A-TM--EN--K----EM---T-----------S-
ACAI   ----------------------A---T-V--N----D---KT---------NF
Ip90   ---L-------------------A-----------------D---DF
```

FIG. 5A-1

```
                180                                           210
B31   VLEGTLTAE  KTTLVVKEGTVTLSKNISKSGEVSVELNDTDSSAATKKTAAWNSG
N40   ---------  --------------------------------------------
ZS7   ---------  --------------------------------------------
ACAI  T---RVAND  -V--E--------E-A-----T-A----NTTQ----G---D-K
Ip90  A----A-DG  --K-T-----K-T-----V---H--N---IT-----S--TTQ----GT-D-K 240                                           270
B31   TSTLTITVNSKKTKDLVFTKENTITVQQYDSNGTKLEGSAVEITKLDEIKNALK
N40   -----------------------------------------------------
ZS7   -----S-------TQ-------QD----K---A--N---T-----KT----L---
ACAI  -----S----R--N--------D-----K---A--N---K-----T-K-L-D---
Ip90  
```

FIG. 5A-2

```
                        30
B31     M RLLIGFALALALIGCAQKGAESIG SQKENDLNLEDSSKKSHQNAKQD
ACAI      MKQY-LV----V-----A-S---T-PKST--DH--QEIIN-DNTPKDSK-DL
Ip90      MKKY-L-----V-----A-G-----P      -H--QDV--LK-DQKDDS-K-

90
B31     LPAVTEDSVSLFNGNKIFVSKEKNSSGKYDLRATIDQVELKGTSDKNNGS
ACAI    TVLAE-N--P---------------A---E---V-T----V------
Ip90    --L----T-K---N-E--I----EDD--E--SIV-K----L-E--T-A

120
B31     GTLEGSKPDKSKVKLTVSADLNTVTLEAFDASNQKISSKVTKKQGSITEE
ACAI    -K----T-A--T--AM-IAD-----I-V-TY---K-TG-E-V----VIK-
Ip90    -E----L-A----TML--D-----I-I-TY-P--K----Q-A----L---

180
B31     TLKANKLDSKKLTRSNGTTLEYSQITDADNATKAVETLKNSIKLEGSLVV
ACAI    SY--------I-----I--E-E----EM--SS-D-----G------G
Ip90    -Y-TS--SA--I----N--I--TEM-----S-------G-T----G

240
B31     GKTTVEIKEGTVTLKREIEKDGKVKVFLND TAGSN KKTGKWEDSTSTL
ACAI    ----KLT---I--T----Q----IY----T-S-- T---AT-NET-N---
Ip90    ----LT-----------K----A-T---D-   -S-AT----AV-N-TS---
```

FIG. 5B-1

```
           270
B31   TISADSRKTKDLVFLTDGTITVQQYNTAGTSLEGSASEIKNLSELKNALK
ACAI  -------F----------A-D---K---NS----D-AA---A-------
Ip90  -V--EG----F-------N--K---T---K--T---D--EA---A-----
```

FIG. 5B-2

BORRELIA BURDORFERI OSP A AND B PROTEINS AND IMMUNOGENIC PEPTIDES

This application is a continuation-in-part of application Ser. No. 08/079,601, filed Jun. 22, 1993, now U.S. Pat. No. 5,523,089, which is a continuation of U.S. application Ser. No. 07/924,798, filed Aug. 6, 1992, now abandoned, which is a continuation of U.S. application Ser. No. 07/422,881, filed Oct. 18, 1989, now abandoned, claiming priority from Danish application 5902/88, filed Oct. 24, 1988. This application is a division of application Ser. No. 08/137,175, filed Oct. 26, 1993 now U.S. Pat. 5,777,095, as the National Phase of PCT/US92/08972, filed Oct. 22, 1992 as a continuation-in-part of application Ser. No. 07/779,185 filed Oct. 22, 1991 now abandoned.

The present invention relates to valuable and useful developments in diagnostics of and vaccines against *Borrelia burgdorferi* based upon new findings about new classes of *Borrelia burgdorferi* (from now on *B. burgdorferi*) and especially about DNA and peptide sequences from the *B. burgdorferi* strains ACA1 and Ip90 (the same as Iper90) and their relationship to *B. burgdorferi* strain B31, including special sequences from the three different strains of *B. burgdorferi* useful as primers in the PCR-DNA detection of *B. burgdorferi* in specimens from animals, including humans, a diagnostic kit for diagnosing Lyme disease in animals, including humans, DNA sequences form *B. burgdorferi* strains ACA1 and Ip90 encoding polypeptides related to the outer membrane protein OspA and OspB, a polypeptide encoded from ACA1 and Ip90, epitopes from OspA and OspB, and a vaccine against Lyme disease comprising one or more epitopes from OspA and OspB.

BACKGROUND OF THE INVENTION

Lyme disease is a zoonosis caused by the tick-borne spirochaete *B. burgdorferi*. When a susceptible host is bitten by an ixodid tick, *B. burgdorferi* organisms enter the skin. In humans the initial skin manifestation is termed erythema chronicum migrans (ECM) whereas a long-standing infection of the skin produces acrodermatitis chronica atrophicans. The Borrelia organisms also enter the circulatory system of the host and are distributed to various organs, including the brain and joints. A secondary spread of the pathogens produces a variety of clinical syndromes, including lymphocytic meningoradiculitis, myocarditis and chronic arthritis. In many patients the infection of some tissues, particularly the brain and joints, persists for years and can be severely disabling. These forms of chronic Lyme disease are a consequence of the host's inability to rid itself of the infectious agent and perhaps the development of an autoimmune reaction.

Diagnosis of Lyme disease has chiefly been based on clinical evidence. The best marker during the primary stage of infection has conventionally been the presence of erythema chronicum migrans (ECM) but these skin lesions may not always develop or they may manifest atypically. Moreover, Lyme disease can be confused with other illnesses characterized by neurologic or arthritic manifestations. When clinical histories are incomplete, serologic testing with determination of antibody titers is the best conventionally laboratory method of diagnosis. Indirect fluorescent antibody (IFC) staining tests and enzyme-linked immunosorbent assays (ELISA) are used to detect total immunoglobulins or class-specific IgM and IgG antibodies to *B. burgdorferi*. ELISA is usually preferred because the procedures are more easily standardized and automated and because absorbance values can be statistically analyzed to give more objective results.

*B. burgdorferi* spirochaetes are helically shaped, motile cells with an outer cell membrane that surrounds a protoplasmic cylinder complex, consisting of the cytoplasm, the cell wall, the inner cell membrane and the flagella which are located not at the cell surface but in the periplasmic space between the outer cell membrane and the protoplasmic cylinder. The outer cell membrane and the flagella are assumed to play an important role in the host-parasite interactions during the disease and has been subjected to several investigations, identifying major surface-exposed proteins as important immunogens.

It has been shown that the earliest IgM antibodies formed against antigens of the *B. burgdorferi* strain B31, which was deposited in the American Type Culture Collection in 1983 with the accession number ATCC 35210, are directed against a genus-specific flagellar polypeptide termed flagellin having a molecular weight of 41 kd (18) and which reacts with monoclonal antibody H9724. IgG antibodies are also first directed to the 41 kg flagellin, but with advancing disease IgG antibodies form against other immunogens, especially against two abundant proteins with molecular weights of 31 kg and 34 kd. These two proteins, which have been denoted OspA (31 kd) and OspB (34 kd), have been found to be located at the *B. burgdorferi* surface and embedded in its outer fluid cell membrane. The OspA protein has been found to be less variable in its molecular weight and in its reactivity with monoclonal antibody H5332 (10), whereas the molecular weight of OspB proteins from different *B. burgdorferi* strains vary and the OspB proteins of different strains also show varying reactivity with two monoclonal antibodies against OspB (H6831 and H5TS) (9). The main variation among OspA proteins is found between isolates from Europe and the United States.

Conventional diagnostic tests for Lyme disease have used whole spirochaetal sonic extracts as test antigens in ELISA to detect antibodies to *B. burgdorferi*, but this test yields unsatisfactory low diagnostic sensitivity (20 to 60%) during the early stage of infection, possibly due to a slow and late-appearing antibody response and to the inclusion of irrelevant cross-reacting antigens in the whole-cell preparations. In addition, the use of whole cells as test antigens may result in the occurrence of false positive reactions. For example, among patients with syphilis and in areas where a closely related relapsing fever Borrelia spp. co-exist with *B. burgdorferi*, serologic differentiation of Lyme disease from tick-borne relapsing fever is difficult. Detection of IgG antibody to *B. burgdorferi* in later stages of infection can help in distinguishing Lyme disease form aseptic meningitis, multiple sclerosis, serum negative rheumatoid arthritis, juvenile rheumatoid arthritis, and Reiter's syndrome.

The antigen-antibody diagnostic approach has been found not to work as well in connection with Lyme disease as in connection with many other infectious diseases.

One of the reasons for this is that only a low number of spirochaetes is present and that the antigens in the outer membrane of the spirochaetes are hard to detect for the immune system of the infected organism.

Another reason is that the antibody response to the *B. burgdorferi* infection first arises weeks after the bite of the tick, and in many cases first after the patient has shown clinical signs of the disease.

It would be desirable to provide a diagnostic tool which is able to diagnose a *B. burgdorferi* infection at all stages, also, at very early stages even before the clinical signs of infections appear and the diagnostic tool being independent of the causative infective *B. burgdorferi* strain.

A most promising and sensitive method for diagnosing the Lyme disease agent is that of detecting a single *B. burgdorferi* organism by PCR amplification.

Nielsen S. L. et al. Molecular and Cellular Probes (1990) 4, 73–79, Detection of *Borrelia burgdorferi* DNA by the polymerase chain reaction, and Malloy, D. C. et al, Journal of Clinical Microbiology, June 1990, p. 1089–1093, Detection of *Borrelia burgdorferi* Using the Polymerase Chain Reaction, both disclose the use of DNA-sequences from only *B. burgdorferi* strain B31 in the preparation of primers useful in the PCR-DNA diagnostic of Lyme disease.

WO91/06676 discloses the use of DNA primers associated with the SC plasmid in the diagnostic of Lyme disease, but does not disclose the sequence of the primers.

ERP 421 725 A1 discloses nucleic acid probes useful for identifying *B. burgdorferi* in samples. The probes are designed from *B. burgdorferi* strains in The United States and Europe.

EP 445 135 discloses the use of a DNA fragment from the OspA gene from the B31 strain in PCR-DNA diagnostic of *B. burgdorferi* infection in mammals, including humans, as well as the use of immunogenic polypeptides found to be antigenic when assessed with monoclonal antibodies directed against OspA in the preparation of a vaccine immunizing mammals, including humans, against Lyme disease. EP 445 135 discloses, inter alia, three contemplated epitopes which are small fragments of B31 OspA: Lys-Glu-Lys-Asn-Lys-Asp, Ser-Lys—Lys-Thr-Lys-Asp, and Lys-Ala-Asp-Lys-Ser-Lys. To the extent this is relevant, these fragments and their utility and use as epitopes is disclaimed in the present invention.

Rosa, P. A. et al., Journal of Clinical Microbiology, March 1991, p.524–532, Polymerase Chain Reaction Analyses Identify Two Distinct Classes of *Borrelia burgdorferi* discloses PCR primers used in the identification.

One object of the present invention is to provide non-immunological assays by providing nucleotide sequences which can hybridize with different strains of *B. burgdorferi* from different geographical regions so that a diagnostic tool for detecting *B. burgdorferi* spirochaetes independent of causative infective strain of *B. burgdorferi* is obtained. Another object is to provide novel DNA fragments related to *B. burgdorferi*. A further object of the invention is to provide antigenic polypeptides, an antigenic composition and a vaccine for immunizing animals, including humans, against Lyme disease substantially independent of the infective *B. burgdorferi* strain causing the disease.

BRIEF DESCRITION OF DRAWINGS

Figure 1:
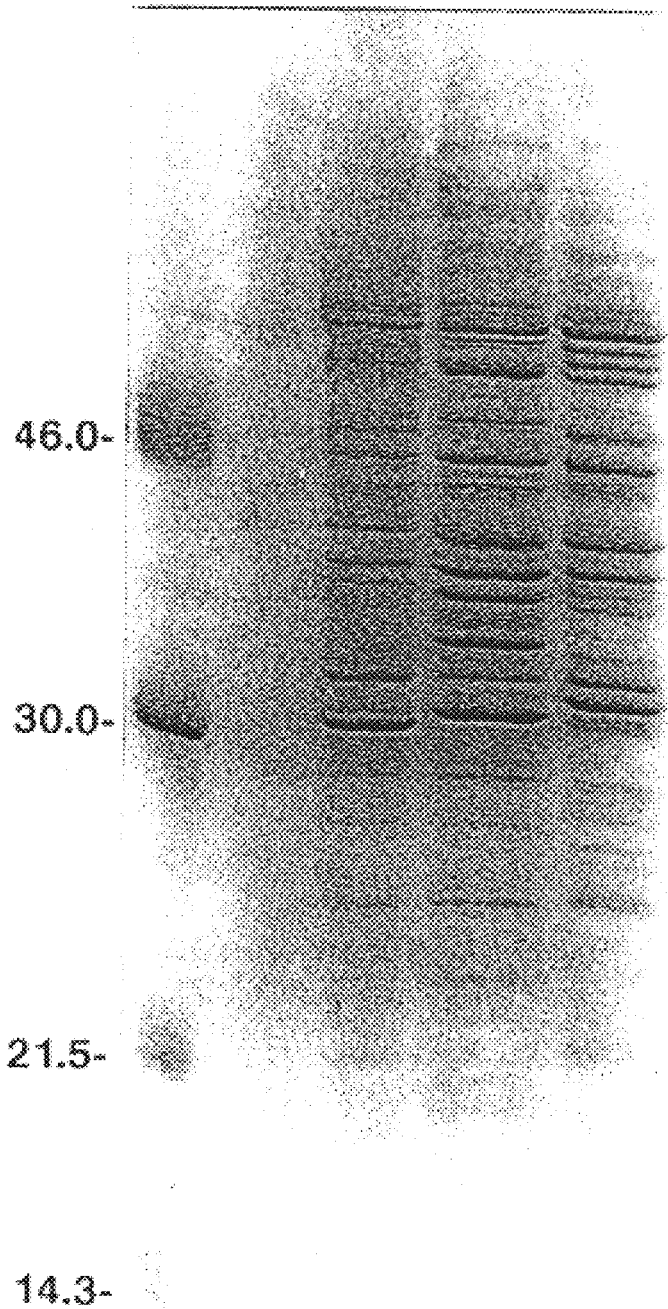
FIG. 1 shows Coomassie blue-stained 12.5% SDS-PAGE gel of whole cell lysates of B31, ACA1 and Ip90.
Figure 2A:
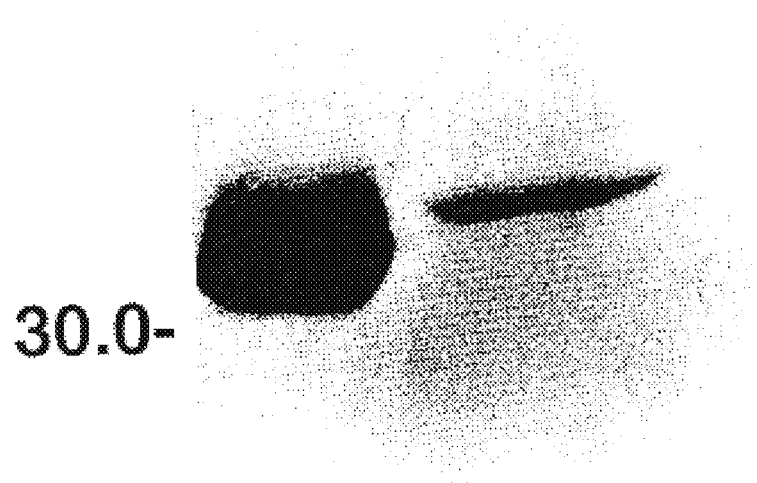
FIG. 2A, 2B, 2C, 2D (FIGS. 2aA, 2aB, 2bC, 2bD) show results of Western Blots (MAbs H5332, H3TS, H6831, and polyvalent polyclonal anti-sera against whole cell)
Figure 2B:
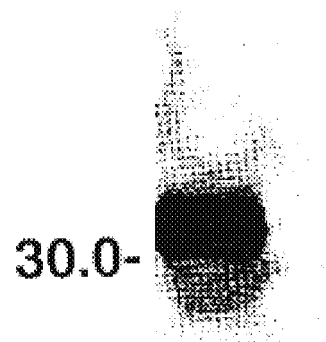
Figure 2C:
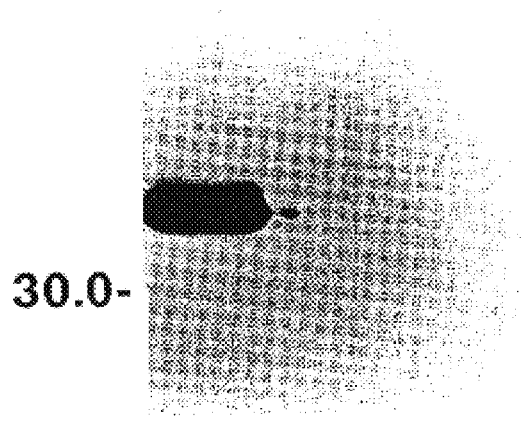
Figure 2D:
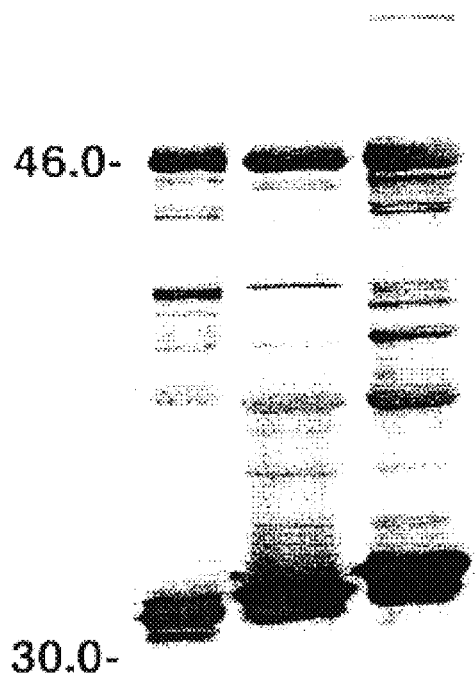
Figure 4:
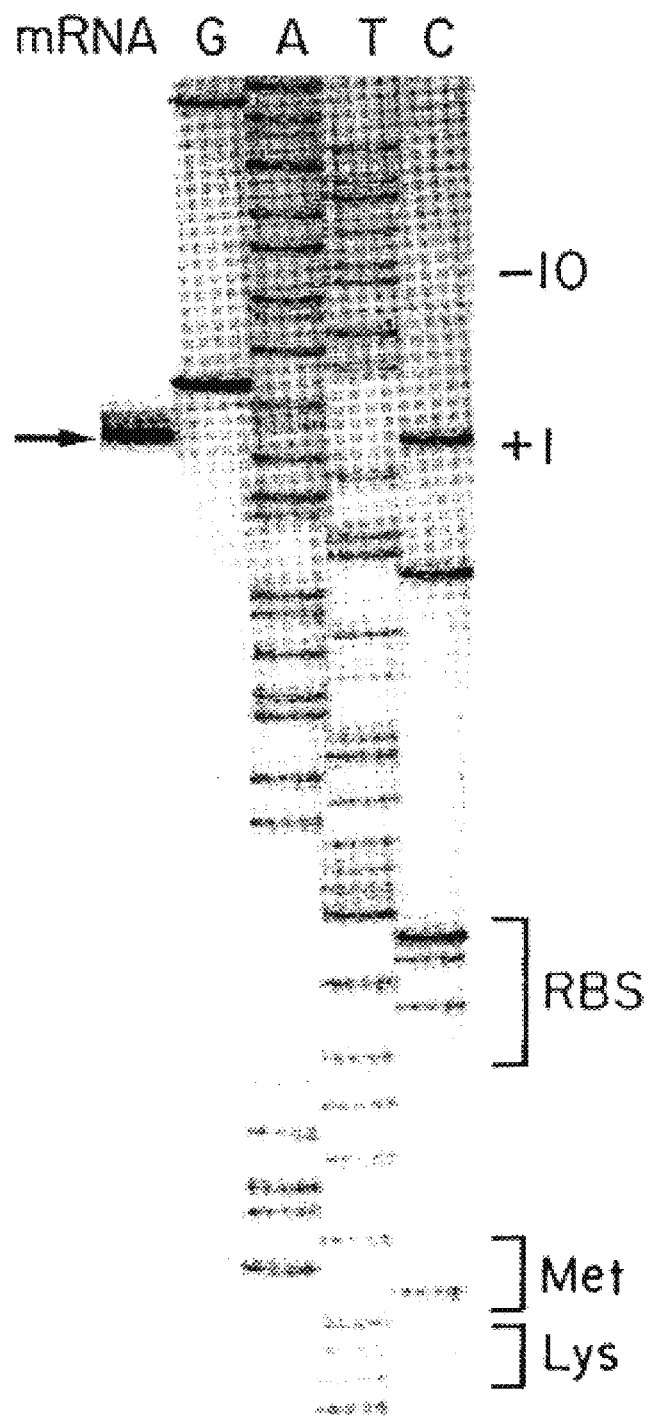
Figure 6A:
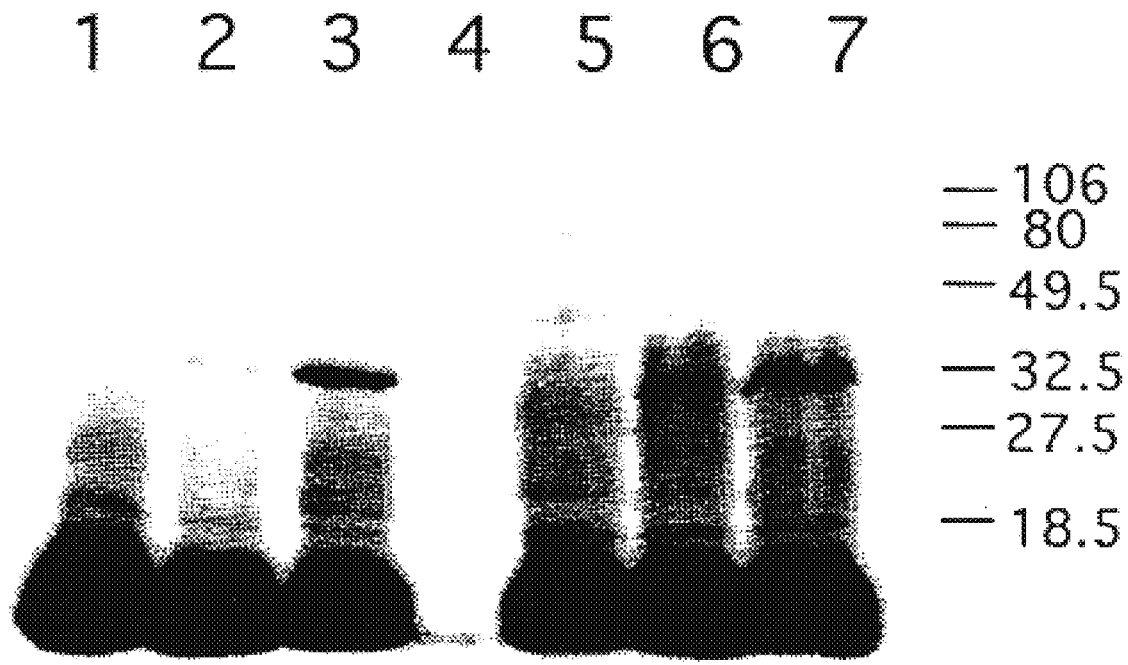
Figure 6B:

FIG. 3 (FIGS. 3a1 to 3a7 and 4b1 to 3b5) show DNA sequences of B31, ACA1 and Ip90 osp operon, including ospA and ospB in a comparative arrangement, with ospA sequences from Z57 and N40;

FIG. 4 shows the primer extension of osp mRNA together with the corresponding sequence ladder of osp DNA;

FIG. 5 (FIGS. 5a1, to 5a2 and 5b1 to 5b2) show amino acid sequences of OspA and OspB (ACA1, Ip90, B1, Z27 and N40 OspA in FIGS. 5a1 to 5a2; ACA1, Ip90, B31 OspB in FIGS. 5ato 5a2); and FIGS. 6A and 6B show results of expression studies of recombinant E. coli.

DESCRIPTION OF THE INVENTION

In one aspect, the invention relates to a method for detecting the presence of a *B. burgdorferi* organism in animals, including humans, the method comprising subjecting a specimen from the animal, such as a body fluid, such as blood, serum, cerebrospinal fluid, synovial fluid, pericardial fluid or urine, or a tissue biopsy, or, when the animal is an arthropod, the whole animal, to PCR-DNA analysis which either A) uses a nucleotide primer sequence which comprises at least 11 nucleotides, the primer sequence being identical or substantially identical to a sub-sequence of at least two of three OspA and OspB DNA sequences derived from *B. burgdorferi* species I, II and III, respectively, or B) uses a combination of at least two nucleotide primer sequences, each of which comprises at least 11 nucleotides, one sequence being identical or substantially identical to a sub-sequence of the OspA and OspB DNA from a first *B. burgdorferi* species, another sequence being identical or substantially identical to a sub-sequence of the OspA and OspB DNA from another *B. burgdorferi* species, and optionally a third sequence which is identical or substantially identical to a sub-sequence of the OspA and OspB DNA from the third *B. burgdorferi* species, the substantial identity being such that the said primer sequence will hybridize to the sub-sequence under conventional hybridization conditions (reference Sam Brooks), or under high stringency hybridization conditions comprising hybridization at 67° C. in 2×SSC and final washing at 67° C. in 1×SSC, or under medium high stringency hybridization conditions comprising hybridization at 67° C. in 3×SSC and final washing at 67° C. in 1×SSC.

It has previously been shown that *B. burgdorferi* strains of different geographical origin differ in DNA sequence profiles, and until now two classes of *B. burgdorferi* have been disclosed (36).

According to the present invention the OspA and OspB genes from two *B. burgdorferi* strains ACA1 and Ip90 have been sequenced and compared to the OspA and OspB gene sequence from strain B31, previously sequenced (14). The differences seen when comparing the sequences from *B. burgdorferi* strains B31, ACA1 and Ip90 indicate that *B. burgdorferi* may be placed into three different classes or species I, II and III, using B31, Ip90 and ACA1 as reference strains, instead of placing *B. burgdorferi* into two classes.

The method proves a diagnostic tool which may be used to diagnose *B. burgdorferi* infection at all stages, even before the patient shows any clinical signs of Lyme disease, because the *B. burgdorferi* spirochaetes are detected instead of the antibodies towards the spirochaetes. Also, the method is able to detect even a single *B. burgdorferi* spirochaete and therefore the sensitivity of the method is very high.

Furthermore, the method is useful in diagnosing whether a Ixodes tick is a vector for *B. burgdorferi*, which is of especially interest in areas with endemic *B. burgdorferi* infections.

The *B. burgdorferi* strain ACA1 is a Swedish isolate from the tick vector *I. ricinus*, and the *B. burgdorferi* strain Ip90 is an isolate from the Soviet Union from a region in which the tick vector is *I. persulcatus*. The known *B. burgdorferi* strain B31 is a North American isolate from the tick vector *I. damminii*.

Comparison between the known B31 sequence and the two novel sequences form ACA1 and Ip90, respectively, reveals that there are several regions having conserved sequences either totally or with a few mismatches of nucleotides in the regions, FIG. 3.

As mentioned above, the strains discussed herein are from different geographical regions. According to a further aspect of the invention, primers are provided which can detect *B. burgdorferi* of all classes by the PCR amplification method, by using nucleotide sequences from regions having the same or substantially the same DNA-sequence in all the three strains, therefore the invention relates to a method wherein the PCR-analysis either A) uses a nucleotide primer sequence which comprises at least 11 nucleotides, the primer sequence being identical or substantially identical to a sub-sequence of at least two of the three DNA sequences derived from *B. burgdorferi* strains B31, Ip90 and ACA1, respectively, shown in FIG. 3 herein, or preferred that the primers are somewhat longer, such as comprising at least 12 or 13 nucleotides, preferably at least 15 nucleotides, and in many cases about 18 nucleotides or even higher.

The most interesting primers for use in a general PCR-DNA detection of *B. burgdorferi* are, of course, primers which are especially capable of amplifying DNA from a *B. burgdorferi* irrespective of the particular strain or species of the *B. burgdorferi*. Primer sequences of particular interest in this connection are primers corresponding to subsequences which are identical or substantially identical in all three of the species I, II and III, such as in all three of the strains B31, Ip90 and ACA1. Primers fulfilling this condition are, e.g. primers which are fragments comprising a sequence which is identical or substantially identical to one of the following sequences (or one of their complementary sequences):

| | |
|---|---|
| 5'-GTATTAAGTTATATTAATAT-3' | (SEQ.ID.NO. 1, bp 123–142) |
| 5'-AAAAGGAGAATATATTATGA-3' | (SEQ.ID.NO. 1, bp 584–607) |
| 5'-AAAAATATTTATTGGGAATA-3' | (SEQ.ID.NO. 1, bp 776–794) |
| 5'-GGAAAAGCTAAAGAGGTTTTAAAA-3' | (SEQ.ID.NO. 1, bp 806–817) |
| 5'-ACTTCAACTTTAACAATTA-3' | (SEQ.ID.NO. 4, bp 85–104) |
| 5'-AATAAGGAGAATTTATGA-3' | (SEQ.ID.NO. 4, bp 111–130) |
| 5'-AAAAAAACTAAA-3' | (SEQ.ID.NO. 4, bp 948–965). |

B) uses a combination of at least two nucleotide primer sequences, each of which comprises at least 11 nucleotides, one sequence being identical or substantially identical to a sub-sequence of the OspA and OspB DNA from a first *B. burgdorferi* strain as shown in FIG. 3 herein, another sequence being identical or substantially identical to a sub-sequence of the OspA and OspB DNA from another of the *B. burgdorferi* strains as shown in FIG. 3 herein, and optionally a third sequence which is identical or substantially identical to a sub-sequence or the OspA and OspB sequence form the third of the *B. burgdorferi* strains as shown in FIG. 3 herein, the substantial identity being as defined above.

In the present context the term "substantially identity" is intended to indicate that the sequences only have one or a few mismatches, and that these mismatches will not interfere with the annealing of the primer sequence in question to its target sequence with sufficient specificity. A more precise definition is based on hybridization: A primer sequence which is substantially identical with a particular subsequence in the context of the present invention will hybridize to the sub-sequence under defined hybridization conditions. Several sets of conventional hybridization conditions relevant in the present context are described in (52). For a primer, however, a rather high degree of specificity is often required, and this is reflected in the above specification of high stringency hybridization conditions comprising hybridization at 67° C. in 2×SSC and final washing at 67° C. in 1×SSC, or medium high stringency hybridization conditions comprising hybridization at 67° C. in 3×SSC and final washing at 67° C. in 1×SSC.

The primers may, in principle, be shorter than the 11 nucleotides mentioned above, but this is normally not preferred for specificity reasons. On the contrary, it is normally As will be seen from FIG. 3 which shows the DNA sequences (a single strand of the double-stranded DNA shown) of the *B. burgdorferi* strains B31, ACA1, and Ip90, the above specific DNA fragments represent regions showing full or almost full identity between the three strains.

While PCR analysis can be performed using a single primer, it is, of course, normally more advantageous to utilize the exponential amplification obtained when using a set of primers amplifying complementary strands such as is normal in PCR. Therefore, in a preferred embodiment of this aspect of the invention, a set of primers is used, the first primer of the set being a primer as defined above, the second primer comprising a sequence which is identical or substantially identical to a subsequence of a strand complementary to OspA or OspB DNA from at least one of *B. burgdorferi* strains B31, Ip90 and ACA1 as shown in FIG. 3 herein, the subsequence of the complementary strand being downstream of the first primer in relation to the direction of expression of the first primer, the substantial identity being as defined above. When a set of primers is used, it is normally preferred that they have substantially the same degree of identity with their target sequences. The distance between the primers in the set may be from 25 to 300 bp, such as 50 to 200 bp.

While the embodiments discussed above focus on the establishment of a PCR analysis which will detect DNA from a *B. burgdorferi* spirochaete irrespective of which strain it is, another interesting aspect of the invention is a PCR analysis making it possible to detect the presence of a *B. burgdorferi* spirochaete in a specimen with strain specificity, in other words to detect specifically a *B. burgdorferi* of one of the now-identified three main classes or species.

It is of interest to be able to know exactly the class and possibly also the strain responsible for an infection because it seems as if different classes of *B. burgdorferi* relate to different symptom complexes. In Scandinavia where *B.*

*burgdorferi* from class III, represented by ACAI is common the symptoms arising from *B. burgdorferi* infections are more often neurological symptoms compared to what is seen in other areas. Contrary to this arthritis resulting from *B. burgdorferi* infection appears more often in USA where *B. burgdorferi* class I, represented by B31, is common than elsewhere.

In this aspect, the specimen is subjected to PCR-DNA analysis using as a primer a DNA sequence which comprises at least 11 nucleotides, the sequence being identical or substantially identical to a subsequence of OspA and OspB DNA from one of the *B. burgdorferi* species I, II and III which subsequence is different from any subsequence of the two other species, the difference being such that the sequence will not anneal to DNA from the two other species, the substantial identity being as defined above.

Also, with respect to species or strain specifically detection of *B. burgdorferi* it is advantageous to use a set of primers, the first primer of the set being a primer as defined above, the second primer comprising a sequence which is identical or substantially identical to a subsequence of a strand complementary to OspA or OspB DNA from the same *B. burgdorferi* species, preferably of the same strain as the first primer, the subsequence of the complementary strand being downstream of the first primer in relation to the direction of expression of the first primer, the substantial identity being as defined above.

In a preferred embodiment of the invention the subsequence of the first primer is identical or substantial identical to a subsequence of OspA and OspB from one of the *B. burgdorferi* strains B31, ACAI and Ip90 as shown in FIG. 3 and the second primer being as defined above.

Again, the length of the primer is preferably at least 12, more preferably at least 13 or 15 and often about 18, such as explained above.

The difference in sequences which is decisive in this type of PCR according to the invention can be identified directly from FIG. 3 and confirmed by simple experiments.

Especially, the first primer is a DNA sequence of 15–25 nucleotides which differs from any subsequence of the two other strains in at least 4 nucleotides per 20 nucleotides of the primer, preferably the differences being in 5 nucleotides per 20 nucleotides.

When differences are present in 4 or more nucleotides per 20 nucleotides of a primer a minimum of cross-reaction between the primer and a *B. burgdorferi* strain from another species is possible irrespective of the stringency hybridization conditions.

In order to detect an exact *B. burgdorferi* species or strain without knowing the species forehand, it is preferred to use a set of primers wherein each primer comes from a different species or strain and differs from any subsequences of the other species and strains in at least 4 nucleotides per 20 nucleotides of primers. In a preferred embodiment 3 sets of primers are used, the sets comprising a first primer of the first set which is a DNA sequence of 15–25 nucleotides identical or substantially identical to a subsequence of the DNA from *B. burgdorferi* strain B31 shown in FIG. 3 which differs from any subsequence of the DNA sequence from the two other *B. burgdorferi* strains shown in FIG. 3 for at least 4 nucleotides per 20 nucleotides of the primer, preferably for at least 5 nucleotides per 20 nucleotides, a first primer of the second set which is a DNA sequence of 15–25 nucleotides identical or substantially identical to a subsequence of the DNA from *B. burgdorferi* strain ACA1 shown in FIG. 3 which differs from any subsequence of the DNA sequence from the two other *B. burgdorferi* strains shown in FIG. 3 for at least 4 nucleotides per 20 nucleotides of the primer, preferably for 5 nucleotides per 20 nucleotides, a first primer of the third set which is a DNA sequence of 15–25 nucleotides identical or substantially identical to a subsequence of the DNA from *B. burgdorferi* strain Ip90 shown in FIG. 3 which differs from any subsequence of the DNA sequence from the two other *B. burgdorferi* strains shown in FIG. 3 for at least 4 nucleotides per 20 nucleotides of the primer, preferably for 5 nucleotides per 20 nucleotides, and for each set, a second primer which is a subsequence of the DNA sequence of the complementary strand of the same strain as the first primer of the set, the subsequence of the complementary strand being downstream of the first primer in relation to the direction of expression of the first primer, the second primer preferably differing from any subsequences of the DNA sequence of the two other strains.

Again, it is preferred to use a set of 2 primers for each primer defined above, the second primers coming from the complementary strand of the same *B. burgdorferi* species or strain.

Species specifically diagnostic is especially interesting if all the strains from a particular *B. burgdorferi* species is detected and at the same time that no other strains are detected, i.e. that both the sensitivity and the specificity are high. This will most probably occur if the primers are subsequences that are well conserved within a species but differs from any subsequences from any other strains. OspA sequences are generally better conserved within species than OspB, therefore it is preferred to use primers that are subsequences identical or substantially identical to subsequences from the DNA sequences encoding OspA, such as those shown in FIG. 3 coding for OspA.

| | |
|---|---|
| AACAATGGATCTGGAGTA | (SEQ.ID.NO. 1, bp 326–343) |
| AACAACGGTTCTGGAACA | (SEQ.ID.NO. 7, bp 332–349) |
| GTCAAGAAAAGTAAGTTCTA | (SEQ.ID.NO. 4, bp 456–475) |
| and | |
| CTCTAACTGCTGAAAAAAC | (SEQ.ID.NO. 1, bp 627–645) |
| AAGTAGCTAATGATAAAGT | (SEQ.ID.NO. 4, bp 635–653) |
| CTCTAGCTGCTGACGGCAAAAC | (SEQ.ID.NO. 7, bp 633–654) |

The PCR analysis using the special primers discussed herein is performed in accordance with usual PCR technique such as described in the literature, e.g. (51). Thus, for the detection, the primer may be labeled, such as with radioactive labels, fluorescent dyes, and bictin, or labeled nucleotide triphosphates (e.g. labeled with thymidine) can be included in the PCR reaction to label the PCR amplification product.

The PCR primers used according to the invention may be prepared using well-known methods. Thus, they may be prepared by oligonucleotide synthesis, or they may be prepared by fragmentation of a larger nucleotide sequence using suitable restriction enzymes. The labelling of the primers can be performed by methods well-known per se.

As is conventional, the PCR reagents can be included in suitable PCR kits.

While the above discussion emphasizes the use of a single kind of primer capable of detecting all the strains of *B. burgdorferi* in a universal test, such a test can, of course, also be established by using a combination of different primers, comprising, for each of the strains of *B. burgdorferi* to be detected, a type of primer unique to the strain. Preferably, for specific detection the PCR kit should include a set of 2 primers for each species to be detected, e.g. a kit having 3 sets of 2 primers in appropriate amounts together with other PCR reagents.

Using the PCR analysis method or kit as described above, it is possible to diagnose Lyme disease as well as pre-clinical borreliosis in mammals, including humans, independent of the strain of *B. burgdorferi* that have caused the disease.

In another embodiment, the present invention relates to important novel DNA fragments and their use.

DNA fragments of the invention are fragments encoding the OspA and OspB of *B. burgdorferi* of the Swedish strain ACA1 and of the Soviet strain Ip90 or any modifications of said sequence encoding a polypeptide which is functionally equivalent to OspA and OspB from ACA1 and Ip90, respectively.

The term "functional equivalent" is intended to include all immunogenically active substances with the ability of evoking an immune response in animals, including humans to which the equivalent polypeptide has been administered, e.g. as a constituent of a vaccine which immune response is similar to the immune response evoked by the OspA and OspB. Thus, equivalent polypeptides are polypeptides capable of conferring immunity to Lyme disease.

OspA and OspB are outer surface proteins in *B. burgdorferi* which are encoded by DNA-sequences found within the same operon. The genes encoding OspA and OspB are located on a double stranded linear plasmids.

One embodiment of the invention is a DNA fragment comprising a nucleotide sequence as shown in FIG. 3 herein for ACA1, or for Ip90, a subsequence thereof which comprises at least 15 nucleotides and which hybridizes to said nucleotide sequence under high stringency hybridization conditions comprising hybridization at 67° C. in 2×SSC and final washing at 67° C. in 1×SSC, or under medium high stringency hybridization conditions comprising hybridization at 67° C. in 3×SSC and final washing at 67° C. in 1×SSC, or under low stringency conditions such as 6×SSC and 67° C. and subsequent wash at 4×SSC and 67° C., or a homologue of said nucleotide sequence which encodes a polypeptide identical to or substantially identical to a polypeptide encoded by said nucleotide sequence and which hybridizes to said nucleotide sequence under high or medium high or low stringency hybridization conditions as defined above.

An example of a hybridization procedure is described in connection with the examples.

In connection with the DNA fragment aspect of the present invention, the term "subsequence" is used to denote a nucleotide sequence which is derived from the nucleotide sequence shown by modifications e.g. of the types described below, and which has retained a characteristic nucleotide sequence thereof, the characteristic nucleotide sequence being a sequence which is capable of hybridizing to the nucleotide sequence in question under the conditions as explained herein. Typically, the subsequence is a part of the DNA fragment, that is, the subsequence is a number of nucleotides shorter than the DNA fragment.

In accordance with what is explained above, the DNA fragment of the invention may be one which has been modified by substitution, addition, insertion, deletion, transposons or rearrangement of one or more nucleotides in the sequence, e.g. for the purpose of establishing a sequence which, when expressed in a suitable host organism, results in the production of a polypeptide which has a substantial similarity to the OspA or OspB protein or a fragment thereof, and which has retained the immunological activity of the protein or the fragment.

The complete fragment shown in FIG. 3 comprises fragments coding for OspA protein and for OspB protein. One particular aspect of the invention is a DNA fragment as defined above comprising a nucleotide sequence starting at nucleotide 37 and terminating at nucleotide 859 of the nucleotide sequence shown in FIG. 3 herein encoding a cell membrane protein from *B. burgdorferi,* strain ACA1 (corresponding to SEQ. ID. NO. 4, bp 127–948), or from *B. burgdorferi,* strain Ip90, (corresponding to SEQ. ID. NO. 7, bp 125–949) said protein being designated OspA, or a subsequence or homologue of said nucleotide sequence, the nucleotide numbering being based on the B31 numbering in the manner shown in FIG. 3. Another particular aspect of the invention is a DNA fragment comprising a nucleotide sequence starting at nucleotide 865 and terminating at nucleotide 1855 of the nucleotide sequence shown in FIG. 3 herein encoding a cell membrane protein from *B. burgdorferi,* strain ACA1 (corresponding to SEQ. ID. NO. 4, bp 962–1861), or from *B. burgdorferi,* strain Ip90 (corresponding to SEQ. ID. NO. 7, bp 959–1843), said protein being designated OspB, or a subsequence or homologue of said nucleotide sequence, the nucleotide numbering being based on the B31 numbering in the manner shown in FIG. 3.

The modifications or homologues of the DNA fragments encoding OspA, OspB or a part thereof falling within the definitions herein above may be prepared, e.g. by subjecting the native DNA fragments to mutagenization, e.g. by treatment with ultraviolet radiation, ionizing radiation or a chemical mutagen such as mitomycin C, 5-bromouracil, methyl-methane sulphonate, nitrogen mustard or a nitrofuran, in particular so as to alter some of the properties of the gene product expressed from the mutagenized sequence substantially without changing the immunologic activity of the gene product. Especially, site-directed mutagenesis or directed mutagenesis is useful. All of these techniques are described in textbooks in the field, e.g. in (52) and (53).

The DNA sequences shown in FIG. 3 are discussed in detail in Example 1 herein.

Especially interesting DNA fragments are fragments of at least 15 nucleotides which encode immunologically active parts of OspA or Osp B, i.e. the antigenic determinants or epitopes of OspA, that is, in particular, polypeptides which are capable of interacting with immunocompetent cells to elicit an immune response against *B. burgdorferi* as well as lipidated OspA and OspB or lipidated antigenic determinants or epitopes of OspA or OspB. For vaccine purposes the use of lipidated polypeptides have proven a very interesting alternative to the use of non-lipidated polypeptides together with adjuvants.

In WO 90/04414 by the same applicant as the present application, DNA encoding OspA and OspB also encoding a cleavage site of a lipoprotein signal peptidase is disclosed. It has now been demonstrated that naturally occurring OspA and OspB are lipoproteins by $^3$H-palmitic acid labelling.

It is considered advantageous to immunize mammals with lipidated OspA or OspB or immunogenic determinant thereof because an antibody response is seen also in cases where no adjuvant is used in the vaccine. When non-lipidated polypeptides are used both for priming and boosting a very little and sometimes not even recognizable antibody response appears. If lipidated polypeptides are used for priming an immune response, non-lipidated polypeptides may be used for boosting and are indeed very effective boosting antigens. In the present context the term "priming" means the initial immunization, whereas the term "boosting" means the optional additional immunizations administered at certain intervals after the priming dose to sustain the immune response to the antigen. The boosting dose is often smaller than the priming dose.

It is well known that some antigens are able to trigger an autoimmune response in some individuals but not necessarily in all individuals when their immune system is presented to the antigen. When preparing a polypeptide for use as an antigen in a vaccine it is advantageous to delete sequences that are suspected or proved to be autoimmunic epitopes. Therefore, a further aspect of the present invention is a DNA fragment a polypeptide wherein epitopes responsible for evoking autoimmunity in animals, including humans, when administered to the animal have been deleted.

In the OspA and OspB polypeptides encoded by the DNA fragments according to the invention, polypeptide fragments comprising sequences selected from the following:

```
LVSKEKNKDGKYDL    (SEQ.ID.NO. 2, residues 41–54),
LVSKEKDKDGKYSL    (SEQ.ID.NO. 5, residues 41–54),
KGTSDKNNGSGV      (SEQ.ID.NO. 2, residues 64–75),
KGTSDKTNGSGV      (SEQ.ID.NO. 5, residues 64–75),
KGTSDKNNGSGT      (SEQ.ID.NO. 8, residues 64–75),
LEGVKADKSKVKL     (SEQ.ID.NO. 2, residues 76–88),
LEGTKDDKSKAKL     (SEQ.ID.NO. 5, residues 76–88),
LEGEKTDKSKAKL     (SEQ.ID.NO. 8, residues 76–88),
KKVTSKDKSSTEEK    (SEQ.ID.NO. 2, residues 11–125),
RKVSSKDKTSTDEM    (SEQ.ID.NO. 5, residues 112–125),
KKVTLKDKSSTEEK    (SEQ.ID.NO. 8, residues 112–125),
KKTKDLVFTKEN      (SEQ.ID.NO. 2, residues 230–241),
KKTTQLVFTKQD      (SEQ.ID.NO. 5, residues 230–241),
RKTKNLVFTKED      (SEQ.ID.NO. 8, residues 231–242),
QYDSNGTKLEGS     (SEQ.ID.NO. 2, residues 247–258),
KYDSAGTNLEGT     (SEQ.ID.NO. 5, residues 247–258),
KYDSAGTNLEGK     (SEQ.ID.NO. 8, residues 248–259),
AVEITKLDEIKNALK   (SEQ.ID.NO. 2, residues 259–273),
AVEIKTLDELKNALK   (SEQ.ID.NO. 5, residues 259–273),
AVEITTLKELKDALK   (SEQ.ID.NO. 8, residues 260–274),
DLNLEDSSKKSHQNAK  (SEQ.ID.NO. 3, residues 31–46),
DQEIINSDNTPKDSKK  (SEQ.ID.NO. 6, residues 33–48),
DQDVEDLKKDQKDDSK  (SEQ.ID.NO. 9, residues 28–43),
KIFVSKEKNSSGK     (SEQ.ID.NO. 3, residues 64–76),
KIFVSKEKNSAGK     (SEQ.ID.NO. 6, residues 66–78),
EIFISKEKNEDDK     (SEQ.ID.NO. 9, residues 61–73),
KPDKSKVKLTVSAD    (SEQ.ID.NO. 3, residues 105–118),
```

-continued

```
KADKTKVAMTIADD    (SEQ.ID.NO. 6, residues 107–120),
KADKSKVTMLVSDD    (SEQ.ID.NO. 9, residues 102–115),
KKTGKWEDSTSTL     (SEQ.ID.NO. 3, residues 234–246),
KKTATWNETTNTL     (SEQ.ID.NO. 6, residues 237–249),
KKTAVWNDTSSTL     (SEQ.ID.NO. 9, residues 232–244),
KNLSELKNALK       (SEQ.ID.NO. 3, residues 286–296),
KDLAALKAALK       (SEQ.ID.NO. 6, residues 289–299),
KDLEALKAALK       (SEQ.ID.NO. 9, residues 284–294)
``` have been identified by computer analysis to be potential epitopes. Thus, such fragments and polypeptide fragments comprising sequences which are at least 70%, preferably at least 80% and more preferably at least 90% homologous with any of the above sequences and capable of interacting with immunocompetent cells to elicit an immune response against B. burgdorferi, said polypeptide fragment or fragments being smaller in size than naturally occurring OspA or OspB, are considered especially important antigenic/ immunogenic polypeptide fragments which will be valuable to elicit immune responses to B. burgdorferi. Accordingly, DNA fragments encoding these polypeptide fragments are especially interesting DNA fragments according to the invention.

The DNA fragments according to the invention, including the DNA fragments illustrated in FIG. 3 or a subsequences of said fragment may be derived by screening B. burgdorferi for nucleotide sequences hybridizing to a DNA probe prepared on the basis of the full or partial nucleotide sequence shown in FIG. 3. Further, the DNA fragment sequence may be a synthetic sequence, i.e. a sequence which is prepared according to standard procedures, e.g. as described in Matthes et al., 1984 (29).

The DNA fragment of the invention may be used for the production of OspA, OspB or parts thereof, especially immunologically active parts thereof. For this purpose, conventional recombinant DNA techniques may be employed. Thus, techniques comprising inserting the DNA fragment of the invention or one or more parts thereof into a suitable expression vector, transforming a host organism with the vector, cultivating the organism under conditions allowing expression of the inserted sequence and harvesting the resulting gene product, OspA or a part thereof, will the useful. Any of these procedures may be carried out by standard methods such as those disclosed in Maniatis et al., 1982 (30).

In order to prepare lipidated polypeptides it is necessary to use a DNA fragment which encodes a polypeptide comprising a lipoprotein signal peptide recognised by signal peptidase.

Consequently, the present invention further relates to a DNA fragment comprising a lipoprotein signal peptide recognized by signal peptidase, such as lipoprotein signal peptide II (SPaseII) especially, those DNA fragments wherein the lipoprotein signal peptide comprises a sequence in the C-terminal region recognized by signal peptidase II, eg. the sequences described by von Heijne, 1989 (63).

In a preferred embodiment a DNA fragment according to the invention is a DNA fragment encoding a lipoprotein signal peptide comprising the following sequence L-y-x-C in the C-terminal region, where y and x may be independent and each designate a small, neutral amino acid, such as isoleucine, alanine and glycine.

The lipoprotein signal peptide comprises preferably at least 10, such as at least 13 amino acids. In a preferred embodiment the DNA fragment the lipoprotein signal peptide comprises from 16 to 35 amino acids, such as from 16 to 29 amino acids.

Suitable expression vectors for the production of OspA, OspB or a part thereof are vectors which is capable of replicating in a host organism when transformed therein. The vector may either be one which is capable of autonomous replication, such as a plasmid, or one which is replicated with the host chromosome, such as a bacteriophage. Examples of suitable vectors which have been widely employed are pBR322 and related vectors as well as pUC vectors and the like. Examples of suitable bacteriophages include M13 and lambda.

The organism harbouring the vector carrying the DNA fragment shown in FIG. 3 or part thereof may be any organism which is capable of expressing said DNA fragment. The organism is preferably a microorganism such as a bacterium. Gram-positive as well as gram-negative bacteria may be employed. Especially a gram-negative bacterium such as E. coli is useful, but also gram-positive bacteria such as B. subtilis and other types of microorganisms such as yeasts or fungi or other organisms conventionally used to produce recombinant DNA products may be used.

In order to produce lipidated polypeptides the host harbouring the vector is to be a host which is capable of expressing lipidated polypeptides, such as E. coli.

Another type of organism which may be used to express OspA, OspB or a part thereof is a higher eukaryotic organism or cell, including a plant and mammal cell. However, also higher organisms such as animals, e.g. sheep, cattle, goats, pigs, horses and domestic animals, including cats and dogs, are contemplated to be useful as host organisms for the production of OspA or a part thereof. When a higher organisms, e.g. an animal, is employed for the production of OspA or a part thereof, conventional transgenic techniques may be employed. These techniques comprise inserting the DNA fragment shown in FIG. 5 or one or more parts thereof into the genome of the animal in such a position that OspA or part thereof is expressed together with a polypeptide which is inherently expressed by the animal, preferably a polypeptide which is easily recovered from the animal, e.g. a polypeptide which is secreted by the animal, such as a milk protein or the like. Alternatively, the DNA fragment of the invention could be inserted into the genome of the animal in a position allowing the gene product of the expressed DNA sequence to be retained in the animal body so that a substantial steady immunization of the animal takes place.

When a microorganism is used for expressing the DNA fragment of the invention, the cultivation conditions will typically depend on the type of microorganism employed, and the skilled art worker will known which cultivation method to choose and how to optimize this method.

The production of OspA or OspB or a part thereof by recombinant techniques has a number of advantages: it is possible to produce OspA or OspB or part thereof by culturing non-pathogenic organisms or other organisms which do not affect the immunological properties of OspA or OspB or part thereof, and it is possible to produce parts of OspA or OspB which may not be isolated from B. burgdorferi strains. High quantities of OspA or OspB or parts thereof may for instance be obtained by using high copy number vectors for cloning the DNA fragment of the invention or by using a strong promoter to induce a higher level of expression than the expression level obtained with the promoters P1 and P2 present on the DNA fragment of the invention. By use of recombinant DNA techniques for producing OspA or OspB or parts thereof, unlimited amounts of a substantially pure protein or polypeptide which is not "contaminated" with other components which are normally present in B. burgdorferi isolates may be obtained. Thus, it is possible to obtain a substantially pure OspA or OspB protein, i.e. OspA or OspB which is not admixed with other B. burgdorferi proteins which have an adverse effect when present in a vaccine or a diagnostic agent in which the OspA or OspB is an intended constituent. A substantially pure OspA or OspB protein or a polypeptide part thereof has the additional advantage that the exact concentration thereof in a given vaccine preparation is known so that an exact dosage may be administered to the individual to be immunized.

Another aspect of the invention are the non-naturally occurring polypeptides encoded by the DNA-sequences in FIG. 3 (corresponding to SEQ. ID. NOS. 4 and 7) for ACA1 and Ip90. Such polypeptides will appear substantially free of peptides with which their natural counterpart would co-occur. In this respect especially lipidated polypeptides are interesting.

Thus, one embodiment of this aspect of the invention relates to a substantially pure polypeptide comprising an amino acid sequence as shown for ACA1 or Ip90 in FIG. 5 (corresponding to SEQ. ID. NOS. 5, 6, 8 and 9, respectively), an antigenic sub-sequence of said amino acid sequence comprising at least one epitope capable of interacting with immunocompetent cells to elicit an immune response against B. burgdorferi, or a polypeptide having a homology of at least about 70% with said amino acid sequence, preferably a homology of at least about 80%, and in particular a homology of at least about 90%. Examples of such substantially pure polypeptides are the amino acid sequences OspA and OspB as shown for ACA1 and Ip90, respectively (corresponding to SEQ. ID. NOS. 5, 6, 8 and 9, respectively), and antigenic sub-sequences thereof. The subsequences will preferably be between 5 and 100 amino acids in length. The subsequences and homologues are typically prepared by recombinant techniques as described above, modifications compared to the sequences illustrated in FIG. 5 suitably being introduced by any of the DNA-modifying techniques described above, such as mutagenesis. Short synthetic polypeptide sequences according to the invention can also be prepared using DNA made by oligonucleotide synthesis, or they can be produced by solid or liquid phase peptide synthesis.

In the present context, the term "polypeptide" is used in its conventional meaning, i.e. as a sequence of amino acids. The amino acids of the sequence may optionally have been modified, after the preparation of the polypeptide, e.g. by chemical, enzymatic or another type of treatment, which does not amend or destroy the immunological activity of the polypeptide to any substantial extent. The polypeptide may be an entire protein, or a subsequence thereof. Especially interesting polypeptides are amino acid sequences comprising epitopes, i.e. antigenic properties of the polypeptide and being capable of evoking an immune response. The minimum amino acid sequence is one which at least comprises a relevant epitope of the polypeptide.

Especially interesting is a substantially pure polypeptide comprising immunogenic fragments able to elicit an immune response against all 3 B. burgdorferi species I, II and III, preferably against the B. burgdorferi strains B31, ACA1, and Ip90.

The antigenicity or immunogenicity of the polypeptides according to the invention can be assessed by usual immunization experiments, using, e.g., rodents such as mice or rabbits as the immunized animal, or using assays, e.g. ELISA, with polyclonal or monoclonal antibodies raised in advance against *B. burgdorferi* or an immunogenic *B. burgdorferi*-related protein or polypeptide.

Methods to obtain specific antibodies against short defined peptides and evaluate their immunogenicity have been described previously. One commonly used strategy is to express the peptide as a fusion protein. There are several advantages to use a fusion system for the production of recombinant peptides. First, heterologous proteins and peptides are often degraded by host proteases; this may be avoided, especially for small peptides, by using a gene fusion expression system. Second, general and efficient purification schemes are established for several fusion partners. The use of a fusion partner as an affinity handle allows rapid recovery of the recombinant peptide. Third, by using different fusion partners, the recombinant product may be localized to different compartments of the host cell or secreted into the culture medium.

There are also several methods described for chemical or enzymatic cleavage of the fusion protein that provide efficient strategies to obtain the desired peptide. Frequently employed fusion systems are the Staphylococcal protein A fusion system and the synthetic ZZ variant which have IgG affinity and have been used for the generation of antibodies against short peptides (Löwenadler et al., 1986 [EMBO J.] 55; 1987 [Gene] 56; 1990 [Eur. J. Immunol.] 57; 1991 [FEMS] 58) the glutathione S-transferase fusion system (Smith and Johnson, 1988 [Gene] 60), the β-galactosidase fusion system (Gray et al., 1982, 54), the trpE fusion system (Yansura, 1990 [Methods Enzym. vol. 185] 61). Several of these systems are commercially available as kits, including vectors, purification components and detailed instructions. In brief, the method to obtain short defined epitopes involves the synthesis of the corresponding oligodeoxynucleotide with appropriate termini to facilitate introduction, in translational frame with the fusion partner, into the desired expression vector.

A substantially pure polypeptide prepared as described above wherein epitopes responsible for evoking autoimmunity in animals, including humans, when administered to the animal have been deleted is a very interesting polypeptide for vaccine purposes.

A particular aspect of the invention relates to synthetic polypeptide fragments at least one amino acid sequence selected from

```
LVSKEKNKDGKYDL   (SEQ.ID.NO. 2, residues 41–54),
LVSKEKDKDGKYSL   (SEQ.ID.NO. 5, residues 41–54),
KGTSDKNNGSGV     (SEQ.ID.NO. 2, residues 64–75),
KGTSDKTNGSGV     (SEQ.ID.NO. 5, residues 64–75),
KGTSDKNNGSGT     (SEQ.ID.NO. 8, residues 64–75),
LEGVKADKSKVKL    (SEQ.ID.NO. 2, residues 76–88),
LEGTKDDKSKAKL    (SEQ.ID.NO. 5, residues 76–88),
LEGEKTDKSKAKL    (SEQ.ID.NO. 8, residues 76–88),
KKVTSKDKSSTEEK   (SEQ.ID.NO. 2, residues 11–125),
RKVSSKDKTSTDEM   (SEQ.ID.NO. 5, residues 112–125),
KKVTLKDKSSTEEK   (SEQ.ID.NO. 8, residues 112–125),
```

-continued
```
KKTKDLVFTKEN     (SEQ.ID.NO. 2, residues 230–241),
KKTTQLVFTKQD     (SEQ.ID.NO. 5, residues 230–241),
RKTKNLVFTKED     (SEQ.ID.NO. 8, residues 231–242),
QYDSNGTKLEGS     (SEQ.ID.NO. 2, residues 247–258),
KYDSAGTNLEGT     (SEQ.ID.NO. 5, residues 247–258),
KYDSAGTNLEGK     (SEQ.ID.NO. 8, residues 248–259),
AVEITKLDEIKNALK  (SEQ.ID.NO. 2, residues 259–273),
AVEIKTLDELKNALK  (SEQ.ID.NO. 5, residues 259–273),
AVEITTLKELKDALK  (SEQ.ID.NO. 8, residues 260–274),
DLNLEDSSKKSHQNAK (SEQ.ID.NO. 3, residues 31–46),
DQEIINSDNTPKDSKK (SEQ.ID.NO. 6, residues 33–48),
DQDVEDLKKDQKDDSK (SEQ.ID.NO. 9, residues 28–43),
KIFVSKEKNSSGK    (SEQ.ID.NO. 3, residues 64–76),
KIFVSKEKNSAGK    (SEQ.ID.NO. 6, residues 66–78),
EIFISKEKNEDDK    (SEQ.ID.NO. 9, residues 61–73),
KPDKSKVKLTVSAD   (SEQ.ID.NO. 3, residues 105–118),
KADKTKVAMTIADD   (SEQ.ID.NO. 6, residues 107–120),
KADKSKVTMLVSDD   (SEQ.ID.NO. 9, residues 102–115),
KKTGKWEDSTSTL    (SEQ.ID.NO. 3, residues 234–246),
KKTATWNETTNTL    (SEQ.ID.NO. 6, residues 237–249),
KKTAVWNDTSSTL    (SEQ.ID.NO. 9, residues 232–244),
KNLSELKNALK      (SEQ.ID.NO. 3, residues 286–296),
KDLAALKAALK      (SEQ.ID.NO. 6, residues 289–299),
```
and
```
KDLEALKAALK      (SEQ.ID.NO. 9, residues 284–294),
``` and polypeptide fragments comprising sequences which are at least 70% homologous, preferably at least 80% homologous, and in particular at least 90% homologous, with any of the above sequences and capable of interacting with immunocompetent cells to elicit an immune response against *B. burgdorferi*, said polypeptide fragment or fragments being smaller in size than naturally occurring OspA or OspB. As mentioned above, computer analysis has indicated that these sequences are of particular value as epitopes. The above sequences comprise sequences derived from the OspA and OspB proteins from B31 in addition to the proteins from ACA1 and Ip90, the first one in each group of two or three sequences being derived from B31, the second from ACA1, and the third from Ip90 (in the case of the first group, there is complete identity between the sequence (the second sequence of the group) derived from ACA1 and the corresponding sequence derived from Ip90).

The abbreviations of the amino acids used herein should be interpreted as follows:

| Amino acid symbol | Three-letter abbreviation | One letter |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A further aspect of the present invention is an antigenic composition comprising, as an antigenic component, a polypeptide encoded by the DNA fragment as defined above or a polypeptide as defined above.

The antigenic composition may comprise a combination of polypeptides encoded from at least two of the OspA genes from B31, ACA1, and Ip90, and/or a combination of polypeptides encoded from at least two of the OspB genes from B31, ACA1, and Ip90, such as a combination of polypeptides encoded from all three of the OspA genes from the three strains mentioned, optionally combined with polypeptides encoded by one, two, or three of the OspB genes from the three strains in question. Such a composition may be useful in generating an immune response against *B. burgdorferi* irrespective of the strain of the *B. burgdorferi* spirochaete.

An example of such a composition is a composition which contains a combination of polypeptides comprising at least one polypeptide fragment selected from

| | | |
|---|---|---|
| LVSKEKNKDGKYDL | (SEQ.ID.NO. 2, residues 41–54), |
| KGTSDKNNGSGV | (SEQ.ID.NO. 2, residues 64–75), |
| LEGVKADKSKVKL | (SEQ.ID.NO. 2, residues 76–88), |
| KKVTSKDKSSTEEK | (SEQ.ID.NO. 2, residues 11–125), |
| KKTKDLVFTKEN | (SEQ.ID.NO. 2, residues 230–241), |
| QYDSNGTKLEGS | (SEQ.ID.NO. 2, residues 247–258), |
| AVEITKLDEIKNALK | (SEQ.ID.NO. 2, residues 259–273), |
| DLNLEDSSKKSHQNAK | (SEQ.ID.NO. 3, residues 31–46), |
| KIFVSKEKNSSGK | (SEQ.ID.NO. 3, residues 64–76), |
| KPDKSKVKLTVSAD | (SEQ.ID.NO. 3, residues 105–118), |
| KKTGKWEDSTSTL | (SEQ.ID.NO. 3, residues 234–246), |
| KNLSELKNALK | (SEQ.ID.NO. 3, residues 286–296) | at least one polypeptide fragment selected from

| | | |
|---|---|---|
| LVSKEKDKDGKYSL | (SEQ.ID.NO. 5, residues 41–54), |
| KGTSDKTNGSGV | (SEQ.ID.NO. 5, residues 64–75), |
| LEGTKDDKSKAKL | (SEQ.ID.NO. 5, residues 76–88), |
| RKVSSKDKTSTDEM | (SEQ.ID.NO. 5, residues 112–125), |
| KKTTQLVFTKQD | (SEQ.ID.NO. 5, residues 230–241), |
| KYDSAGTNLEGT | (SEQ.ID.NO. 5, residues 247–258), |
| AVEIKTLDELKNALK | (SEQ.ID.NO. 5, residues 259–273), |
| DQEIINSDNTPKDSKK | (SEQ.ID.NO. 6, residues 33–48), |
| KIFVSKEKNSAGK | (SEQ.ID.NO. 6, residues 66–78), |
| KADKTKVAMTIADD | (SEQ.ID.NO. 6, residues 107–120), |
| KKTATWNETTNTL | (SEQ.ID.NO. 6, residues 237–249), |
| KDLAALKAALK | (SEQ.ID.NO. 6, residues 289–299), | and at least one polypeptide fragment selected from

| | | |
|---|---|---|
| KGTSDKNNGSGT | (SEQ.ID.NO. 8, residues 64–75), |
| LEGEKTDKSKAKL | (SEQ.ID.NO. 8, residues 76–88), |
| KKVTLKDKSSTEEK | (SEQ.ID.NO. 8, residues 112–125), |
| RKTKNLVFTKED | (SEQ.ID.NO. 8, residues 231–242), |
| KYDSAGTNLEGK | (SEQ.ID.NO. 8, residues 248–259), |
| AVEITTLKELKDALK | (SEQ.ID.NO. 8, residues 260–274), |
| DQDVEDLKKDQKDDSK | (SEQ.ID.NO. 9, residues 28–43), |
| EIFISKEKNEDDK | (SEQ.ID.NO. 9, residues 61–73), |
| KADKSKVTMLVSDD | (SEQ.ID.NO. 9, residues 102–115), |
| KKTAVWNDTSSTL | (SEQ.ID.NO. 9, residues 232–244), |
| KDLEALKAALK | (SEQ.ID.NO. 9, residues 284–294), | or polypeptide fragments comprising sequences which are at least 70% homologous, preferably at least 80% homologous, and in particular at least 90% homologous, with any of the above sequences, the combination being capable of interacting with immunocompetent cells to elicit an immune response against *B. burgdorferi* of any of the strains B31, ACA1, and Ip90, said polypeptide fragment or fragments being smaller in size than naturally occurring OspA or OspB said polypeptide fragments being smaller in size than naturally occurring OspA or OspB, the size here and in the above-discussed contexts typically corresponding to only the amino acid sequences of the sizes as shown or of the same order of sizes.

While the strategy of the above-mentioned composition is to provide an epitope characteristic of each of the strains of *B. burgdorferi,* another important strategy made possible by the present invention is an antigenic composition comprising a polypeptide fragment selected from

| | | |
|---|---|---|
| LVSKEKNKDGKYDL | (SEQ.ID.NO. 2, residues 41–54), |
| LVSKEKDKDGKYSL | (SEQ.ID.NO. 5, residues 41–54), |

```
                    -continued
KGTSDKNNGSGV        (SEQ.ID.NO. 2, residues 64-75), KGTSDKTNGSGV        (SEQ.ID.NO. 5, residues 64-75), and KGTSDKNNGSGT        (SEQ.ID.NO. 8, residues 64-75),
``` or polypeptide fragments comprising sequences which are at least 70% homologous, preferably at least 80% homologous, and in particular at least 90% homologous, with any of the above sequences and capable of interacting with immunocompetent cells to elicit an immune response against *B. burgdorferi* of any of the strains B31, ACA1, and Ip90, said polypeptide fragment or fragments being smaller in size than naturally occurring OspA or OspB, such as discussed above.

As will appear from FIG. 5, there is a very high degree of identity/homology between the sequences shown immediately above in the three strains, and also other regions can be easily identified where there is a high degree of homology, those regions where there is a high degree of homology, e.g. a homology of least 70%, preferably of at least 80%, and in particular at least 90%, and where, at the same time, the homologous polypeptides are immunogenic, such as can be assessed as described above, being candidates for providing single polypeptides which are capable of eliciting a strain-independent immune response against *B. burgdorferi*.

The capability of evoking an immune response against OspA or OspB, and possibly also against immunogenic determinants thereof, is known as described above to be greater if the polypeptide is lipidated. It is therefore also an aspect of the invention that the polypeptides in an antigenic composition for immunizing purposes comprises lipidated polypeptides, especially if the composition is to be used for priming an immune response. In cases where the antigenic composition is to be used for boosting a previously primed immune response non-lipidated polypeptides may be used as well.

A further aspect of the invention is a vaccine for immunizing mammals, including humans, against Lyme disease, the vaccine comprising an antigenic composition as discussed above and optionally an immunogenically acceptable carrier or vehicle.

The carrier or vehicle may be selected from macromolecular carriers such as a polymer, e.g. a polysaccharide or a polypeptide. In addition to the carrier or vehicle, the vaccine may contain an adjuvant, such as Freund's complete or incomplete adjuvant, aluminum hydroxide, a saponin, a muramyl dipeptide, an iscome and an oil, such as a vegetable oil, e.g. peanut oil, or a mineral oil, e.g. silicone oil.

In the vaccine, the immunogenic component(s) may be coupled to a carrier, in particular a macromolecular carrier. The carrier is usually a polymer to which the immunogenic component(s) is/are bound by hydrophobic non-covalent interaction, such as a plastic, e.g. polystyrene, or a polymer to which the immunogenic component(s) is/are covalently bound, such as a polysaccharide, or a polypeptide, e.g. bovine serum albumin, ovalbumin or keyhole limpet hemocyanin. The carrier should preferably be non-toxid and non-allergenic. The immunogenic component(s) may be multivalently coupled to the macromolecular carrier as this provides an increased immunogenicity of the vaccine preparation. It is also contemplated that the immunogenic component(s) may be presented in multivalent form by polymerizing the immunogenic component(s) with itself.

In this regard, it may prove advantageous to couple the immunogenic component to the carrier together with one or more immunologically active molecules obtained from organisms other than *B. burgdorferi* so as to obtain a vaccine comprising a variety of different immunogenic determinants, being a cocktail vaccine, which may be employed for the immunization against diseases caused by other organisms, e.g. organisms responsible for relapsing fever or syphilis.

In another embodiment, a mixture of two or more single vaccines may be employed.

It is known that antibodies raised against *B. burgdorferi* or parts thereof evoking an immune response have a rather short lifetime in sera of animals and humans. Thus, a suitable strategy for immunizing animals and humans against Lyme disease is to periodically administer the vaccine described above to individuals subjected to contact with ticks bearing *B. burgdorferi*, i.e. boost in at regular intervals. It is contemplated that vaccination once a year such as in the springtime will provide a suitable protection of individuals in risk of *B. burgdorferi* infection. A suitable dose of immunogenic components for such a vaccination is 5–500 μg. However, also more irregular immunizations may be advantageous, and any immunization route which may be contemplated or shown to produce an appropriate immune response can be employed in accordance with the principle of the present invention. Suitable administration forms of the vaccine of the invention are oral administration forms, e.g. tablets, granules or capsules, subcataneous, intracutaneous or intramuscular administration forms or forms suitable for nasal or rectal administration.

While the vaccines and compositions discussed above will elicit a humoral immune response, it is possible additionally to evoke a cellular response by incorporating, together with the polypeptide, the carrier, and the optional adjuvant, a peptide expressing a T-cell epitope. If desired, such a T-cell epitope peptide can be bonded to the above-discussed polypeptide by peptide bonds and can be encoded from the same DNA fragment which encodes the above-discussed polypeptide, the DNA fragment having been supplemented with a nucleotide sequence coding for the T-cell epitope peptide.

One interesting method for selecting or developing epitopes eliciting immune responses to *B. burgdorferi* is to utilize a selection pressure invoked by incubation with monoclonal antibodies and investigating sequences of the OspA and OspB proteins of the surviving variants of *B. burgdorferi*. This method is illustrated in Example 6. Epitopes detected by this method is also understood to be within the scope of the present invention.

As stated above, recombinant DNA technologies are useful for the preparation of diagnostic reagents and vaccines. Routine methods for vaccine production involve risks of obtaining unwanted side effects, e.g. due to the vaccine containing unwanted (or even unidentified) contaminants. An alternative approach to the production of new vaccines involves the insertion of one or more DNA sequences constituting one or more parts of the DNA sequence shown in FIG. 5 of parts thereof into a virus genome, e.g. into a retrovirus, vaccinia virus or Epstein-Barr virus genome, to producce a polyvalent vaccine. An especially interesting virus for the present purpose is vaccinia. Also, synthetic polypeptides which have been prepared by conventional methods, e.g. by solid or liquid phase peptide synthesis, are suitable for vaccines.

In a further aspect, the present invention relates to a non-pathogenic microorganism which carries and is capable of expressing an inserted nucleotide sequence which is the nucleotide sequence shown in FIG. 5 or part thereof for use as a live vaccine for the immunization of an animal against Lyme disease. For instance, the use of a live vaccine might be advantageous since it is presume that vaccines based on living organisms show an excellent immunogenicity, and it is also contemplated that the use of a live vaccine will confer a life-long immunity against Lyme disease so that repeated vaccination will not be needed.

In a particularly advantageous embodiment of the live vaccine of the invention, the DNA fragment of the invention is expressed on the outer surface of the host microorganism. This provides a favourable presentation of the immunologically active part(s) or OspA recognized by the immune defense mechanisms of the animal to which the live vaccine is administered, thus provoking an appropriate immune response. One way of providing the expression of OspA or immunologically active part(s) thereof (the epitopes) on the cell surface is to fuse the DNA fragment of the invention to another nucleotide sequence encoding a surface protein or a subsequence thereof (e.g. a signal peptide) which cause the *B. burgdorferi* epitopes to be expressed on the outer surface of the host cell, optionally as a fused polypeptide. Examples of useful surface proteins are adhesins, fimbrial proteins, or other extracellular proteins.

The microorganism used for live vaccines should be a non-pathogenic microorganism, e.g. a non-pathogenic *E. coli,* which may be able to establish itself in the animal body. A microorganism which may prove especially useful as a live vaccine may be the *B. burgdorferi* in itself, which as explained above inherently expresses OspA on the surface of the cell. The use of *B. burgdorferi* for a live vaccine requires, however, that the *B. burgdorferi* has been altered so as to not cause any illness when used as a live vaccine. This alteration or modification may be carried out in any suitable manner, e.g. by mutagenization, chemical, enzymatic or heat treatment, or by another equivalent treatment resulting in an attenuated *B. burgdorferi* cell.

In order to increase the production of lipidated recombinant *Borrelia burgdorferi* outer surface protein, OspA, in *E. coli,* a specially designed expression system has been developed.

The results obtained by using the original OspA signal peptide in different *E. coli* expression vectors have demonstrated that the signal peptide cleavage site is recognized. Furthermore, the processed OspA molecules are also lipidated, demonstrated by $^3$H-palmitic acid labelling and protein characterization. However, the level of production is relatively low.

To improve productivity and facilitate signal peptide cleavage and lipidation, the sequence encoding the full-length OspA protein is combined with the amino-terminal cysteine residue with an *E. coli* derived signal sequence. Since it is well known that the signal peptidase II recognizes certain signal peptides and is also responsible for lipidation of pre-proteins harbouring such a sequence, it is reasonable to assume the advantage of using a homologous sequence. The resulting recombinant open reading frame is then to be inserted under control of a strong promoter.

A further aspect of the present invention is a method of producing a polypeptide as defined above comprising
  inserting a DNA fragment as defined above in a vector which is able to replicate in a specific host cell,
  introducing the resulting recombinant vector into the specific host cell,
  growing the host cell under appropriate culture conditions for expression of the polypeptide, and
  recovering the polypeptide,
optionally followed by purification.

Preferably, the host cell is capable of expressing lipidated polypeptides, such as is the case when the host cell is *E. coli.*
Hybridization of DNA DNA, e.g. present on nitrocellulose filters, are wetted in 2×SSC [1×SSC; 0.15 M NaCl, 0.0015 M Na$_3$-citrate, pH 7.0] and placed in a heat-sealed plastic bag with prewarmed 67° C.) prehybridization solution. Prehybridization takes place for 2 h at 67° C., the bag being gently shaken. The solution is exchanged with prewarmed (67° C.) hybridization solution, the radioactive probe is added and hybridization is carried out at 67° C. for 18 h. The bag is gently shaken to ensure constant movement of the liquid over the nitrocellulose filters. After hybridization, a washing procedure is carried out.

The radioactive probe is prepared by use of known methods, e.g. as described by Sambrook et al., on the basis of the DNA sequence shown in Sequence Listing 1 or a part thereof, especially a coding part such as the nucleotides corresponding to amino acids 1–210 or an effective subsequence of the DNA sequence as defined above.

The prehybridization and hybridization solutions used are: 10×Denhardt's, 4×SSC, 0.1% SDS, 10 μg/ml polyA, 50 μg/ml of denatured DNA to be analysed and the denatured (heat) radioactive probe. The filters are washed in prewarmed (67° C.) solutions: 10×Denhardt, 2×SSC, 0.1% SDS for 2×15 min. and 1×SSC, 0.1% SDS for 4×15 min. The filters are air-dried and covered with Vita-Wrap, and X-ray film is exposed to the filters for 3 h to 3 weeks with and without intensifying screens.

EXAMPLE 1

Isolation and Sequence Analysis of the OspA and OspB Genes

Bacterial Strains

The *Borrelia burgdorferi* strains used were the American reference strain B31 (ATCC 35210), the Swedish isolate ACAI isolated from a patient with acrodermatitis chronicum migrans (1), and the Ip90 strain which is isolated from *I. persulcatus* from the Soviet union and was kindly provided by E. I. Korenberg and V. N. Kryuchechnikov of the Gamaleya Institute, Moscow (27).

Media and Culturing Conditions

The *B. burgdorferi* strains were cultivated in BSK II medium as previously described (2).

The *Escherichia coli* strains DH5α (BRL, Gaithersburg, Md. USA) and Y1090 (24) were used for propagation of recombinant plasmids and for growth of λgt11 phage gene library, respectively.

Construction and Screening of λ-gt11 and pUC18 Plasmid *B. burgdorferi* Gene Libraries

*B. burgdorferi* strains were cultured in 400 ml modified BSKII-medium (2) at 34° C. and harvested at late mid-log phase. The DNA was extracted and purified as previously described (23). The ACAI DNA was partially digested by Sau3AI and fragments 4–8 kb in size were isolated from a 0.7% agarose gel. The fragments were then ligated into BamHI-cut λ-gt11 arms and packaged into phage beads as described by the vendor (SDS-Promega, Falkenberg, Sweden). The λ-phages were propagated in *E. coli* Y 1090 and screening, by DNA hybridization, of the λ-library was according to standard methods (24). The oligonucleotides used for screening, J1, J2, and J3, were synthesized from the previously published *B. burgdorferi* B31 osp-operon nucleotide sequence (14). All nucleotides used for screening of phage and plasmid libraries and primers for nucleotide sequencing are shown in Table 1. The oligonucleotides were end labelled with $^{32}$P-γ-dTAP, as previously described (31), and purified on a Sephadex G-50 (Pharmacia, Uppsala, Sweden) spin column. The hybridization was performed at 37° C., i.e. medium strigency, as some differences in the nucleotide sequence between the different strains could be expected. The phage DNA was extracted as previously described (28). Purified λ-DNA was further subcloned into the EcoR1 site of pUC18 according to standard methods (30).

A plasmid gene library of *B. burgdorferi* Ip90 DNA was constructed by partial Hind III digestion of total DNA, in which 1 u enzyme was incubated with 100 ng DNA at 37° C. for 15 min. The reaction was terminated by a phenol:chloroform (1:1) extraction. After ethanol precipitation, the fragments were ligated with 30 ng HindIII digested pUC18 plasmid DNA at 16° C. for 4 h. The plasmid were transformed into competent *E. coli* DH5α cells. An additional plasmid gene library was constructed by complete EcoRI digestion of IP90 DNA and cloning into the EcoRI site of the plasmid pUC18.

The *B. burgdorferi* Ip90 plasmid gene library was screened with a 259 bp osp-fragment. This ospA fragment was obtained by PCR amplification of a DNA segment located at the end of the ospA gene, using the J1 and K1 oligonucletides as primers (Table 1). This fragment corresponds to a fragment between nucleotide positions 529 to 788 of the *B. burgdorferi* B31 ospA gene. The conditions for the PCR amplification were as follows; 16.6 mM $(NH_4)SO_4$, 67 mM Tris-HCl (pH 8.8 at 25° C.), 6.7 mM $MgCl_2$, 10 mM 2-mercaptoethanol, 200 μM each of dATP, dGTP, dCTP, and dTTP, 170 μg per ml bovine serum albumin, 5 pmol of each primer, about 10 pg total Ip90 DNA and 1 u of Biolabs Taq polymerase. Reactions were performed in a volume of 50 Ml, overlaid with 40 Ml of mineral oil. During the first 5 cycles, denaturation was done at 94° C. for 2 min, annealing at 45° C. for 1 min and elongation at 72° C. for 1 min. In the next 30 cycles, the denaturation time was shortened to 39 sec and annealing temperature raised to 55° C., otherwise the conditions were the same. The PCR fragments was labelled with $^{32}P$-α-dATP using an oligo-labelling kit (Amersham, Buckinghamshire, UK) and used to screen the HindIII library for osp-gene containing clones. The screening was performed as described (30), and the hybridization was performed at high stringency (60° C.).

Nucleotide Sequence Analysis

Deletion libraries in one direction were constructed for the full length clone of ACAI and the shorter or the Ip90 clones as described earlier (21). Mini plasmid preparations were either performed according to the boiling method (30) or by a CsCl method previously described (39). Nucleotide sequencing was performed using the dideoxy chain-termination method described by Sanger et al. with the use of Pharmacia $^{T7}$Sequencing™ kit (Pharmacia, Uppsala, Sweden). The complete sequence for both strands was determined. From the nucleotide sequences obtained, internal primers were synthesized to enable sequencing of the other strand plus the beginning of the Ip90 osp-operon. The sequences obtained from the DNA deletion sequencing method were assembled using the GENEUS (20) software for VAX computers (Digital Equipment Corporation). Additional nucleotide sequence analyses were performed using the University of Wisconsin GCG Sequence Analysis software for the VAX computer, and PC-Gene (Genofit) for the personal computers.

In Vitro Transcription Analysis

Transcriptional analysis was performed on total mRNA isolated form *B. burgdorferi* B31 using a method previously described (31). The isolated and purified mRNA was subjected to primer extension in an in vitro reaction using Avian myeloblastosis virus reverse transcriptase (Lief Sciences, Fla. USA) as described previously with minor modifications (13, 17, 48). The primer extension reaction with RNA was carried out with $[α-^{32}P]$-dATP. The primer used in the primer extension reaction was the reverse complement of nucleotides 128 to 160 in FIG. (3). Only full-length mRNA polymer was synthesized, the size of the transcript was compared with a regular Sanger dideoxy DNA sequence on plasmid pTHR44 obtained when using the same oligonucleotide primer. In the DNA sequencing reactions $[α-^{35}S]$-dATP was used.

EXAMPLE 2

Cloning and Nucleotide Sequence Analysis of Osp-Operons from *B. burgdorferi* Isolates ACAI and Ip90

Sequencing Analysis

The osp-operons from the Swedish *B. burgdorferi* strain ACAI was isolated from a λgt11 library. The isolation of the ACAI osp-operon was performed by screening with a mixture of three oligonucleotides, J1, J2 and J3, which were synthesized from the nucleotide sequence of the previously published *B. burgdorferi* B31 osp-operon. One positive λ-clone containing the ACAI ospA and ospB genes was isolated and characterized by restriction endonuclease mapping. The isolated osp operon was subcloned into pUC18 and the genetic organization of the genes was confirmed with the same three oligonucleotides, J1, J2, and J3. The osp-operon of strain Ip90 was cloned for a pUC18 plasmid library using Hind III, partially digested, total Ip90 *B. burgdorferi* DNA. One positive clone containing almost the entire Ip90 osp-operon except the first 175 bp of ospA was obtained. An oligonucleotide, J4, was constructed from the start of this Hind III clone. This oligonucleotide, J4, was used to pick up a clone containing the whole Ip90 osp-operon from a pUC18 plasmid library of completely EcoRI digested Ip90 DNA.

The osp-operons were sequenced and their nucleotide sequences of the osp-operons of strains ACAI and Ip90 are shown in FIG. 3. The obtained nucleotide sequences are, in the Figure, aligned and compared to the previously published nucleotide sequences of the ospA and ospB genes of strain B31 (14) and the ospA sequences from the strains Z57 (SEQ ID NO:13) (45) and N40 (SEQ ID NO:11) (19). The percentage DNA identity of the respective ospA and ospB genes are shown in Table 2 and 3. The results of the nucleotide sequence comparison revealed that the ospA genes from strains ACAI and Ip90 exhibited a sequence identity of 85% with the ospA genes of strain B31. When compared to each other, the ospA genes of ACAI and Ip90 also showed an 85% similarity. In contrast, the two previously published ospA sequences from strains ZS7 (SEQ ID NO:12) and N40 (SEQ ID NO:10) were almost identical to the ospA sequence of strain B31 (>99%). The ospB sequences of strain ACAI and Ip90 were 79% identical to the ospB gene of strain B31 and 81% identical compared to each other. Further analysis of the osp-genes of strain ACAI and Ip90 revealed that ospA and ospB genes are organized in one operon, separated by just a few basepairs. The osp-operons in these two strains are also preceded by a control region consisting of a σ-70 promotor and a Shine and Dalgarno ribosomal binding site, as depicted in FIG. 3 (37). In order to determine the exact transcriptional start point of the osp-operon, an in vitro primer extension was performed on isolated total messenger RNA from *B. burgdorferi* B31 (FIG. 4). The in vitro transcription analysis identified the transcriptional start site as the G at position +1 (FIG. 3). This transcriptional start site is situated 36 bp upstream of the AUG translational start codon.

EXAMPLE 3
Sequence Analysis of the Translated OspA and OspB Proteins of Strains ACAI and Ip90.

The translated products of the ospA genes of ACA1 and Ip90 were compared with the deduced translation products of strains B31, ZS7, and N40. The comparison of the different OspA proteins in an optimal alignment are shown in FIG. 5A. The deduced OspA protein for ACA1 is 273 amino acids long with a theoretical molecular weight of 29,629 and for Ip90 it is 274 amino acids long predicting a protein with a molecular weight 29,673. The three different ospB gene products are compared in FIG. 5B. The deduced OspB proteins have a molecular weight of 32,432 coded by 299 amino acids for ACA1, and 32,105 coded by 294 amino acids for Ip90. From the amino acid sequence comparison of the OspA and OspB proteins it is evident that the start of the OspA is very conserved between the different strains, while the middle and the C-terminal parts of the proteins show a higher degree of variation. In the OspB protein the same overall variability in the sequence is seen. From the deduced amino acid sequence of the OspA and OspB proteins of *B. burgdorferi* strain B31 the sequence similarity with a prokaryotic lipoproteins was shown (14). The deduced OspA and OspB proteins of *B. burgdorferi* strains ACA1 and Ip90 also contain the typical consensus tetrapeptide (LXYC) in their peptides. The possible signal peptidase II recognition sites of the OspA and OspB proteins are indicated in the FIGS. (5A and 5B).

EXAMPLE 4
Extraction of *B. burgdorferi* proteins, SDS-PAGE, and Western blotting.

The cells were grown in 200 ml at 34° C. and harvested in mid-log phase (approximately 2 to $4 \times 10^8$ cells per ml) by centrifugation at 8,000 g for 20 min. The cells were washed twice in PBS-5 mM $MgCl_2$, and the pellets were resuspended in 2 ml PBS. To prepare soluble proteins, the cells were sonicated 4 times 30 sec in an ice bath by using a Branson Sonifer cell disrupter B15 at setting 3. After centrifugation at 10,000 g for 30 min, the supernatant was collected and the amount of protein was determined by using the Bio-Rad protein assay (Bio-Rad, Munich, Germany).

SDS-PAGE was performed essentially as described before (10) using either 12.5% or 15% acrylamide running gels and 4% acrylamide stacking gels. In each lane 10 to 15 µg protein was added. The gels were either fixed and stained by Coomassie brilliant blue (Sigma chemical, Saint Louis, Mo., USA) or processed for immunoblotting. Molecular weight standards were obtained from Pharmacia (Uppsala, Sweden) and included proteins ranging from 14.4 to 94 kDa. The proteins were transferred to immobilon filters (Millipore Corporation, Bedford, Calif., USA) by electroblotting at 0.8 mA over $cm^2$ for 45 min. The non-specific binding on the filters was blocked by incubation with 5% milk powder in PBS over night. The filters were then incubated with antibodies (1:20 or 1:25 dilution in 2.5% milk powder in PBS), washed 3 times 5 min in PBS-0.5% Tween 20 and then incubated with an appropriate peroxidase labeled monoclonal antibody, Mab (1:500 dilution in 2.5% milk/PBS) for 1 hour. Bound antibodies were then visualized by adding 5-bromo-4-chloro-3-indolylphosphate as peroxidase substrate. All incubations were performed during continuous shaking. The Mab's used were the anti-OspA antibodies H5332 (10) and the H3TS (7) and the anti-OspB antibody H6831 (9). A polyclonal antisera raised against whole cell lysates form the Swedish *B. burgdorferi* tick isolate G152 (44), a gift from Mats Karlsson, Danderyd hospital, Stockholm, Sweden, was used in Western blotting to show the presence of *B. burgdorferi* major outer surface proteins.

EXAMPLE 5
Biochemical and Immunochemical Characterization of the OspA and OspB Proteins of *B. burgdorferi* Strains ACA1 and Ip90.

Whole cell protein extracts prepared form *B. burgdorferi* strains B31, ACA1 and Ip90 separated on a 12,5% SDS-PAGE are shown in FIG. 1. These three different *B. burgdorferi* isolates were obtained from different geographical locations. The three strains show different apparent molecular weights for both the major outer surface proteins OspA and OspB. This result was also found earlier, when comparing the strain B31 and ACA1 (8). The molecular weights of the respective OspA and OspB proteins as determined from the SDS-PAGE are as follows: for B31; 31 kD and 34 kD, for ACA1; 32 kD and 36 kD, and for Ip90; 33,5 kD and 34 kD. The Osp proteins from the three different isolates were further characterized by western blot analysis using different monoclonal antibodies directed against the OspA and OspB proteins of *B. burgdorferi* B31. In a western blot using the OspA specific MAb H5332 (FIG. 2A), a protein extract form strain B31 strongly bound to this antibody, whereas the ACA1 OspA protein only reacted weakly. No protein from strain Ip90 reacted with the MAb H5332. When the OspA specific MAb H3TS (FIG. 2B) or OspB specific MAb H6831 (FIG. 2C) was used only the OspA and OspB proteins of strain B31 reacted, the Osp proteins of ACA1 and Ip90 did not react with these two monoclonal antibodies indicating a variability of the OspA and OspB proteins in these three strains. When using a polvalent polyclonal antisera raised against whole cell *B. burgdorferi* (FIG. 2D), all three strains reacted with 10 to 15 different proteins. In all strains the strongest hybridization signal was against a protein of the size of the OspA protein. The apparent molecular weights of these presumed OspA proteins are, as calculated from the western blot, 31 kD (B31), 32 kD (ACA1), and 33.5 kD (Ip90), respectively.

EXAMPLE 6
Identification of Epitopes

Materials

*B. burgdorferi* organism of the strains B31, ACA1 and Ip90

Monoclonal antibodies directed to OspA and OspB, H5332 and H3TS, respectively.

Methods

Incubating *B. burgdorferi* in the presence of one of the monoclonal antibodies at 34° C. in BSKII broth culture medium, the growth of the spirochates is inhibited. After 1–7 days variants which are not inhibited by the antibody begin to grow. These antibody-resistant organisms have changes in the OspA or OspB protein. They are mutants selected with monoclonal antibodies.

The epitopes against which the growth-inhibiting antibodies are directed will be identified by comparing the deduced amino acid sequence of the original strain with the deduced amino acid sequence of the mutant.

The deduced amino acid of the mutant OspA proteins will be determined by DNA sequencing of amplified DNA from the polymerase chain reaction.

EXAMPLE 7

Preparation and Evaluation of Epitopes

Epitopes are prepared as fusion proteins by using a gene fusion expression system making fusion partners. A fusion partner may be used as an affinity handle which allows rapid recovery of the recombinant peptide. By using different fusion partners, the recombinant product may be localized to different compartments of the host cell or secreted into the culture medium.

The following epitope is prepared LVSKEKNKDGKYDL (SEQ. ID. NO. 2, residues 41–54), by using the following oligodeoxynucleotide sequences: 5'-AATTCGTTAGTATCTAAAGAAAAAACAAGATGGAAAATATGATTGA-3' (SEQ. ID. NO. 14) and 5'-AGCTTCAATCATATTTTCCATCTTTGTTTTTTTCTTTAGATACTAACG-3'(SEQ. ID. NO. 15) The oligodeoxynucleotide sequences are synthesized by machine and annealed. The addition of nucleotides at both termini to get EcoRI and HindIII compatible ends, respectively, is to facilitate cloning of the fragment in translational frame into a fusion system expression vector. In this experiment, the commercially available system pEZZ18, based on the synthetic dimer of the Staphylococcal protein A IgG binding domain, ZZ (Löwenadler et al., 1987 [Gene]), under control of the protein A promoter and signal sequence (Pharmacia) is used. The vector plasmid pEZZ18, which contains a multiple cloning site downstream of the ZZ fragment, is digested with EcoRI and HindIII and the 4.6 kb fragment is isolated. The linearized pEZZ18 plasmid element is then ligated with the annealed synthetic oligonucleotides described above. *E. coli* strain TG2 is transformed, single colonies are isolated, and plasmids are prepared for sequence analysis. Plasmids containing the desired sequence are then transformed into TG2 and DH5α for expression studies. Bacterial cultures are grown in standard LB medium containing 50 μg/ml of ampicillin or carbenicillin. Overnight cultures are harvested by centrifugation and the localization of the recombinant peptide in culture medium, periplasm or cytoplasm is analyzed by fractionation and Western blot experiments. The fraction(s) containing the recombinant fusion protein including the desired peptide is/are then passed over an IgG sepharose, 6FF, column (Pharmacia) for binding of the fusion protein. The column is then extensively washed and the recombinant fusion protein is eluted according to the vendor's instructions (Pharmacia). The column is equilibrated with 2–3 bed volumes of 0.5 M HAc pH 3.4, and with 50 mM Tris-HCl pH 7.6, 150 mM NaCl, 0.05% Tween 20 (TST). The neutral pH is checked before the sample is applied. The sample is applied and the column is washed with 10 bed volumes of TST and bed volumes 5 mM $NH_4Ac$ pH 5.0. The fusion protein is then eluted with 0.5 HAc pH 3.4.

There are options available to localize the fusion partner at either the amino terminal or at the carboxy terminal, or at both. This can be of advantage when specific modifications are desired, for example lipidation of a cysteine localized at the amino terminal.

The recombinant peptide is then generally purified by affinity chromatography, using the fusion partner as a handle (see references above).

Suitable animals are then immunized with the peptide, optionally together with an adjuvant. Sera are collected and evaluated for reactivity against the native protein in an immunoassay, e.g. Western blot or in an in vitro assay, e.g. growth inhibition studies.

EXAMPLE 8
Expression of Recombinant OspA Lipo-Protein in *Escherichia coli*

In order to increase the production of lipidated recombinant *Borrelia burgdorferi* outer surface protein, OspA, in *E. coli*, a specially designed expression system has been developed which produces lipidated OspA in *E. coli*.
Method Two PCR primers, SYM 2692 (5'-GCGAATTCGCGGCCGCTGGCTCTGCAGAGCAATCTG-3', SEQ. ID. NO. 16) and SYM 2693 (5'-GCGGATCCGCTAGCAGAGTAGAACCCAGGATTAC-3', SEQ. ID. NO. 17), were synthesized. These primers were used to amplify a fragment containing the hybrid LPP and lac promoter together with the major part of the LPP signal sequence from the plasmid pKEN125, cf. Nakamura et al. 1979 (64). LLP is the gene coding for outer membrane lipoprotein of *E. coli* (Nakamura et al., 1982) (63). The resulting PCR fragment was digested with PstI and NheI and isolated by agarose electrophoresis.

To amplify the rest of the LPP signal sequence in frame with the 5'-end of the OspA sequence, another PCR was performed. The set of primers used in this reaction was SYM 2695 (5'-GCGAATTCGCTAGCAGGTTGTAAGCAAATGTTAGCAG-3', SEQ. ID. NO. 18) and SYM 1983 (5'-TCAAGCTTGTCTACTGTTGC-3', SEQ. ID. NO. 19), cf. Nakamura et al. 1979 (64). The amplified fragment was digested with EcoRI and HindIII and isolated as above. This fragment was then ligated with a 645 bp long HindIII and BamHI fragment containing the rest of the OspA encoding sequence and with BamHI and EcoRI digested pUC19, and the resulting plasmid was sequenced and designated pS324.

The plasmid pS324 was then digested with NheI and BamHI, and a 784 bp fragment containing the entire OspA encoding sequence and the sequence encoding the three amino acids from the LPP signal sequence located adjacent to the OspA sequence was isolated by agarose electrophoresis. In the next step, this 784 bp fragment was ligated with the PstI and NheI PCR fragment containing the promoter sequence and the 5'-part of the signal sequence and cloned into PstI and BamHI digested pUC19. This expression construct was designated pS420.
Expression To analyze expression directed by this construct, pS420, two *E. coli* strains were tested, DH5α and TG2.
DH5α
Genotype
supE44 ΔlacU169(Φ801acZΔM15)
hsd R17 recA1 endA1 gyrA96 thi-1 re1A1

The Φ801acZΔM15 permits α-complementation with the amino terminus of β-galactosidase encoded in pUC vectors. DH5α is available from Bethesda Research Laboratories Inc. (Hanahan D. (1983) J. Mol. Biol. 166:557.
TG 2
Genotype
supE hsdΔ5 thi Δ(lac-proAB)
Δ(sr1-recA)306 Tn10 (tet$^r$)
FÙ[traD36 proAB+lac19 lacZΔM15]

A recombination-deficient derivative of TG1. (Sambrook (1989)).

Both strain were obtained from Department of Microbiology, University of Umeå.

Typical for in vivo labelling studies, the expression experiments were carried out as follows. Liquid cultures, in LB containing 50 μg/ml of carbenicillin, of pS420 transformed DH5α and TG2, were inoculated and incubated at 37° C. for approximately 7 hours. From these cultures, 100 μl of culture was inoculated to 1 ml of LB containing 50 μg/ml carbenicillin, 50 μl of [9,10(n)-$^3$H] palmitic acid (Amersham) with a specific activity of 54.6 Ci/mmol and a radioactive concentration of 1 mCi/ml, and 2 mM IPTG. This culture was grown overnight at 37° C. As controls the *E. coli* host strains without expression vector, and the same strains with the pS151 vector were used. The culture conditions were identical except that carbenicillin was omitted from the non-plasmid containing cultures. pS151 is identical to pTRH44 (Bergström et al., 1989, (13)). Results shown in FIGS. 6A and B.

For expression analysis, 1 ml of bacterial culture was harvested and the cells were pelleted by centrifugation. The resulting pellets were dissolved by boiling for 10 minutes in 50 μl of sample buffer (Laemmli, 1970). Samples were analyzed by SDS-PAGE and immunoblotting and autoradiography, respectively. To culture larger volumes, the same procedure was followed except that the radioactive tracer was omitted.

Conclusion

Analysis by SDS-PAGE and immunoblotting with the OspA monoclonal antibody H5332, in vivo labelling studies with $^3$H-palmitic acid, and purification of recombinant OspA have demonstrated highly efficient expression of lipidated processed OspA in E. coli.

TABLE 3

DNA sequence identity (percent) between the ospB genes from different Borrelia burgdorferi isolates.

|  | B31 | ACA1 | IP90 |
|---|---|---|---|
| B31 | * |  |  |
| ACA1 | 79 | * |  |
| IP90 | 79 | 81 | * |

REFERENCES

1. Åsbrink, E. & A. Hovmark. 1985. Successful cultivation of spirochetes from skin lesions of patients with erythema chronicum migans Afzelius and acrodermatitis chronica strophicans. Acta. Path. Microbiol. Immunol. Scand. Sect. B, 93: 161–163.

2. Barbour, A. G. 1984. Isolation and cultivation of Lyme disease spirochetes. Yale J. Biol. Med. 57: 71–75.

3. Barbour, A. G. 1984. Immunochemical analysis of Lyme disease spirochetes. Yale J. Biol. Med. 57: 581–586.

4. Barbour, A. G. 1988. Plasmid Analysis of Borrelia burgdorferi, the Lyme Disease Agent. Journal of Clinical Microbiology 26: 475–478.

5. Barbour, A. G. 1989. Antigenic variation in relapsing fever Borrelia species: genetic aspects. In Berg, D. E. & Howe, M. M. (eds): Mobile DNA, Washington, D.C. American Society for Microbiology, pp. 783–789.

6. Barbour, A. G. & C. F. Garon. 1987. Linear plasmids of the bacterium Borrelia burgdorferi have covalently closed ends. Science 237: 409–411.

TABLE 1

Oligonucleotides used for screening of phage and plasmid gene libraries, nucleotide sequencing of the osp-operons, and primer extension analysis.

| Oligomer | Origin | Position* | Sequence 5' to 3' | | |
|---|---|---|---|---|---|
| J1 | B31 | 788–760 | TTTGAGTCGTATTGTTGTACTGTAATTGT | SEQ ID NO. 1: | K 842–870 |
| K1 | B31 | 529–556 | TATGTTCTTGAAGGAACTCTAACTGCTG | SEQ ID NO. 1: | 611–637 |
| J2 | B31 | 337–312 | GTGTGGTTTGACCTAGATCGT | SEQ ID NO. 1: | K 393–413 |
| J3 | B31 | 1237–1217 | AGGTTACTGTGTTTAAATCAG | SEQ ID NO. 1: | K 1299–1319 |
| P1 | pUC19 | 334–317 | ACGCCAGGGTTTTCCCAG | SEQ ID NO. 20 | |
| P2 | pUC19 | 172–189 | GTGTGGAATTGTGAGCGG | SEQ ID NO. 21 | |
| I1 | Ip90 | 278–256 | GTTTTTTCACCTTCAAGTGTTCC | SEQ ID NO. 7: | K 344–365 |
| B1 | B31 | -67–(-48) | TTATTATCATTTTATTTTTTTT | SEQ ID NO. 1: | 15–36 |
| B2 | B31 | 75–54 | GGCTAATATTAGACCTATTCCC | SEQ ID NO. 1: | K 136–157 |
| B3 | B31 | 1084–1066 | ATTTTTTTCTTTGCTTAC | SEQ ID NO. 1: | K 242–259 |
| B4 | B31 | 1066–1084 | GTAAGCAAAGAAAAAAAT | SEQ ID NO. 1: | 242–259 |
| B5 | B31 | 1425–1407 | TAGAGTTTCTACTGCTTTT | SEQ ID NO. 1: | K 1486–1505 |
| B6 | B31 | 1407–1425 | TACAAAAGCAGTAGAAACTC | SEQ ID NO. 1: | 1486–1505 |
| B7 | B31 | 1603–1622 | TTAACAATTAGTGCTGACAG | SEQ ID NO. 1: | 1685–1704 |
| B8 | B31 | 1642–1661 | GTGTTCTTAACAGATGGTAC | SEQ ID NO. 1: | 1724–1741 |
| B9 | B31 | 1661–1642 | GTACCATCTGTTAAGAACAC | SEQ ID NO. 1: | K 1724–1741 |
| B10 | B31 | 160–128 | CAAGAACTTTCATTTCACCAGGCAAATCTACTG | SEQ ID NO. 1: | K 210–242 |
| A1 | ACA1 | 140–120 | GGCAAATCTACTGAAGCGCTG | SEQ ID NO. 4: | K 210–230 |
| A2 | ACA1 | 202–223 | GCAACAGTAGACAAGATTGAGCT | SEQ ID NO. 4: | 293–314 |
| A3 | ACA1 | 452–472 | GAGAAAATGGAACCAAACTTG | SEQ ID NO. 4: | 543–563 |
| A4 | ACA1 | 525–502 | TTTTAAAACTTCTTTAGCTTTTCC | SEQ ID NO. 4: | K 593–616 |
| A5 | ACA1 | 669–689 | AAAAACTGGCGCATGGGATTC | SEQ ID NO. 4: | 770–790 |
| A6 | ACA1 | 840–821 | AAGTTCATCAAGTGTTTTAA | SEQ ID NO. 4: | K 912–931 |
| A7 | ACA1 | 968–992 | TATAAACTCAGACAATACACC | SEQ ID NO. 4: | 1059–1083 |
| A8 | ACA1 | 1176–1156 | ACCTTCAAGCTTGCCAGATCC | SEQ ID NO. 4: | K 1247–1267 |
| A9 | ACA1 | 1291–1313 | CAAGGGTCAGTAATAAAAGAATC | SEQ ID NO. 4: | 1382–1401 |
| A10 | ACA1 | 1802–1779 | CCTACAAAGGTATTAGCCGA | SEQ ID NO. 4: | K 1870–1893 |

*All possitions are derived from the B. burgdorferi B31 ospA and ospB sequence in FIG. 3. except for the pUC19 sequences, which are derived from the EMBL data base sequences of pUC19 plasmid.
K = complementary to

TABLE 2

DNA sequence identity (percent) between the ospA genes from different Borrelia burgdorferi isolates.

|  | B31 | N40 | ZS7 | ACA1 | IP90 |
|---|---|---|---|---|---|
| B31 | * |  |  |  |  |
| N40 | 99.8 | * |  |  |  |
| ZS7 | 99.5 | 99.8 | * |  |  |
| ACA1 | 85 | 85 | 85 | * |  |
| IP90 | 86 | 86 | 85 | 86 | * |

7. Barbour, A. G., R. A. Heiland & T. R. Howe. 1985. Heterogeneity of major proteins in Lyme disease borreliae: a mMolecular analysis of North American and European isolates. J. Infect. Dis. 152: 478–484.

8. Barbour, A. G. & M. E. Schrumpf. 1986. Polymorphism of major surface proteins of *Borrelia burgdorferi*. Zentralbl. Bakteriol. Parasitenkd. Infektionskr. Hyg. Abt. 1 Orig. Reihe A. 263: 83–91.

9. Barbour, A. G., S. L. Tessier & S. F. Hayes. 1984. Variation in a major surface protein of Lyme disease spirochetes. Infect. Immun. 45: 94–100.

10. Barbour, A. G., S. L. Tessier & W. J. Todd. 1983. Lyme disease spirochetes and Ixodes ticks share a common surface antigenic determinant defined by a monoclonal antibody. Infect. Immun. 41: 795–804.

11. Barbour, A. G., N. Burman, C. J. Carter, T. Kitten & S. Bergström. 1991. Variable antigen genes of the relapsing fever agent *Borrelia hermsii* are activated by promoter addition, Mol. Microbiol. 5: 489–493.

12. Barbour, A. G., C. J. Carter, N. Burman, C. S. Freitag, C. F. Garon & S. Bergström. 1991. Tandem insertion sequence-like elements define the expression site for variable antigen genes of *Borrelia hermsii*. Infect. Immun. 59: 390–397.

13. Bergström, S., K. Robbins, M. Koomey & J. Swanson. 1986. Piliation control mechanisms in *Neisseria gonorrhoeae*. Proc. Natl. Acad. Sci. USA 83: 479–486.

14. Bergström, S., V. G. Bundoc & A. G. Barbour. 1989. Molecular analysis of linear plasmid-encoded major surface proteins, OspA and OspB, of the Lyme disease spirochete *Borrelia burgdorferi*. Mol. Microbiol. 3: 479–486.

15. Brandt, M. E., B. S. Riley, J. D. Radolf & M. V. Norgard. 1990. Immunogenic integral membrane proteins of *Borrelia burgdorferi* are lipoproteins. Infec. Immun. 58: 983–991.

16. Bundoc, V. G. & A. G. Barbour. 1989. Clondal polymorphism of outer membrane protein OspB of *Borrelia burgdorferi*. Infect. Immun. 57: 2733–2741.

17. Burman, N., S. Bergström, B. I. Restrepo & A. G. Barbour. 1990. The variable antigens Vmp7 and Vmp21 of the relapsing fever bacterium *Borrelia hermsii* are structurally analogous to the VSG proteins of the African trypanosome, Mol. Microbiol. 4: 1715–1726.

18. Craft, J. E., D. K. Fischer, G. T. Shimamoto & A. C. Steere. 1986. Antigens of *Borrelia burgdorferi* recognized during Lyme disease. Appearance of a new IgM response and expansion of the IgG response late in illness. J. Clin. Invest. 78: 934–939.

19. Fikrig, E., S. W. Barthold, F. S. Kantor & R. A. Flavell. 1990. Protection of mice against the Lyme disease agent by immunizing with recombinant OspA. Science 250: 553–556.

20. Harr, R., P. Fällman, M. Häggström, L. Wahlström & P. Gustafsson. 1986. GENEUS, a computer system for DNA and protein sequence analysis containing an information retrieval system for the EMBL data library. Nucl. Acids Res. 11: 273–284.

21. Hoheisel, J. & F. M. Pohl. 1986. Simplified preparation of unidirectional deletion clones. Nucl. Acids Res. 14: 3605.

22. Howe, T. R., F. W. LaQuier & A. G. Barbour. 1986. Organization of genes encoding two outer membrane proteins of the Lyme disease agent within a single transcriptional unit. Infect. Immun. 54: 207–212.

23. Howe, T. R., L. W. Mayer & A. G. Barbour. 1985. A single recombinant plasmid expressing two major outer surface proteins of the Lyme disease spirochete. Science 227: 645–646.

24. Huynh, T. U., R. A. Young & R. W. Davis. 1985. Construction and screening cDNA libraries in λgt10 and λgt11. In DNA Cloning, Volume 1, ed. Glover, D. M. IRL Press Limited, Oxford, England, pp. 56–110.

25. Inouye, M. & S. Halegoua. 1980. Secretion and membrane localization of proteins in *Escherichia coli*. Crit. Rev. Biochem. 7: 339–371.

26. Jameson, B. A. & H. Wolf. 1988. The antigenic index: a novel algorithm for predicting antigenic determinants. Comput. Appl. Biosci. 4: 181–186.

27. Kyruchechnikov, V. N., E. I. Korenberg, S. V. Scherbakov, Yu. V. Yovalevsky & M. L. Levin. 1988. Identification of Borrelia isolated in the USSR from *Ixodes persulcatus* schulze ticks. J. Microbiol. Epidemiol. Immunobiol. 12: 41–44.

28. Loenen, W. A. M. & W. J. Brammer. 1980. A bacteriophage lambda vector for cloning large DNA fragments made with several restriction enzymes. Gene 20: 249–259.

29. Malloy, D. C., R. K. Nauman & H. Paxton. 1990. Detection of *Borrelia burgdorferi* using the polymerase chain reaction. J. Clin. Microbiol. 28: 1089–1093.

30. Maniatis, T. E., E. F. Fritsch & J. Sambrook. 1982. Molecular cloning: A laboratory manual. Cold Spring Harbor, New York, Cold Spring Harbor, N.Y. USA, Laboratory press.

31. Meier, J. T., M. I. Simon & A. G. Barbour. 1985. Antigenic variation is associated with DNA rearrangements in a relapsing fever borrelia. Cell 41: 403–409.

32. Nielsen, S. L., K. K. Y. Young & A. G. Barbour. 1990. Detection of *Borrelia burgdorferi* DNA by the polymerase chain reaction. Mol. Cell. Probes. 4: 73–79.

33. Plasterk, R. H. A., M. I. Simon & A. G. Barbour. 1985. Transposition of structural genes to an expression sequence on a linear plasmid causes antigenic variation in the bacterium *Borrelia hermsii*. Nature 318: 257–263.

34. Postic, D., C. Edlinger, C. Richaud, F. Grimont, Y. Dufresne, P. Perolat, G. Baranton & P. A. D. Grimont. 1990. Two genomic species in *Borrelia burgdorferi*. Res. Microbiol. 141: 465–475.

35. Rosa, P. A. & T. G. Schwan. 1989. A specific and sensitive assay for the Lyme disease spirochete *Borrelia burgdorferi* using the polymerase chain reaction. J. Infect. Dis. 160: 1018–1029.

36. Rosa, P. A., D. Hogan & T. G. Schwan. 1991. Polymerase chain reaction analyses identify two distinct classes of *Borrelia burgdorferi*. J. Clin. Microbiol. 29: 524–532.

37. Rosenberg, M, & O. Court. 1979. Regulatory sequences involved in the promotion and termination of transcription. Ann. Rev. Genet. 13: 256–275.

38. Sanger, F., S. Nicklen & A. R. Coulson. 1977. DNA sequencing with chain-terminating inhibitors. Proc. Natl. Acad. Sci. USA 74: 5463–5467.

39. Saunders, S. E. & J. F. Burke. 1990. Rapid isolation of miniprep. DNA for double strand sequencing. Nucl. Acids Res. 18: 4948.

40. Schaible, U. E., M. D. Kramer, K. EIchman, M. Modolell, C. Museteanu & M. M. Simon. 1990. Monoclonal antibodies specific for the outer surface protein A (OspA) of *Borrelia burgdorferi* prevent Lyme borreliosis in severe combined immunodeficiency (scid) mice. Proc. Natl. Acad. Sci. USA 87: 3768–3772.

41. Schubach, W. H., S. Mundri, R. J. Dattwyler & B. J. Luft. 1991. Mapping antibody-binding domains of the major outer surface membrane protein (OspA) of *Borrelia burgdorferi*. Infect. Immun. 59: 1911–1915.

42. Schwan, T. G. & W. Burgdorfer. 1987. Antigenic changes of *Borrelia burgdorferi* as a result of in vitro cultivation. J. Infect. Dis. 156: 852–853.

43. Schwan, T. G., W. Burgdorfer & C. F. Garon. 1988. Changes in infectivity and plasmid profile of the Lyme disease spirochete, *Borrelia burgdorferi*, as a result of in vitro cultivation. Infect. Immun. 56: 1831–1836.

44. Stiernstedt, G. 1985. Tick-borne Borrelia infection in Sweden. Scan. J. Infect. Dis. Suppl. 45: 1–70.

45. Wallich. R., U. E. Schaible, M. M. Simon, A. Heiberger & M. D. Kramer. 1989. Cloning and sequencing of the gene encoding the outer surface protein A (OspA) of a European *Borrelia burgdorferi* isolate. Nucl. Acids Res. 17: 8864.

46. Williams, J. G. & P. J. Mason. 1985. Hybridization in the analysis of RNA. In Nucleic acid hybridization. Hames, B. D. & S. J. Higgins (eds), Oxford: IRL Press, pp. 139–160.

47. Wilske, B., V. Preacu-Mursic, G. Schierz, R. Kuhbeck, A. G. Barbour & M. Kramer. 1988. Antigenic variability of *Borrelia burgdorferi*. Ann N. Y. Acad. Sci. 539: 126–143.

48. von Gabain, A., J. G. Belasco, J. L. Schottel, A. C. Y. Chang & S. N. Cohen. 1983. Decay of mRNA in *Escherichia coli:* investigation of the fate of specific segments of transcripts. Proc. Natl. Acad. Sci. USA 80: 653–657.

49. von Heijne, G. 1983. Patterns of amino acids near signal sequence cleavage sites. Eur. J. Biochem. 133: 17–21.

50. Wu, H. C. & M. Tokunaga. 1986. Biogenesis of lipoproteins in bacteria. In Current Topics in Microbiology and Immunology, Vol. 125, pp. 127–157.

51. Arnhem, N. & Levenson, C. H. 36, Oct. 1, 1990 C&EN special report. Polymerase Chain Reaction.

52. Sambrook, J. et al. Molecular Cloning, a laboratory manual.

53. Old, R. W. and Primrose, S. B. Principles of Gene Manipulation, a textbook.

54. Gray, M. R., Colot, H. V., Guarente, L. and Rosbach, M. 1982. Open reading frame cloning: identification, cloning and expression of open reading frame DNA. Proc. Natl. Acad. Sci. USA 79: 6598–6602.

55. Löwenadler, B., Nilsson, B., Abrahmsén, L., Moks, T., Ljungquist, L., Holmgren, E., Paleus, S., Josephson, S., Philipson, L. and Uhlén, M. 1986. Production of specific antibodies against protein A fusions. EMBO J. 5: 2393–2398.

56. Löwenadler, B., Jansson, B., Paleus, S., Holmgren, E., Nilsson, B., Moks, T., Palm, G., Josephson, S., Philipson, L. and Uhlén, M. 1987. A gene fusion system for generating antibodies against short peptides. Gene 58: 87–97.

57. Löwenadler, B., Svennerholm, A. -M., Gidlund, M., Holmgren, E., Krook, K., Svanholm, C., Ulff, S. and Josephson, S. 1990. Enhanced immunogenicity of recombinant peptide fusions containing multiple copies of a heterologous T helper epitope. Eur. J. Immunol. 20: 1541–1545.

58. Löwenadler, B., Lake, M., Elmblad, A., Holmgren, E., Holmgren, J., Karlström, A. and Svennerholm, A. -M. 1991. A recombinant *Escherichia coli* heat-stable enterotoxin (STa) fusion protein eliciting anti-STa neutralizing antibodies. FEMS Microbiol. Lett. 82: 271–278.

59. Nakamura, K., Masui, Y. and Inouye, M. 1982. Use of a lac promoter-operator fragment as a transcriptional control switch for expression of the constitutive lpp gene in *Escherichia coli*. J. Mol. Appl. Gen. 1: 289–299.

60. Smith, D. B. and Johnson, K. S. 1988. Single-step purification of polypeptides expressed in *Escherichia coli* as fusions with glutathione S-transferase. Gene 67: 31–40.

61. Yansura, D. G. 1990. Expression as trpe fusion. In Methods in Enzymology. Ed. Goeddel, D. V. Vol 185: 161–166.

62. Hanahan D. (1983) J. Mol. Biol. 166:557.

63. von Heijne, G. The structure of signal peptides from bacterial lipoproteins. Protein Engineering vol. 2, no. 7 pp. 531–534, 1989.

64. Nakamura K., Inouye M. DNA sequence of the gene for the outer membrane lipoprotein of *E. coli:* an extremely AT-rich promoter. Cell 1979; 18:1109–17.

---

SEQUENCE LISTING

```
(1) GENERAL INFORMATION:

(iii) NUMBER OF SEQUENCES: 22

(2) INFORMATION FOR SEQ ID NO: 1:

(i) SEQUENCE CHARACTERISTICS:
       (A) LENGTH: 1959 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Borrelia burgdorferi
       (B) STRAIN: B31 (ATCC 35210)

(ix) FEATURE:
```

(A) NAME/KEY: misc_feature
              (B) LOCATION: 123..142
              (D) OTHER INFORMATION: /function= "Primer"

(ix) FEATURE:
              (A) NAME/KEY: misc_feature
              (B) LOCATION: 584..607
              (D) OTHER INFORMATION: /function= "Primer"

(ix) FEATURE:
              (A) NAME/KEY: misc_feature
              (B) LOCATION: 776..794
              (D) OTHER INFORMATION: /function= "Primer"

(ix) FEATURE:
              (A) NAME/KEY: misc_feature
              (B) LOCATION: 806..817
              (D) OTHER INFORMATION: /function= "Primer"

(ix) FEATURE:
              (A) NAME/KEY: CDS
              (B) LOCATION: 119..940
              (D) OTHER INFORMATION: /product= "OspA"

(ix) FEATURE:
              (A) NAME/KEY: CDS
              (B) LOCATION: 950..1840
              (D) OTHER INFORMATION: /product= "OspB"

(xi) SEQUENCE DESCRIPTION: SEQ ID NO: 1:

```
AAACCTAATT GAAGTTATTA TCATTTTATT TTTTTTCAAT TTTCTATTTG TTATTTGTTA      60

ATCTTATAAT ATAATTATAC TTGTATTAAG TTATATTAAT ATAAAAGGAG AATATATT       118

ATG AAA AAA TAT TTA TTG GGA ATA GGT CTA ATA TTA GCC TTA ATA GCA       166
Met Lys Lys Tyr Leu Leu Gly Ile Gly Leu Ile Leu Ala Leu Ile Ala
  1               5                  10                  15

TGT AAG CAA AAT GTT AGC AGC CTT GAC GAG AAA AAC AGC GTT TCA GTA       214
Cys Lys Gln Asn Val Ser Ser Leu Asp Glu Lys Asn Ser Val Ser Val
             20                  25                  30

GAT TTG CCT GGT GAA ATG AAA GTT CTT GTA AGC AAA GAA AAA AAC AAA       262
Asp Leu Pro Gly Glu Met Lys Val Leu Val Ser Lys Glu Lys Asn Lys
         35                  40                  45

GAC GGC AAG TAC GAT CTA ATT GCA ACA GTA GAC AAG CTT GAG CTT AAA       310
Asp Gly Lys Tyr Asp Leu Ile Ala Thr Val Asp Lys Leu Glu Leu Lys
     50                  55                  60

GGA ACT TCT GAT AAA AAC AAT GGA TCT GGA GTA CTT GAA GGC GTA AAA       358
Gly Thr Ser Asp Lys Asn Asn Gly Ser Gly Val Leu Glu Gly Val Lys
 65                  70                  75                  80

GCT GAC AAA AGT AAA GTA AAA TTA ACA ATT TCT GAC GAT CTA GGT CAA       406
Ala Asp Lys Ser Lys Val Lys Leu Thr Ile Ser Asp Asp Leu Gly Gln
                 85                  90                  95

ACC ACA CTT GAA GTT TTC AAA GAA GAT GGC AAA ACA CTA GTA TCA AAA       454
Thr Thr Leu Glu Val Phe Lys Glu Asp Gly Lys Thr Leu Val Ser Lys
            100                 105                 110

AAA GTA ACT TCC AAA GAC AAG TCA TCA ACA GAA GAA AAA TTC AAT GAA       502
Lys Val Thr Ser Lys Asp Lys Ser Ser Thr Glu Glu Lys Phe Asn Glu
        115                 120                 125

AAA GGT GAA GTA TCT GAA AAA ATA ATA ACA AGA GCA GAC GGA ACC AGA       550
Lys Gly Glu Val Ser Glu Lys Ile Ile Thr Arg Ala Asp Gly Thr Arg
    130                 135                 140

CTT GAA TAC ACA GGA ATT AAA AGC GAT GGA TCT GGA AAA GCT AAA GAG       598
Leu Glu Tyr Thr Gly Ile Lys Ser Asp Gly Ser Gly Lys Ala Lys Glu
145                 150                 155                 160

GTT TTA AAA GGC TAT GTT CTT GAA GGA ACT CTA ACT GCT GAA AAA ACA       646
Val Leu Lys Gly Tyr Val Leu Glu Gly Thr Leu Thr Ala Glu Lys Thr
                165                 170                 175
```

```
ACA TTG GTG GTT AAA GAA GGA ACT GTT ACT TTA AGC AAA AAT ATT TCA      694
Thr Leu Val Val Lys Glu Gly Thr Val Thr Leu Ser Lys Asn Ile Ser
            180                 185                 190

AAA TCT GGG GAA GTT TCA GTT GAA CTT AAT GAC ACT GAC AGT AGT GCT      742
Lys Ser Gly Glu Val Ser Val Glu Leu Asn Asp Thr Asp Ser Ser Ala
        195                 200                 205

GCT ACT AAA AAA ACT GCA GCT TGG AAT TCA GGC ACT TCA ACT TTA ACA      790
Ala Thr Lys Lys Thr Ala Ala Trp Asn Ser Gly Thr Ser Thr Leu Thr
    210                 215                 220

ATT ACT GTA AAC AGT AAA AAA ACT AAA GAC CTT GTG TTT ACA AAA GAA      838
Ile Thr Val Asn Ser Lys Lys Thr Lys Asp Leu Val Phe Thr Lys Glu
225                 230                 235                 240

AAC ACA ATT ACA GTA CAA CAA TAC GAC TCA AAT GGC ACC AAA TTA GAG      886
Asn Thr Ile Thr Val Gln Gln Tyr Asp Ser Asn Gly Thr Lys Leu Glu
                245                 250                 255

GGG TCA GCA GTT GAA ATT ACA AAA CTT GAT GAA ATT AAA AAC GCT TTA      934
Gly Ser Ala Val Glu Ile Thr Lys Leu Asp Glu Ile Lys Asn Ala Leu
            260                 265                 270

AAA TAAGGAGAAT TT ATG AGA TTA TTA ATA GGA TTT GCT TTA GCG TTA        982
Lys            Met Arg Leu Leu Ile Gly Phe Ala Leu Ala Leu
                 1               5                  10

GCT TTA ATA GGA TGT GCA CAA AAA GGT GCT GAG TCA ATT GGT TCT CAA     1030
Ala Leu Ile Gly Cys Ala Gln Lys Gly Ala Glu Ser Ile Gly Ser Gln
            15                  20                  25

AAA GAA AAT GAT CTA AAC CTT GAA GAC TCT AGT AAA AAA TCA CAT CAA     1078
Lys Glu Asn Asp Leu Asn Leu Glu Asp Ser Ser Lys Lys Ser His Gln
        30                  35                  40

AAC GCT AAA CAA GAC CTT CCT GCG GTG ACA GAA GAC TCA GTG TCT TTG     1126
Asn Ala Lys Gln Asp Leu Pro Ala Val Thr Glu Asp Ser Val Ser Leu
    45                  50                  55

TTT AAT GGT AAT AAA ATT TTT GTA AGC AAA GAA AAA AAT AGC TCC GGC     1174
Phe Asn Gly Asn Lys Ile Phe Val Ser Lys Glu Lys Asn Ser Ser Gly
60                  65                  70                  75

AAA TAT GAT TTA AGA GCA ACA ATT GAT CAG GTT GAA CTT AAA GGA ACT     1222
Lys Tyr Asp Leu Arg Ala Thr Ile Asp Gln Val Glu Leu Lys Gly Thr
                80                  85                  90

TCC GAT AAA AAC AAT GGT TCT GGA ACC CTT GAA GGT TCA AAG CCT GAC     1270
Ser Asp Lys Asn Asn Gly Ser Gly Thr Leu Glu Gly Ser Lys Pro Asp
            95                  100                 105

AAG AGT AAA GTA AAA TTA ACA GTT TCT GCT GAT TTA AAC ACA GTA ACC     1318
Lys Ser Lys Val Lys Leu Thr Val Ser Ala Asp Leu Asn Thr Val Thr
        110                 115                 120

TTA GAA GCA TTT GAT GCC AGC AAC CAA AAA ATT TCA AGT AAA GTT ACT     1366
Leu Glu Ala Phe Asp Ala Ser Asn Gln Lys Ile Ser Ser Lys Val Thr
    125                 130                 135

AAA AAA CAG GGG TCA ATA ACA GAG GAA ACT CTC AAA GCT AAT AAA TTA     1414
Lys Lys Gln Gly Ser Ile Thr Glu Glu Thr Leu Lys Ala Asn Lys Leu
140                 145                 150                 155

GAC TCA AAG AAA TTA ACA AGA TCA AAC GGA ACT ACA CTT GAA TAC TCA     1462
Asp Ser Lys Lys Leu Thr Arg Ser Asn Gly Thr Thr Leu Glu Tyr Ser
                160                 165                 170

CAA ATA ACA GAT GCT GAC AAT GCT ACA AAA GCA GTA GAA ACT CTA AAA     1510
Gln Ile Thr Asp Ala Asp Asn Ala Thr Lys Ala Val Glu Thr Leu Lys
            175                 180                 185

AAT AGC ATT AAG CTT GAA GGA AGT CTT GTA GTC GGA AAA ACA ACA GTG     1558
Asn Ser Ile Lys Leu Glu Gly Ser Leu Val Val Gly Lys Thr Thr Val
        190                 195                 200

GAA ATT AAA GAA GGT ACT GTT ACT CTA AAA AGA GAA ATT GAA AAA GAT     1606
Glu Ile Lys Glu Gly Thr Val Thr Leu Lys Arg Glu Ile Glu Lys Asp
    205                 210                 215
```

```
GGA AAA GTA AAA GTC TTT TTG AAT GAC ACT GCA GGT TCT AAC AAA AAA      1654
Gly Lys Val Lys Val Phe Leu Asn Asp Thr Ala Gly Ser Asn Lys Lys
220             225                 230                 235

ACA GGT AAA TGG GAA GAC AGT ACT AGC ACT TTA ACA ATT AGT GCT GAC      1702
Thr Gly Lys Trp Glu Asp Ser Thr Ser Thr Leu Thr Ile Ser Ala Asp
                240                 245                 250

AGC AAA AAA ACT AAA GAT TTG GTG TTC TTA ACA GAT GGT ACA ATT ACA      1750
Ser Lys Lys Thr Lys Asp Leu Val Phe Leu Thr Asp Gly Thr Ile Thr
                    255                 260                 265

GTA CAA CAA TAC AAC ACA GCT GGA ACC AGC CTA GAA GGA TCA GCA AGT      1798
Val Gln Gln Tyr Asn Thr Ala Gly Thr Ser Leu Glu Gly Ser Ala Ser
            270                 275                 280

GAA ATT AAA AAT CTT TCA GAG CTT AAA AAC GCT TTA AAA TAATATATAA       1847
Glu Ile Lys Asn Leu Ser Glu Leu Lys Asn Ala Leu Lys
285                 290                 295

GTAAACCCCC TACAAGGCAT CAGCTAGTGT AGGAAGCTGA CTCTTATACA CAAGTAGCGT    1907

CCTGAACGGA ACCTTTCCCG TTTTCCAGGA TCTGATCTTC CATGTGACCT CC            1959

(2) INFORMATION FOR SEQ ID NO: 2:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Ser Lys Lys Asn Lys
            35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Gly Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220
```

```
Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
            245                 250                 255

Gly Ser Ala Val Glu Ile Thr Lys Leu Asp Glu Ile Lys Asn Ala Leu
                260                 265                 270

Lys
```

(2) INFORMATION FOR SEQ ID NO: 3:

(i) SEQUENCE CHARACTERISTICS:
        (A) LENGTH: 296 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Arg Leu Leu Ile Gly Phe Ala Leu Ala Leu Ala Leu Ile Gly Cys
1               5                   10                  15

Ala Gln Lys Gly Ala Glu Ser Ile Gly Ser Gln Lys Glu Asn Asp Leu
            20                  25                  30

Asn Leu Glu Asp Ser Ser Lys Lys Ser His Gln Asn Ala Lys Gln Asp
        35                  40                  45

Leu Pro Ala Val Thr Glu Asp Ser Val Ser Leu Phe Asn Gly Asn Lys
    50                  55                  60

Ile Phe Val Ser Lys Glu Lys Asn Ser Ser Gly Lys Tyr Asp Leu Arg
65                  70                  75                  80

Ala Thr Ile Asp Gln Val Glu Leu Lys Gly Thr Ser Asp Lys Asn Asn
                85                  90                  95

Gly Ser Gly Thr Leu Glu Gly Ser Lys Pro Asp Lys Ser Lys Val Lys
                100                 105                 110

Leu Thr Val Ser Ala Asp Leu Asn Thr Val Thr Leu Glu Ala Phe Asp
            115                 120                 125

Ala Ser Asn Gln Lys Ile Ser Ser Lys Val Thr Lys Gln Gly Ser
130                 135                 140

Ile Thr Glu Glu Thr Leu Lys Ala Asn Lys Leu Asp Ser Lys Lys Leu
145                 150                 155                 160

Thr Arg Ser Asn Gly Thr Thr Leu Glu Tyr Ser Gln Ile Thr Asp Ala
                165                 170                 175

Asp Asn Ala Thr Lys Ala Val Glu Thr Leu Lys Asn Ser Ile Lys Leu
            180                 185                 190

Glu Gly Ser Leu Val Val Gly Lys Thr Thr Val Glu Ile Lys Glu Gly
        195                 200                 205

Thr Val Thr Leu Lys Arg Glu Ile Glu Lys Asp Gly Lys Val Lys Val
    210                 215                 220

Phe Leu Asn Asp Thr Ala Gly Ser Asn Lys Lys Thr Gly Lys Trp Glu
225                 230                 235                 240

Asp Ser Thr Ser Thr Leu Thr Ile Ser Ala Asp Ser Lys Lys Thr Lys
                245                 250                 255

Asp Leu Val Phe Leu Thr Asp Gly Thr Ile Thr Val Gln Gln Tyr Asn
            260                 265                 270

Thr Ala Gly Thr Ser Leu Glu Gly Ser Ala Ser Glu Ile Lys Asn Leu
        275                 280                 285

Ser Glu Leu Lys Asn Ala Leu Lys
290                 295
```

(2) INFORMATION FOR SEQ ID NO: 4:

(i) SEQUENCE CHARACTERISTICS:
        (A) LENGTH: 1978 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Borrelia burgdorferi
        (B) STRAIN: ACA1
        (C) INDIVIDUAL ISOLATE: Swedish isolate, pt. acrodermatitis
            chronicum migrans (ix) FEATURE:
        (A) NAME/KEY: misc_feature
        (B) LOCATION: 85..104
        (D) OTHER INFORMATION: /function= "Primer"

(ix) FEATURE:
        (A) NAME/KEY: misc_feature
        (B) LOCATION: 111..130
        (D) OTHER INFORMATION: /function= "Primer"

(ix) FEATURE:
        (A) NAME/KEY: misc_feature
        (B) LOCATION: 948..965
        (D) OTHER INFORMATION: /function= "Primer"

(ix) FEATURE:
        (A) NAME/KEY: CDS
        (B) LOCATION: 127..948
        (D) OTHER INFORMATION: /product= "OspA"

(ix) FEATURE:
        (A) NAME/KEY: CDS
        (B) LOCATION: 962..1861
        (D) OTHER INFORMATION: /product= "OspB"

(xi) SEQUENCE DESCRIPTION: SEQ ID NO: 4:

```
ATACCTAATT TAAAATTATT ATCATTTTAT TTTTTTTTTA ATTTTCTATT TGTTATTTAT        60

TGATCTTATA CTATAATTAT ACTTGTATTA AGTTATATTA ATATAATATA AAAAGGAGAA       120

TATATT ATG AAA AAA TAT TTA TTG GGA ATA GGT CTA ATA TTA GCC TTA          168
       Met Lys Lys Tyr Leu Leu Gly Ile Gly Leu Ile Leu Ala Leu
         1               5                  10

ATA GCA TGC AAG CAA AAT GTT AGC AGC CTT GAT GAA AAA AAC AGC GCT         216
Ile Ala Cys Lys Gln Asn Val Ser Ser Leu Asp Glu Lys Asn Ser Ala
 15              20                  25                  30

TCA GTA GAT TTG CCT GGT GAG ATG AAA GTT CTT GTA AGT AAA GAA AAA         264
Ser Val Asp Leu Pro Gly Glu Met Lys Val Leu Val Ser Lys Glu Lys
                 35                  40                  45

GAC AAA GAC GGT AAG TAC AGT CTA AAG GCA ACA GTA GAC AAG ATT GAG         312
Asp Lys Asp Gly Lys Tyr Ser Leu Lys Ala Thr Val Asp Lys Ile Glu
                 50                  55                  60

CTA AAA GGA ACT TCT GAT AAA GAC AAT GGT TCT GGA GTG CTT GAA GGT         360
Leu Lys Gly Thr Ser Asp Lys Asp Asn Gly Ser Gly Val Leu Glu Gly
                 65                  70                  75

ACA AAA GAT GAC AAA AGT AAA GCA AAA TTA ACA ATT GCT GAC GAT CTA         408
Thr Lys Asp Asp Lys Ser Lys Ala Lys Leu Thr Ile Ala Asp Asp Leu
         80                  85                  90

AGT AAA ACC ACA TTC GAA CTT TTC AAA GAA GAT GGC AAA ACA TTA GTG         456
Ser Lys Thr Thr Phe Glu Leu Phe Lys Glu Asp Gly Lys Thr Leu Val
 95                 100                 105                 110

TCA AGA AAA GTA AGT TCT AAA GAC AAA ACA TCA ACA GAT GAA ATG TTC         504
Ser Arg Lys Val Ser Ser Lys Asp Lys Thr Ser Thr Asp Glu Met Phe
```

```
                    115                  120                      125
AAT GAA AAA GGT GAA TTG TCT GCA AAA ACC ATG ACA AGA GAA AAT GGA         552
Asn Glu Lys Gly Glu Leu Ser Ala Lys Thr Met Thr Arg Glu Asn Gly
                130                 135                 140

ACC AAA CTT GAA TAT ACA GAA ATG AAA AGC GAT GGA ACC GGA AAA GCT         600
Thr Lys Leu Glu Tyr Thr Glu Met Lys Ser Asp Gly Thr Gly Lys Ala
                145                 150                 155

AAA GAA GTT TTA AAA AAC TTT ACT CTT GAA GGA AAA GTA GCT AAT GAT         648
Lys Glu Val Leu Lys Asn Phe Thr Leu Glu Gly Lys Val Ala Asn Asp
            160                 165                 170

AAA GTA ACA TTG GAA GTA AAA GAA GGA ACC GTT ACT TTA AGT AAG GAA         696
Lys Val Thr Leu Glu Val Lys Glu Gly Thr Val Thr Leu Ser Lys Glu
175                 180                 185                 190

ATT GCA AAA TCT GGA GAA GTA ACA GTT GCT CTT AAT GAC ACT AAC ACT         744
Ile Ala Lys Ser Gly Glu Val Thr Val Ala Leu Asn Asp Thr Asn Thr
                195                 200                 205

ACT CAG GCT ACT AAA AAA ACT GGC GCA TGG GAT TCA AAA ACT TCT ACT         792
Thr Gln Ala Thr Lys Lys Thr Gly Ala Trp Asp Ser Lys Thr Ser Thr
                210                 215                 220

TTA ACA ATT AGT GTT AAC AGC AAA AAA ACT ACA CAA CTT GTG TTT ACT         840
Leu Thr Ile Ser Val Asn Ser Lys Lys Thr Thr Gln Leu Val Phe Thr
            225                 230                 235

AAA CAA GAC ACA ATA ACT GTA CAA AAA TAC GAC TCC GCA GGT ACC AAT         888
Lys Gln Asp Thr Ile Thr Val Gln Lys Tyr Asp Ser Ala Gly Thr Asn
240                 245                 250

TTA GAA GGC ACA GCA GTC GAA ATT AAA ACA CTT GAT GAA CTT AAA AAC         936
Leu Glu Gly Thr Ala Val Glu Ile Lys Thr Leu Asp Glu Leu Lys Asn
255                 260                 265                 270

GCT TTG AAA TAAATAAGGA GAATTT ATG AAA CAA TAT TTA CTA GTA TTT          985
Ala Leu Lys                    Met Lys Gln Tyr Leu Leu Val Phe
                                 1               5

GCT TTG GTA TTA GCT TTA ATA GCG TGT TCT CAA AAA GGT ACT GAG CCA        1033
Ala Leu Val Leu Ala Leu Ile Ala Cys Ser Gln Lys Gly Thr Glu Pro
        10                  15                  20

AAA AGT ACT TCA CAA GAC CAT AAT GAT CAA GAA ATT ATA AAC TCA GAC        1081
Lys Ser Thr Ser Gln Asp His Asn Asp Gln Glu Ile Ile Asn Ser Asp
25                  30                  35                  40

AAT ACA CCA AAA GAC TCT AAA AAA GAT CTT ACT GTT TTA GCA GAA GAA        1129
Asn Thr Pro Lys Asp Ser Lys Lys Asp Leu Thr Val Leu Ala Glu Glu
                45                  50                  55

AAC TCT GTA CCT CTA TTT AAT GGC AAT AAA ATT TTC GTA AGC AAA GAA        1177
Asn Ser Val Pro Leu Phe Asn Gly Asn Lys Ile Phe Val Ser Lys Glu
                60                  65                  70

AAA AAT TCT GCT GGT AAA TAT GAG TTA AGA GCA ACA GTT GAT ACG GTT        1225
Lys Asn Ser Ala Gly Lys Tyr Glu Leu Arg Ala Thr Val Asp Thr Val
            75                  80                  85

GAG CTT AAA GGG GTT TCT GAC AAG AAT AAT GGA TCT GGC AAG CTT GAA        1273
Glu Leu Lys Gly Val Ser Asp Lys Asn Asn Gly Ser Gly Lys Leu Glu
        90                  95                  100

GGT ACA AAA GCT GAC AAG ACT AAA GTA GCA ATG ACA ATT GCT GAC GAT        1321
Gly Thr Lys Ala Asp Lys Thr Lys Val Ala Met Thr Ile Ala Asp Asp
105                 110                 115                 120

CTA AAT ACA ATA ACT GTA GAA ACA TAT GAT GCA AGC AAT AAA AAA ACT        1369
Leu Asn Thr Ile Thr Val Glu Thr Tyr Asp Ala Ser Asn Lys Lys Thr
                125                 130                 135

GGA AGT GAA GTT GTT AAA AAA CAA GGG TCA GTA ATA AAA GAA TCT TAC        1417
Gly Ser Glu Val Val Lys Lys Gln Gly Ser Val Ile Lys Glu Ser Tyr
            140                 145                 150

AAA GCT AAT AAA TTA GAC TCA AAA AAA ATA ACA AGA GAA AAC GAA ACT        1465
```

```
Lys Ala Asn Lys Leu Asp Ser Lys Lys Ile Thr Arg Glu Asn Glu Thr
            155                 160                 165

ACA CTT GAA TAT TCA GAA ATG ACA GAT TCT AGC AAT GAT ACA AAA GCA      1513
Thr Leu Glu Tyr Ser Glu Met Thr Asp Ser Ser Asn Asp Thr Lys Ala
        170                 175                 180

GTA GAA ACT CTA AAA AAT GGT ATT AAA CTA GAA GGA AGT CTT GTT GGT      1561
Val Glu Thr Leu Lys Asn Gly Ile Lys Leu Glu Gly Ser Leu Val Gly
185                 190                 195                 200

GGA AAA ACA ACC GTA AAA TTA ACA GAA GGT ACT ATT ACA TTA ACA AGA      1609
Gly Lys Thr Thr Val Lys Leu Thr Glu Gly Thr Ile Thr Leu Thr Arg
                205                 210                 215

GAA ATA GAA CAA GAT GGA AAA GTA AAA ATC TAC TTA AAT GAT ACT ACA      1657
Glu Ile Glu Gln Asp Gly Lys Val Lys Ile Tyr Leu Asn Asp Thr Thr
            220                 225                 230

TCT GGT AGT ACT AAA AAA ACA GCA ACA TGG AAC GAA ACT ACT AAC ACA      1705
Ser Gly Ser Thr Lys Lys Thr Ala Thr Trp Asn Glu Thr Thr Asn Thr
        235                 240                 245

TTA ACA ATT AGT GCT GAC AGT AAA AAA ACT AAA GAT TTT GTG TTC TTA      1753
Leu Thr Ile Ser Ala Asp Ser Lys Lys Thr Lys Asp Phe Val Phe Leu
    250                 255                 260

ACA GAT GGT ACC ATT ACA GTA CAA GCA TAT GAC ACA GCA GGT ACT AAA      1801
Thr Asp Gly Thr Ile Thr Val Gln Ala Tyr Asp Thr Ala Gly Thr Lys
265                 270                 275                 280

CTT GAG GGC AAC TCA AGT GAA ATT AAA GAT CTT GCA GCA CTT AAA GCT      1849
Leu Glu Gly Asn Ser Ser Glu Ile Lys Asp Leu Ala Ala Leu Lys Ala
                285                 290                 295

GCT TTA AAA TAACATAAAA GTAAACATCC TACATCGGCT AATACCTTTG              1898
Ala Leu Lys
            300

TAGGTGTTGT TTATTACAAC TAAAAATTGA ATTTATATTT TCAATTTGT TACTTCTGGG    1958

AAAGTCTCTA GGAGACTTTC                                                1978

(2) INFORMATION FOR SEQ ID NO: 5:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO: 5:

Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Ala Ser Val
                 20                  25                  30

Asp Leu Pro Gly Glu Met Lys Val Leu Val Ser Lys Glu Lys Asp Lys
             35                  40                  45

Asp Gly Lys Tyr Ser Leu Lys Ala Thr Val Asp Lys Ile Glu Leu Lys
         50                  55                  60

Gly Thr Ser Asp Lys Asp Asn Gly Ser Gly Val Leu Glu Gly Thr Lys
 65                  70                  75                  80

Asp Asp Lys Ser Lys Ala Lys Leu Thr Ile Ala Asp Asp Leu Ser Lys
                 85                  90                  95

Thr Thr Phe Glu Leu Phe Lys Glu Asp Gly Lys Thr Leu Val Ser Arg
            100                 105                 110

Lys Val Ser Ser Lys Asp Lys Thr Ser Thr Asp Glu Met Phe Asn Glu
        115                 120                 125
```

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys (2) INFORMATION FOR SEQ ID NO: 6:

(i) SEQUENCE CHARACTERISTICS:
        (A) LENGTH: 299 amino acids
        (B) TYPE: amino acid
        (D) TOPOLOGY: linear (ii) MOLECULE TYPE: protein (xi) SEQUENCE DESCRIPTION: SEQ ID NO: 6:

Met Lys Gln Tyr Leu Leu Val Phe Ala Leu Val Leu Ala Leu Ile Ala
1               5                   10                  15

Cys Ser Gln Lys Gly Thr Glu Pro Lys Ser Thr Ser Gln Asp His Asn
                20                  25                  30

Asp Gln Glu Ile Ile Asn Ser Asp Asn Thr Pro Lys Asp Ser Lys Lys
            35                  40                  45

Asp Leu Thr Val Leu Ala Glu Glu Asn Ser Val Pro Leu Phe Asn Gly
    50                  55                  60

Asn Lys Ile Phe Val Ser Lys Glu Lys Asn Ser Ala Gly Lys Tyr Glu
65                  70                  75                  80

Leu Arg Ala Thr Val Asp Thr Val Glu Leu Lys Gly Val Ser Asp Lys
                85                  90                  95

Asn Asn Gly Ser Gly Lys Leu Glu Gly Thr Lys Ala Asp Lys Thr Lys
            100                 105                 110

Val Ala Met Thr Ile Ala Asp Asp Leu Asn Thr Ile Thr Val Glu Thr
        115                 120                 125

Tyr Asp Ala Ser Asn Lys Lys Thr Gly Ser Glu Val Val Lys Lys Gln
    130                 135                 140

Gly Ser Val Ile Lys Glu Ser Tyr Lys Ala Asn Lys Leu Asp Ser Lys
145                 150                 155                 160

Lys Ile Thr Arg Glu Asn Glu Thr Thr Leu Glu Tyr Ser Glu Met Thr
                165                 170                 175

Asp Ser Ser Asn Asp Thr Lys Ala Val Glu Thr Leu Lys Asn Gly Ile
            180                 185                 190

Lys Leu Glu Gly Ser Leu Val Gly Gly Lys Thr Thr Val Lys Leu Thr
        195                 200                 205

-continued

```
Glu Gly Thr Ile Thr Leu Thr Arg Glu Ile Glu Gln Asp Gly Lys Val
    210                 215                 220
Lys Ile Tyr Leu Asn Asp Thr Thr Ser Gly Ser Thr Lys Lys Thr Ala
225                 230                 235                 240
Thr Trp Asn Glu Thr Thr Asn Thr Leu Thr Ile Ser Ala Asp Ser Lys
                245                 250                 255
Lys Thr Lys Asp Phe Val Phe Leu Thr Asp Gly Thr Ile Thr Val Gln
            260                 265                 270
Ala Tyr Asp Thr Ala Gly Thr Lys Leu Glu Gly Asn Ser Ser Glu Ile
        275                 280                 285
Lys Asp Leu Ala Ala Leu Lys Ala Ala Leu Lys
    290                 295
```

(2) INFORMATION FOR SEQ ID NO: 7:

(i) SEQUENCE CHARACTERISTICS:
        (A) LENGTH: 1958 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Borrelia burgdorferi
        (B) STRAIN: Ip90
        (C) INDIVIDUAL ISOLATE: Isolate from I. persulcatus from
            Soviet Union (ix) FEATURE:
        (A) NAME/KEY: CDS
        (B) LOCATION: 125..949
        (D) OTHER INFORMATION: /product= "OspA"

(ix) FEATURE:
        (A) NAME/KEY: CDS
        (B) LOCATION: 959..1843
        (D) OTHER INFORMATION: /product= "OspB"

(xi) SEQUENCE DESCRIPTION: SEQ ID NO: 7:

```
ATATATAATT AGAATTATTA TCATTTTATT TTTTTTTAAT TTGCTATTTG TTATTTGTTG        60

ATCTTATACT ATAATTATAT TTGTATTAAG TTATATTAAT ATAATATAAA AAGGAGAATA       120

TATT ATG AAA AAA TAT TTA TTG GGA ATA GGT CTA ATA TTA GCA TTA ATA        169
     Met Lys Lys Tyr Leu Leu Gly Ile Gly Leu Ile Leu Ala Leu Ile
     1               5                  10                  15

GCA TGT AAG CAA AAT GTT AGC AGC CTT GAT GAA AAA AAT AGC GTT TCA         217
Ala Cys Lys Gln Asn Val Ser Ser Leu Asp Glu Lys Asn Ser Val Ser
                20                  25                  30

GTA GAT TTA CCT GGT GGA ATG CAA GTT CTT GTA AGT AAA GAA AAA GAC         265
Val Asp Leu Pro Gly Gly Met Gln Val Leu Val Ser Lys Glu Lys Asp
            35                  40                  45

AAA GAT GGT AAA TAC AGT CTA ATG GCA ACA GTA GAC AAG CTT GAG CTT         313
Lys Asp Gly Lys Tyr Ser Leu Met Ala Thr Val Asp Lys Leu Glu Leu
        50                  55                  60

AAA GGA ACT TCT GAT AAA AAC AAC GGT TCT GGA ACA CTT GAA GGT GAA         361
Lys Gly Thr Ser Asp Lys Asn Asn Gly Ser Gly Thr Leu Glu Gly Glu
    65                  70                  75

AAA ACT GAC AAA AGT AAA GCA AAA TTA ACA ATT GCT GAG GAT CTA AGT         409
Lys Thr Asp Lys Ser Lys Ala Lys Leu Thr Ile Ala Glu Asp Leu Ser
80                  85                  90                  95

AAA ACC ACA TTT GAA ATC TTC AAA GAA GAT GGC AAA ACA TTA GTA TCA         457
Lys Thr Thr Phe Glu Ile Phe Lys Glu Asp Gly Lys Thr Leu Val Ser
                100                 105                 110
```

```
AAA AAA GTA ACC CTT AAA GAC AAG TCA TCA ACA GAA GAA AAA TTC AAC         505
Lys Lys Val Thr Leu Lys Asp Lys Ser Ser Thr Glu Glu Lys Phe Asn
            115                 120                 125

GCA AAG GGT GAA GCA TCT GAA AAA ACA ATA GTA AGA GCA AAT GGA ACC         553
Ala Lys Gly Glu Ala Ser Glu Lys Thr Ile Val Arg Ala Asn Gly Thr
        130                 135                 140

AGA CTT GAA TAC ACA GAC ATA AAA AGC GAT AAA ACC GGA AAA GCT AAA         601
Arg Leu Glu Tyr Thr Asp Ile Lys Ser Asp Lys Thr Gly Lys Ala Lys
145                 150                 155

GAA GTT TTA AAA GAC TTT GCT CTT GAA GGA ACT CTA GCT GCT GAC GGC         649
Glu Val Leu Lys Asp Phe Ala Leu Glu Gly Thr Leu Ala Ala Asp Gly
160                 165                 170                 175

AAA ACA ACA TTA AAA GTT ACA GAA GGC ACT GTT GTT TTA AGC AAA CAC         697
Lys Thr Thr Leu Lys Val Thr Glu Gly Thr Val Val Leu Ser Lys His
        180                 185                 190

ATT TCA AAC TCT GGA GAA ATA ACA GTT GAG CTT AAT GAC TCT GAC ACT         745
Ile Ser Asn Ser Gly Glu Ile Thr Val Glu Leu Asn Asp Ser Asp Thr
        195                 200                 205

ACT CAG GCT ACT AAA AAA ACT GGA ACA TGG GAT TCA AAG ACT TCC ACT         793
Thr Gln Ala Thr Lys Lys Thr Gly Thr Trp Asp Ser Lys Thr Ser Thr
        210                 215                 220

TTA ACA ATT AGT GTG AAT AGC CGA AAA ACC AAA AAC CTT GTA TTC ACA         841
Leu Thr Ile Ser Val Asn Ser Arg Lys Thr Lys Asn Leu Val Phe Thr
        225                 230                 235

AAA GAA GAC ACA ATA ACA GTA CAA AAA TAC GAC TCA GCA GGC ACC AAT         889
Lys Glu Asp Thr Ile Thr Val Gln Lys Tyr Asp Ser Ala Gly Thr Asn
240                 245                 250                 255

CTA GAA GGC AAA GCA GTC GAA ATT ACA ACG CTT AAA GAA CTT AAA GAT         937
Leu Glu Gly Lys Ala Val Glu Ile Thr Thr Leu Lys Glu Leu Lys Asp
                260                 265                 270

GCT TTA AAA TAGGGAGAGT TT ATG AAA AAA TAT TTA CTA GGA TTT GCT          985
Ala Leu Lys              Met Lys Lys Tyr Leu Leu Gly Phe Ala
        275                  1               5

TTA GTA TTA GCT TTA ATA GCA TGT GGA CAA AAA GGT GCT GAG CCA AAA         1033
Leu Val Leu Ala Leu Ile Ala Cys Gly Gln Lys Gly Ala Glu Pro Lys
 10              15                  20                  25

CAC AAT GAT CAA GAC GTT GAA GAC TTA AAA AAA GAT CAA AAA GAC GAC         1081
His Asn Asp Gln Asp Val Glu Asp Leu Lys Lys Asp Gln Lys Asp Asp
                30                  35                  40

TCT AAA AAA GAT CTT CCT TTG GTA ACA GAA GAC ACG GTG AAG TTA TTT         1129
Ser Lys Lys Asp Leu Pro Leu Val Thr Glu Asp Thr Val Lys Leu Phe
            45                  50                  55

AAT AAC AAT GAA ATT TTC ATC AGC AAA GAA AAA AAT GAA GAC GAT AAA         1177
Asn Asn Asn Glu Ile Phe Ile Ser Lys Glu Lys Asn Glu Asp Asp Lys
        60                  65                  70

TAT GAA TTA AGA TCA ATA GTG GAC AAG GTT GAG CTT AAA GGC CTT TCT         1225
Tyr Glu Leu Arg Ser Ile Val Asp Lys Val Glu Leu Lys Gly Leu Ser
 75                  80                  85

GAG AAG AAT ACT GGT GCT GGA GAG CTT GAA GGT TTA AAA GCT GAC AAA         1273
Glu Lys Asn Thr Gly Ala Gly Glu Leu Glu Gly Leu Lys Ala Asp Lys
 90                  95                 100                 105

AGC AAA GTA ACA ATG TTG GTT TCT GAC GAT CTA AAT ACA ATA ACT ATA         1321
Ser Lys Val Thr Met Leu Val Ser Asp Asp Leu Asn Thr Ile Thr Ile
            110                 115                 120

GAA ACA TAT GAT CCA AGC AAC AAA AAA ATT TCA AGC CAA GTG GCT AAA         1369
Glu Thr Tyr Asp Pro Ser Asn Lys Lys Ile Ser Ser Gln Val Ala Lys
            125                 130                 135

AAA CAG GGA TCA CTA ACA GAA GAA ACT TAC AAA ACT AGT AAA TTA AGC         1417
Lys Gln Gly Ser Leu Thr Glu Glu Thr Tyr Lys Thr Ser Lys Leu Ser
```

```
                140                 145                 150
GCA AAG AAA ATA ACA AGA TCA AAT AAT ACT ACA ATT GAA TAT ACA GAA    1465
Ala Lys Lys Ile Thr Arg Ser Asn Asn Thr Thr Ile Glu Tyr Thr Glu
    155                 160                 165

ATG ACA GAC GCT GAC AAT GCT TCA AAA GCA GTG GAA ACT CTA AAA AAT    1513
Met Thr Asp Ala Asp Asn Ala Ser Lys Ala Val Glu Thr Leu Lys Asn
170                 175                 180                 185

GGT ATC ACC CTT GAA GGA AGT CTT GTA GGT GGA AAA ACA ACC TTA ACA    1561
Gly Ile Thr Leu Glu Gly Ser Leu Val Gly Gly Lys Thr Thr Leu Thr
                190                 195                 200

ATA AAA GAG GGC ACT GTT ACT TTA AAA AAA GAA ATT GAA AAA GCT GGA    1609
Ile Lys Glu Gly Thr Val Thr Leu Lys Lys Glu Ile Glu Lys Ala Gly
            205                 210                 215

ACA GTA AAA CTC TTT TTA GAT GAC ACT GCA AGT AGT GCT ACT AAA AAA    1657
Thr Val Lys Leu Phe Leu Asp Asp Thr Ala Ser Ser Ala Thr Lys Lys
        220                 225                 230

ACA GCT GTA TGG AAC GAT ACT TCT AGC ACC TTA ACA GTT AGT GCT GAA    1705
Thr Ala Val Trp Asn Asp Thr Ser Ser Thr Leu Thr Val Ser Ala Glu
    235                 240                 245

GGC AAA AAA ACT AAA GAT TTC GTG TTC TTA ACA GAC GGT ACA ATT ACA    1753
Gly Lys Lys Thr Lys Asp Phe Val Phe Leu Thr Asp Gly Thr Ile Thr
250                 255                 260                 265

GTA CAA AAT TAT AAC AAA GCA GGC ACT ACA CTT GAA GGT AAA GCA ACT    1801
Val Gln Asn Tyr Asn Lys Ala Gly Thr Thr Leu Glu Gly Lys Ala Thr
                270                 275                 280

GAA ATT AAA GAT CTT GAA GCA CTT AAA GCA GCT TTA AAA TAATATGTAA     1850
Glu Ile Lys Asp Leu Glu Ala Leu Lys Ala Ala Leu Lys
            285                 290                 295

ATAAACATCC TGCAAAGCAT TAGCCAATGC GGATGTTGTT TATGCAACCT AAAAATTGAA  1910

TTTATATTTT TCAATTTGTT ACTTCTAGAA AAGTCTCGGG AGACTTTT              1958

(2) INFORMATION FOR SEQ ID NO: 8:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO: 8:

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Gln Val Leu Val Ser Lys Glu Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Asn Asn Gly Ser Gly Thr Leu Glu Gly Glu Lys
65              70                  75                  80

Thr Asp Lys Ser Lys Ala Lys Leu Thr Ile Ala Glu Asp Leu Ser Lys
            85                  90                  95

Thr Thr Phe Glu Ile Phe Lys Glu Asp Gly Lys Thr Leu Val Ser Lys
        100                 105                 110

Lys Val Thr Leu Lys Asp Lys Ser Ser Thr Glu Glu Lys Phe Asn Ala
    115                 120                 125

Lys Gly Glu Ala Ser Glu Lys Thr Ile Val Arg Ala Asn Gly Thr Arg
```

```
            130                 135                 140
Leu Glu Tyr Thr Asp Ile Lys Ser Asp Lys Thr Gly Lys Ala Lys Glu
145                 150                 155                 160

Val Leu Lys Asp Phe Ala Leu Glu Gly Thr Leu Ala Ala Asp Gly Lys
                165                 170                 175

Thr Thr Leu Lys Val Thr Glu Gly Thr Val Val Leu Ser Lys His Ile
                180                 185                 190

Ser Asn Ser Gly Glu Ile Thr Val Glu Leu Asn Asp Ser Asp Thr Thr
                195                 200                 205

Gln Ala Thr Lys Lys Thr Gly Thr Trp Asp Ser Lys Thr Ser Thr Leu
                210                 215                 220

Thr Ile Ser Val Asn Ser Arg Lys Thr Lys Asn Leu Val Phe Thr Lys
225                 230                 235                 240

Glu Asp Thr Ile Thr Val Gln Lys Tyr Asp Ser Ala Gly Thr Asn Leu
                245                 250                 255

Glu Gly Lys Ala Val Glu Ile Thr Thr Leu Lys Glu Leu Lys Asp Ala
                260                 265                 270

Leu Lys
```

(2) INFORMATION FOR SEQ ID NO: 9:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Lys Lys Tyr Leu Leu Gly Phe Ala Leu Val Leu Ala Leu Ile Ala
 1               5                  10                  15

Cys Gly Gln Lys Gly Ala Glu Pro Lys His Asn Asp Gln Asp Val Glu
                20                  25                  30

Asp Leu Lys Lys Asp Gln Lys Asp Ser Lys Lys Asp Leu Pro Leu
                35                  40                  45

Val Thr Glu Asp Thr Val Lys Leu Phe Asn Asn Asn Glu Ile Phe Ile
 50                  55                  60

Ser Lys Glu Lys Asn Glu Asp Asp Lys Tyr Glu Leu Arg Ser Ile Val
65                  70                  75                  80

Asp Lys Val Glu Leu Lys Gly Leu Ser Glu Lys Asn Thr Gly Ala Gly
                85                  90                  95

Glu Leu Glu Gly Leu Lys Ala Asp Lys Ser Lys Val Thr Met Leu Val
                100                 105                 110

Ser Asp Asp Leu Asn Thr Ile Thr Ile Glu Thr Tyr Asp Pro Ser Asn
                115                 120                 125

Lys Lys Ile Ser Ser Gln Val Ala Lys Lys Gln Gly Ser Leu Thr Glu
                130                 135                 140

Glu Thr Tyr Lys Thr Ser Lys Leu Ser Ala Lys Lys Ile Thr Arg Ser
145                 150                 155                 160

Asn Asn Thr Thr Ile Glu Tyr Thr Glu Met Thr Asp Ala Asp Asn Ala
                165                 170                 175

Ser Lys Ala Val Glu Thr Leu Lys Asn Gly Ile Thr Leu Glu Gly Ser
                180                 185                 190

Leu Val Gly Gly Lys Thr Thr Leu Thr Ile Lys Glu Gly Thr Val Thr
                195                 200                 205
```

```
Leu Lys Lys Glu Ile Glu Lys Ala Gly Thr Val Lys Leu Phe Leu Asp
    210             215                 220

Asp Thr Ala Ser Ser Ala Thr Lys Lys Thr Ala Val Trp Asn Asp Thr
225             230             235                 240

Ser Ser Thr Leu Thr Val Ser Ala Glu Gly Lys Lys Thr Lys Asp Phe
            245                 250                 255

Val Phe Leu Thr Asp Gly Thr Ile Thr Val Gln Asn Tyr Asn Lys Ala
            260                 265                 270

Gly Thr Thr Leu Glu Gly Lys Ala Thr Glu Ile Lys Asp Leu Glu Ala
            275                 280             285

Leu Lys Ala Ala Leu Lys
    290
```

(2) INFORMATION FOR SEQ ID NO: 10:

(i) SEQUENCE CHARACTERISTICS:
        (A) LENGTH: 940 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Borrelia burgdorferi
        (B) STRAIN: N40

(ix) FEATURE:
        (A) NAME/KEY: CDS
        (B) LOCATION: 119..940
        (D) OTHER INFORMATION: /product= "OspA"

(xi) SEQUENCE DESCRIPTION: SEQ ID NO: 10:

```
AAACCTAATT GAAGTTATTA TCATTTTATT TTTTTTCAAT TTTCTATTTG TTATTTGTTA        60

ATCTTATAAT ATAATTATAC TTGTATTAAG TTATATTAAT ATAAAAGGAG AATATATT         118

ATG AAA AAA TAT TTA TTG GGA ATA GGT CTA ATA TTA GCC TTA ATA GCA         166
Met Lys Lys Tyr Leu Leu Gly Ile Gly Leu Ile Leu Ala Leu Ile Ala
  1               5                  10                  15

TGT AAG CAA AAT GTT AGC AGC CTT GAC GAG AAA AAC AGC GTT TCA GTA         214
Cys Lys Gln Asn Val Ser Ser Leu Asp Glu Lys Asn Ser Val Ser Val
             20                  25                  30

GAT TTG CCT GGT GAA ATG AAC GTT CTT GTA AGC AAA GAA AAA AAC AAA         262
Asp Leu Pro Gly Glu Met Asn Val Leu Val Ser Lys Glu Lys Asn Lys
         35                  40                  45

GAC GGC AAG TAC GAT CTA ATT GCA ACA GTA GAC AAG CTT GAG CTT AAA         310
Asp Gly Lys Tyr Asp Leu Ile Ala Thr Val Asp Lys Leu Glu Leu Lys
     50                  55                  60

GGA ACT TCT GAT AAA AAC AAT GGA TCT GGA GTA CTT GAA GGC GTA AAA         358
Gly Thr Ser Asp Lys Asn Asn Gly Ser Gly Val Leu Glu Gly Val Lys
 65                  70                  75                  80

GCT GAC AAA AGT AAA GTA AAA TTA ACA ATT TCT GAC GAT CTA GGT CAA         406
Ala Asp Lys Ser Lys Val Lys Leu Thr Ile Ser Asp Asp Leu Gly Gln
                 85                  90                  95

ACC ACA CTT GAA GTT TTC AAA GAA GAT GGC AAA ACA CTA GTA TCA AAA         454
Thr Thr Leu Glu Val Phe Lys Glu Asp Gly Lys Thr Leu Val Ser Lys
            100                 105                 110

AAA GTA ACT TCC AAA GAC AAG TCA TCA ACA GAA GAA AAA TTC AAT GAA         502
Lys Val Thr Ser Lys Asp Lys Ser Ser Thr Glu Glu Lys Phe Asn Glu
        115                 120                 125

AAA GGT GAA GTA TCT GAA AAA ATA ATA ACA AGA GCA GAC GGA ACC AGA         550
Lys Gly Glu Val Ser Glu Lys Ile Ile Thr Arg Ala Asp Gly Thr Arg
    130                 135                 140
```

```
CTT GAA TAC ACA GAA ATT AAA AGC GAT GGA TCT GGA AAA GCT AAA GAG    598
Leu Glu Tyr Thr Glu Ile Lys Ser Asp Gly Ser Gly Lys Ala Lys Glu
145                 150                 155                 160

GTT TTA AAA GGC TAT GTT CTT GAA GGA ACT CTA ACT GCT GAA AAA ACA    646
Val Leu Lys Gly Tyr Val Leu Glu Gly Thr Leu Thr Ala Glu Lys Thr
                165                 170                 175

ACA TTG GTG GTT AAA GAA GGA ACT GTT ACT TTA AGC AAA AAT ATT TCA    694
Thr Leu Val Val Lys Glu Gly Thr Val Thr Leu Ser Lys Asn Ile Ser
            180                 185                 190

AAA TCT GGG GAA GTT TCA GTT GAA CTT AAT GAC ACT GAC AGT AGT GCT    742
Lys Ser Gly Glu Val Ser Val Glu Leu Asn Asp Thr Asp Ser Ser Ala
        195                 200                 205

GCT ACT AAA AAA ACT GCA GCT TGG AAT TCA GGC ACT TCA ACT TTA ACA    790
Ala Thr Lys Lys Thr Ala Ala Trp Asn Ser Gly Thr Ser Thr Leu Thr
210                 215                 220

ATT ACT GTA AAC AGT AAA AAA ACT AAA GAC CTT GTG TTT ACA AAA GAA    838
Ile Thr Val Asn Ser Lys Lys Thr Lys Asp Leu Val Phe Thr Lys Glu
225                 230                 235                 240

AAC ACA ATT ACA GTA CAA CAA TAC GAC TCA AAT GGC ACC AAA TTA GAG    886
Asn Thr Ile Thr Val Gln Gln Tyr Asp Ser Asn Gly Thr Lys Leu Glu
                245                 250                 255

GGG TCA GCA GTT GAA ATT ACA AAA CTT GAT GAA ATT AAA AAC GCT TTA    934
Gly Ser Ala Val Glu Ile Thr Lys Leu Asp Glu Ile Lys Asn Ala Leu
            260                 265                 270

AAA TAA                                                            940
Lys (2) INFORMATION FOR SEQ ID NO: 11:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO: 11:

Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Val Ser Val
                 20                  25                  30

Asp Leu Pro Gly Glu Met Asn Val Leu Val Ser Lys Glu Lys Asn Lys
             35                  40                  45

Asp Gly Lys Tyr Asp Leu Ile Ala Thr Val Asp Lys Leu Glu Leu Lys
         50                  55                  60

Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Asp Leu Gly Gln
                 85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Glu Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
```

```
                        165                 170                 175
Thr Leu Val Val Lys Glu Gly Thr Val Thr Leu Ser Lys Asn Ile Ser
                180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ser Gly Thr Ser Thr Leu Thr
        210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys (2) INFORMATION FOR SEQ ID NO: 12:

(i) SEQUENCE CHARACTERISTICS:
        (A) LENGTH: 940 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Borrelia burgdorferi
        (B) STRAIN: ZS7

(ix) FEATURE:
        (A) NAME/KEY: CDS
        (B) LOCATION: 119..940
        (D) OTHER INFORMATION: /product= "OspA"

(xi) SEQUENCE DESCRIPTION: SEQ ID NO: 12:

AAACCTAATT GAAGTTATTA TCATTTTATT TTTTTTCAAT TTTCTATTTG TTATTTGTTA      60

ATCTTATAAT ATAATTATAC TTGTATTAAG TTATATTAAT ATAAAAGGAG AATATATT      118

ATG AAA AAA TAT TTA TTG GGA ATA GGT CTA ATA TTA GCC TTA ATA GCA      166
Met Lys Lys Tyr Leu Leu Gly Ile Gly Leu Ile Leu Ala Leu Ile Ala
  1               5                  10                  15

TGT AAG CAA AAT GTT AGC AGC CTT GAC GAG AAA AAC AGC GTT TCA GTA      214
Cys Lys Gln Asn Val Ser Ser Leu Asp Glu Lys Asn Ser Val Ser Val
             20                  25                  30

GAT TTG CCT GGT GAA ATG AAC GTT CTT GTA AGC AAA GAA AAA AAC AAA      262
Asp Leu Pro Gly Glu Met Asn Val Leu Val Ser Lys Glu Lys Asn Lys
         35                  40                  45

GAC GGC AAG TAC GAT CTA ATT GCA ACA GTA GAC AAG CTT GAG CTT AAA      310
Asp Gly Lys Tyr Asp Leu Ile Ala Thr Val Asp Lys Leu Glu Leu Lys
     50                  55                  60

GGA ACT TCT GAT AAA AAC AAT GGA TCT GGA GTA CTT GAA GGC GTA AAA      358
Gly Thr Ser Asp Lys Asn Asn Gly Ser Gly Val Leu Glu Gly Val Lys
 65                  70                  75                  80

GCT GAC AAA AGT AAA GTA AAA TTA ACA ATT TCT GAC GAT CTA GGT CAA      406
Ala Asp Lys Ser Lys Val Lys Leu Thr Ile Ser Asp Asp Leu Gly Gln
                 85                  90                  95

ACC ACA CTT GAA GTT TTC AAA GAA GAT GGC AAA ACA CTA GTA TCA AAA      454
Thr Thr Leu Glu Val Phe Lys Glu Asp Gly Lys Thr Leu Val Ser Lys
            100                 105                 110

AAA GTA ACT TCC AAA GAC AAG TCA TCA ACA GAA GAA AAA TTC AAT GAA      502
Lys Val Thr Ser Lys Asp Lys Ser Ser Thr Glu Glu Lys Phe Asn Glu
        115                 120                 125
```

```
AAA GGT GAA GTA TCT GAA AAA ATA ATA ACA AGA GCA GAC GGA ACC AGA      550
Lys Gly Glu Val Ser Glu Lys Ile Ile Thr Arg Ala Asp Gly Thr Arg
    130                 135                 140

CTT GAA TAC ACA GAA ATT AAA AGC GAT GGA TCT GGA AAA GCT AAA GAG      598
Leu Glu Tyr Thr Glu Ile Lys Ser Asp Gly Ser Gly Lys Ala Lys Glu
145                 150                 155                 160

GTT TTA AAA AGC TAT GTT CTT GAA GGA ACT TTA ACT GCT GAA AAA ACA      646
Val Leu Lys Ser Tyr Val Leu Glu Gly Thr Leu Thr Ala Glu Lys Thr
                165                 170                 175

ACA TTG GTG GTT AAA GAA GGA ACT GTT ACT TTA AGC AAA AAT ATT TCA      694
Thr Leu Val Val Lys Glu Gly Thr Val Thr Leu Ser Lys Asn Ile Ser
                180                 185                 190

AAA TCT GGG GAA GTT TCA GTT GAA CTT AAT GAC ACT GAC AGT AGT GCT      742
Lys Ser Gly Glu Val Ser Val Glu Leu Asn Asp Thr Asp Ser Ser Ala
        195                 200                 205

GCT ACT AAA AAA ACT GCA GCT TGG AAT TCA GGC ACT TCA ACT TTA ACA      790
Ala Thr Lys Lys Thr Ala Ala Trp Asn Ser Gly Thr Ser Thr Leu Thr
        210                 215                 220

ATT ACT GTA AAC AGT AAA AAA ACT AAA GAC CTT GTG TTT ACA AAA GAA      838
Ile Thr Val Asn Ser Lys Lys Thr Lys Asp Leu Val Phe Thr Lys Glu
225                 230                 235                 240

AAC ACA ATT ACA GTA CAA CAA TAC GAC TCA AAT GGC ACC AAA TTA GAG      886
Asn Thr Ile Thr Val Gln Gln Tyr Asp Ser Asn Gly Thr Lys Leu Glu
                245                 250                 255

GGG TCA GCA GTT GAA ATT ACA AAA CTT GAT GAA ATT AAA AAC GCT TTA      934
Gly Ser Ala Val Glu Ile Thr Lys Leu Asp Glu Ile Lys Asn Ala Leu
                260                 265                 270

AAA TAA                                                              940
Lys
```

(2) INFORMATION FOR SEQ ID NO: 13:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Asn Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
            85                  90                  95

Thr Thr Leu Glu Val Phe Lys Glu Asp Gly Lys Thr Leu Val Ser Lys
        100                 105                 110

Lys Val Thr Ser Lys Asp Lys Ser Ser Thr Glu Glu Lys Phe Asn Glu
    115                 120                 125

Lys Gly Glu Val Ser Glu Lys Ile Ile Thr Arg Ala Asp Gly Thr Arg
130                 135                 140
```

```
Leu Glu Tyr Thr Glu Ile Lys Ser Asp Gly Ser Gly Lys Ala Lys Glu
145                 150                 155                 160

Val Leu Lys Ser Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys (2) INFORMATION FOR SEQ ID NO: 14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 14:

AATTCGTTAG TATCTAAAGA AAAAACAAA GATGGAAAAT ATGATTGA             48

(2) INFORMATION FOR SEQ ID NO: 15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 15:

AGCTTCAATC ATATTTTCCA TCTTTGTTTT TTTCTTTAGA TACTAACG            48

(2) INFORMATION FOR SEQ ID NO: 16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 16:

GCGAATTCGC GGCCGCTGGC TCTGCAGAGC AATCTG                         36

(2) INFORMATION FOR SEQ ID NO: 17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 17:

GCGGATCCGC TAGCAGAGTA GAACCCAGGA TTAC                           34
```

(2) INFORMATION FOR SEQ ID NO: 18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 18:

| | |
|---|---:|
| GCGAATTCGC TAGCAGGTTG TAAGCAAAAT GTTAGCAG | 38 |

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 19:

| | |
|---|---:|
| TCAAGCTTGT CTACTGTTGC | 20 |

(2) INFORMATION FOR SEQ ID NO: 20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (vi) ORIGINAL SOURCE:
        (A) ORGANISM: pUC19 plasmid from EMBL data base (xi) SEQUENCE DESCRIPTION: SEQ ID NO: 20:

| | |
|---|---:|
| ACGCCAGGGT TTTCCCAG | 18 |

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (vi) ORIGINAL SOURCE:
        (A) ORGANISM: pUC19 plasmid from EMBL data base (xi) SEQUENCE DESCRIPTION: SEQ ID NO: 21:

| | |
|---|---:|
| GTGTGGAATT GTGAGCGG | 18 |

(2) INFORMATION FOR SEQ ID NO: 22:

(i) SEQUENCE CHARACTERISTICS:
        (A) LENGTH: 4 amino acids
        (B) TYPE: amio acid
        (C) STRANDEDNESS: single
        (D) TOPOLOGY: linear (ix) FEATURE:
        (D) OTHER INFORMATION: Xaa = Ile, Ala or Gly (xi) SEQUENCE DESCRIPTION: SEQ ID NO: 22:

Leu Xaa Xaa Cys

What is claimed is:

1. A substantially pure polypeptide encoded by a DNA molecule having a nucleotide sequence as shown in FIG. 3 for ACA1, the polypeptide being substantially free of naturally co-occurring peptides.

2. A substantially pure polypeptide according to claim 1 which is a lipidated polypeptide.

3. A substantially pure polypeptide consisting of an amino acid sequence for ACA1 or Ip90 in FIG. 5.

4. A substantially pure polypeptide according to claim 3, which is the amino acid sequence OspA as shown for ACA1 in FIG. 5 (SEQ. ID. NO. 5).

5. A substantially pure polypeptide according to claim 3, which is the amino acid sequence OspB as shown for ACA1 in FIG. 5 (SEQ. ID. NO. 6).

6. A substantially pure polypeptide according to claim 3, which is the amino acid sequence OspA as shown for Ip90 in FIG. 5 (SEQ. ID. NO. 8).

7. A substantially pure polypeptide according to claim 3, which is the amino acid sequence OspB as shown for Ip90 in FIG. 5 (SEQ. ID. NO. 9).

8. A substantially pure polypeptide according to claim 1 which elicits an immune response against *B. burgdorferi* species I, *B. burgdorferi* species II and *B. burgdorferi* species III.

9. A substantially pure polypeptide according to claim 1 having epitopes detected by the use of antibody-resistant mutation techniques.

10. A substantially pure polypeptide having a sequence selected from the group consisting of the following sequences:

DQDVEDLKKDQKDDSK (SEQ.ID.NO. 9, residues 28–43),

EIFISKEKNEDDK (SEQ.ID.NO. 9, residues 61–73),

KADKSKVTMLVSDD (SEQ.ID.NO. 9, residues 102–115),

KKTAVWNDTSSTL (SEQ.ID.NO. 9, residues 232–244), and

KDLEALKAALK (SEQ.ID.NO. 9, residues 284–294).

11. An immunological composition comprising, as an antigenic component, a polypeptide according to claim 1, and a pharmaceutically acceptable carrier or diluent.

12. An immunological composition according to claim 11 comprising a combination of polypeptides encoded by at least two of the OspA genes derived from B31, ACA1, and Ip90.

13. An immunological composition according to claim 11 comprising a combination of polypeptides encoded by at least two of the OspB genes derived B31, ACA1, and Ip90.

14. An immunological composition comprising a pharmaceutically acceptable carrier or diluent and a combination of at least two polypeptides selected from the group consisting of
(a) a polypeptide encoded by a DNA molecule comprising a nucleotide sequence shown in FIG. 3 for ACA1;
(b) a polypeptide encoded by a DNA molecule comprising a nucleotide sequence as shown in FIG. 3 for Ip90; and
(c) a polypeptide encoded by a DNA fragment of an OspA or OspB gene from *B. burgdorferi*, strain B31.

15. An immunological composition according to claim 11 comprising a polypeptide capable of eliciting an immune response against a *B. burgdorferi* strain selected from the group consisting of strains B31, ACA1, and Ip90.

16. A substantially pure polypeptide comprising KKTKDLVFTKEN (SEQ.ID.NO.2, residues 230–241) wherein said polypeptide is smaller in size than naturally occurring OspA or OspB.

17. An immunological composition comprising a carrier or diluent and a combination of polypeptides comprising:
(a) at least one polypeptide having a sequence selected from the group consisting of:

LVSKEKNKDGKYDL   (SEQ.ID.NO. 2, residues 41–54),

KGTSDKNNGSGV    (SEQ.ID.NO. 2, residues 64–75),

LEGVKADKSKVKL   (SEQ.ID.NO. 2, residues 76–88),

KKVTSKDKSSTEEK  (SEQ.ID.NO. 2, residues 112–125),

KKTKDLVFTKEN    (SEQ.ID.NO. 2, residues 230–241),

QYDSNGTKLEGS    (SEQ.ID.NO. 2, residues 247–258),

AVEITKLDEIKNALK (SEQ.ID.NO. 2, residues 259–273),

DLNLEDSSKKSHQNAK (SEQ.ID.NO. 3, residues 31–46),

KIFVSKEKNSSGK   (SEQ.ID.NO. 3, residues 64–76),

KPDKSKVKLTVSAD  (SEQ.ID.NO. 3, residues 105–118),

KKTGKWEDSTSTL   (SEQ.ID.NO. 3, residues 234–246), and

KNLSELKNALK     (SEQ.ID.NO. 3, residues 286–296), (b) at least one polypeptide having a sequence selected from the group consisting of:

LVSKEKDKDGKYSL  (SEQ.ID.NO. 5, residues 41–54),

KGTSDKTNGSGV    (SEQ.ID.NO. 5, residues 64–75),

LEGTKDDKSKAKL   (SEQ.ID.NO. 5, residues 76–88),

RKVSSKDKTSTDEM  (SEQ.ID.NO. 5, residues 112–125),

KKTTQLVFTKQD    (SEQ.ID.NO. 5, residues 230–241),

KYDSAGTNLEGT    (SEQ.ID.NO. 5, residues 247–258),

AVEIKTLDELKNALK (SEQ.ID.NO. 5, residues 259–273),

DQEIINSDNTPKDSKK (SEQ.ID.NO. 6, residues 33–48),

KIFVSKEKNSAGK   (SEQ.ID.NO. 6, residues 66–78),

KADKTKVAMTIADD  (SEQ.ID.NO. 6, residues 107–120),

KKTATWNETTNTL   (SEQ.ID.NO. 6, residues 237–249), and

KDLAALKAALK     (SEQ.ID.NO. 6, residues 289–299), and, (c) at least one polypeptide having a sequence selected from the group consisting of:

KGTSDKNNGSGT    (SEQ.ID.NO. 8, residues 64–75),

LEGEKTDKSKAKL   (SEQ.ID.NO. 8, residues 76–88),

KKVTLKDKSSTEEK  (SEQ.ID.NO. 8, residues 112–125),

```
                  -continued
RKTKNLVFTKED     (SEQ.ID.NO. 8, residues 231-242), KYDSAGTNLEGK     (SEQ.ID.NO. 8, residues 248-259), AVEITTLKELKDALK  (SEQ.ID.NO. 8, residues 260-274), DQDVEDLKKDQKDDSK (SEQ.ID.NO. 9, residues 28-43), EIFISKEKNEDDK    (SEQ.ID.NO. 9, residues 61-73), KADKSKVTMLVSDD   (SEQ.ID.NO. 9, residues 102-115), KKTAVWNDTSSTL    (SEQ.ID.NO. 9, residues 232-244), and KDLEALKAALK      (SEQ.ID.NO. 9, residues 284-294),
```

18. An immunological composition according to claim 11 wherein the polypeptides are lipidated.

19. An immunological composition according to claim 11, wherein the carrier is a macromolecular carrier.

20. An immunological composition according to claim 19 which additionally comprises an adjuvant.

21. An immunological composition according to claim 20, wherein the adjuvant is selected from the group consisting of Freund's complete, Freund's incomplete adjuvant, aluminum hydroxide, a saponin, a muramyl dipeptide, and an oil.

22. An immunological composition according to claim 19 which additionally comprises a peptide constituting a T-cell epitope.

23. An isolated polypeptide encoded by a DNA molecule comprising a nucleotide sequence of at least 25 nucleotides from ospA from strain B31, as shown in FIG. 3 (SEQ. ID. NO: 1); wherein said nucleotide sequence encodes a lipidation signal sequence.

24. An isolated polypeptide encoded by a DNA molecule comprising a nucleotide sequence of at least 25 coding nucleotides from ospA from strain B31, as shown in FIG. 3 (SEQ. ID. NO: 1).

25. An isolated polypeptide encoded by a DNA molecule having a nucleotide sequence encoding a lipoprotein signal peptide of at least contiguous 10 amino acids within SEQ. ID. NO: 2, and including the sequence L-y-x-C in the C-terminal region of the signal peptide, wherein y and x are independent of each other and each is a neutral amino acid.

26. The polypeptide of claim 25 wherein the signal peptide has at least 13 amino acids.

27. The polypeptide of claim 26 wherein the signal peptide has 16 to 35 amino acids.

28. The polypeptide of claim 27 wherein the signal peptide has 16 to 29 amino acids.

29. The polypeptide of any of claims 25 to 28 wherein x and y are independent of each other and selected from the group consisting of isoleucine, alanine and glycine.

30. An immunological composition comprising, as an antigenic component, a polypeptide according to claim 24, and a pharmaceutically acceptable carrier or diluent.

31. An immunological composition according to claim 30 comprising a combination of polypeptides encoded by at least two of the ospA genes derived from B31, ACA1 and Ip90.

32. An immunological composition according to claim 30 comprising a combination of polypeptides encoded by at least two of the ospB genes derived from B31, ACA1 and Ip90.

33. An immunological composition according to claim 30 comprising a polypeptide capable of eliciting an immune response against a B. burgdorferi strain selected from the group consisting of strains B31, ACA1 and Ip90.

34. An immunological composition according to claim 30 wherein the polypeptide is lipidated.

35. An immunological composition according to claim 30, wherein the carrier is a macromolecular carrier.

36. An immunological composition according to claim 35 which additionally comprises an adjuvant.

37. An immunological composition according to claim 36, wherein the adjuvant is selected from the group consisting of Freund's complete adjuvant, Freund's incomplete adjuvant, aluminum hydroxide, a saponin, a muramyl dipeptide and an oil.

38. An immunological composition according to claim 30 which additionally comprises a peptide constituting a T-cell epitope.

39. An immunological composition comprising, as an antigenic component, a polypeptide according to claim 25, and a pharmaceutically acceptable carrier or diluent.

40. An immunological composition according to claim 39 comprising a combination of polypeptides encoded by at least two of the ospA genes derived from B31, ACA1 and Ip90.

41. An immunological composition according to claim 39 comprising a combination of polypeptides encoded by at least two of the ospB genes derived from B31, ACA1 and Ip90.

42. An immunological composition according to claim 39 comprising a polypeptide capable of eliciting an immune response against a B. burgdorferi strain selected from the group consisting of strains B31, ACA1 and Ip90.

43. A substantially pure polypeptide comprising a sequence selected from the group consisting of the following sequences:

```
LVSKEKNKDGKYDL   (SEQ.ID.NO. 2, residues 41-54), and

KGTSDKNNGSGV     (SEQ.ID.NO. 2, residues 64-75),
``` wherein said polypeptide is capable of eliciting an immune response against B. burgdorferi of any of the strains B31, ACA1 and Ip90 with immunocompetent cells, and is smaller in size than naturally occurring OspA or OspB.

44. An immunological composition which comprises a combination of polypeptides comprising (a) at least one polypeptide comprising a sequence selected from the group consisting of:

```
LVSKEKNKDGKYDL   (SEQ.ID.NO. 2, residues 41-54),

KGTSDKNNGSGV     (SEQ.ID.NO. 2, residues 64-75),

LEGVKADKSKVKL    (SEQ.ID.NO. 2, residues 76-88),

KKVTSKDKSSTEEK   (SEQ.ID.NO. 2, residues 112-125),

KKTKDLVFTKEN     (SEQ.ID.NO. 2, residues 230-241),

QYDSNGTKLEGS     (SEQ.ID.NO. 2, residues 247-258),

AVEITKLDEIKNALK  (SEQ.ID.NO. 2, residues 259-273),

DLNLEDSSKKSHQNAK (SEQ.ID.NO. 3, residues 31-46),

KIFVSKEKNSSGK    (SEQ.ID.NO. 3, residues 64-76),

KPDKSKVKLTVSAD   (SEQ.ID.NO. 3, residues 105-118),
```

```
KKTGKWEDSTSTL     (SEQ.ID.NO. 3, residues 234-246), and

KNLSELKNALK       (SEQ.ID.NO. 3, residues 286-296),
```

(b) at least one polypeptide comprising a sequence selected from the group consisting of:

```
LVSKEKDKDGKYSL    (SEQ.ID.NO. 5, residues 41-54),

KGTSDKTNGSGV      (SEQ.ID.NO. 5, residues 64-75),

LEGTKDDKSKAKL     (SEQ.ID.NO. 5, residues 76-88),

RKVSSKDKTSTDEM    (SEQ.ID.NO. 5, residues 112-125),

KKTTQLVFTKQD      (SEQ.ID.NO. 5, residues 230-241),

KYDSAGTNLEGT      (SEQ.ID.NO. 5, residues 247-258),

AVEIKTLDELKNALK   (SEQ.ID.NO. 5, residues 259-273),

DQEIINSDNTPKDSKK  (SEQ.ID.NO. 6, residues 33-48),

KIFVSKEKNSAGK     (SEQ.ID.NO. 6, residues 66-78),

KADKTKVAMTIADD    (SEQ.ID.NO. 6, residues 107-120),

KKTATWNETTNTL     (SEQ.ID.NO. 6, residues 237-249), and

KDLAALKAALK       (SEQ.ID.NO. 6, residues 289-299),
``` and (c) at least one polypeptide comprising a sequence selected from the group consisting of:

```
KGTSDKNNGSGT      (SEQ.ID.NO. 8, residues 64-75),

LEGEKTDKSKAKL     (SEQ.ID.NO. 8, residues 76-88),

KKVTLKDKSSTEEK    (SEQ.ID.NO. 8, residues 112-125),

RKTKNLVFTKED      (SEQ.ID.NO. 8, residues 231-242),

KYDSAGTNLEGK      (SEQ.ID.NO. 8, residues 248-259),

AVEITTLKELKDALK   (SEQ.ID.NO. 8, residues 260-274),

DQDVEDLKKDQKDDSK  (SEQ.ID.NO. 9, residues 28-43),

EIFISKEKNEDDK     (SEQ.ID.NO. 9, residues 61-73),

KADKSKVTMLVSDD    (SEQ.ID.NO. 9, residues 102-115),

KKTAVWNDTSSTL     (SEQ.ID.NO. 9, residues 232-244), and

KDLEALKAALK       (SEQ.ID.NO. 9, residues 284-294),
``` wherein each of the polypeptides is capable of eliciting an immune response against B. burgdorferi of any of the strains B31, ACA1 and Ip90 with immunocompetent cells and is smaller in size than naturally occurring OspA or OspB.

45. An immunological composition according to claim 39 wherein the polypeptide is lipidated.

46. An immunological composition according to claim 39, wherein the carrier is a macromolecular carrier.

47. An immunological composition according to claim 46 which additionally comprises an adjuvant.

48. An immunological composition according to claim 47, wherein the adjuvant is selected from the group consisting of Freund's complete adjuvant, Freund's incomplete adjuvant, aluminum hydroxide, a saponin, a muramyl dipeptide and an oil.

49. An immunological composition according to claim 39 which additionally comprises a peptide constituting a T-cell epitope.

50. A substantially pure polypeptide encoded by a DNA molecule having a nucleotide sequence as shown in FIG. 3 for Ip90, the polypeptide being substantially free of naturally co-occurring peptides.

51. A substantially pure polypeptide according to claim 50 which is a lipidated polypeptide.

52. A substantially pure polypeptide according to claim 50 which elicits an immune response against B. burgdorferi species I, B. burgdorferi species II and B. burgdorferi species III.

53. A substantially pure polypeptide according to claim 50 having epitopes detected by the use of antibody-resistant mutation techniques.

54. A substantially pure polypeptide encoded by a first isolated DNA molecule which specifically hybridizes under high stringency hybridization conditions comprising hybridization at 67° C. in 2×SSC and final washing at 67° C. in 1×SSC to a second DNA molecule which in turn specifically hybridizes under high stringency hybridization conditions comprising hybridization at 67° C. in 2×SSC and final washing at 67° C. in 1×SSC to a third DNA molecule encoding a polypeptide comprising the amino acid sequence ACA1 or Ip90 in FIG. 5 wherein said polypeptide includes at least an epitope of OspA or OspB and has a length comprising 11, 12, 13, 14, 15, or 16 amino acids.

55. Substantially pure ACA1 or Ip90 OspA or OspB comprising amino acids 17-273 of SEQ ID NO:5, amino acids 17-299 of SEQ ID NO:6, amino acids 17-274 of SEQ ID NO:8, and amino acids 17-294 of SEQ ID NO:9, respectively.

56. A substantially pure polypeptide comprising KKTTQLVFTKQD (SEQ.ID.NO. 5, residues 230-241), wherein said polypeptide is smaller in size than naturally occurring OspA or OspB.

57. Substantially pure ACA1 OspA comprising amino acids 17-273 of SEQ ID NO:5.

58. Substantially pure ACA1 OspB comprising amino acids 17-299 of SEQ ID NO:6.

59. Substantially pure Ip90 OspA comprising amino acids 17-274 of (SEQ. ID. NO. 8).

60. Substantially pure Ip90 OspB comprising amino acids 17-294 of (SEQ. ID. NO. 9).

61. A substantially pure polypeptide comprising an amino acid sequence within each of the amino acid sequences of B31, ACA1 and Ip90 in FIG. 5, wherein said polypeptide is capable of eliciting an immune response against a B. Burgdorferi strain selected from the group consisting of strains B31, ACA1, and Ip90, and said polypeptide has a length comprising 11, 12, 13, 14, 15 or 16 amino acids and is smaller in size than naturally occurring OspA or OspB.

62. A substantially pure polypeptide comprising RKTKNLVFTKED (SEQ.ID.NO. 8, residues 231-242), wherein said polypeptide is smaller in size than naturally occurring OspA or OspB.

63. A substantially pure polypeptide comprising an amino acid sequence which is identical to a region in one of the B. burgdorferi amino acid sequences for B31, ACA1 and Ip90 in FIG. 5 and a region in another of the B. burgdorferi amino acid sequences for B31, ACA1 and Ip90 in FIG. 5, wherein said polypeptide is capable of eliciting an immune response against a B. burgdorferi strain selected from the group consisting of strains B31, ACA1, and Ip90, and said polypeptide has a length comprising 11, 12, 13, 14, 15 or 16 amino acids and is smaller in size than naturally occurring OspA or OspB.

64. A substantially pure polypeptide comprising QYD-SNGTKLEGS (SEQ.ID.NO. 2, residues 247–258), wherein said polypeptide is smaller in size than naturally occurring OspA or OspB.

65. A substantially pure polypeptide having an amino acid sequence which is identical to a region in one of the B. burgdorferi amino acid sequences for B31, ACA1 and Ip90 in FIG. 5 and is identical to a region in another of the B. burgdorferi amino acid sequences for B31, ACA1 and Ip90 in FIG. 5, wherein said polypeptide is capable of eliciting an immune response against a B. burgdorferi strain selected from the group consisting of strains B31, ACA1, and Ip90, and said polypeptide has a length comprising 11, 12, 13, 14, 15 or 16 amino acids and is smaller in size than naturally occurring OspA or OspB.

66. A substantially pure polypeptide comprising a sequence selected from the group consisting of:

```
LVSKEKNKDGKYDL    (SEQ.ID.NO. 2, residues 41–54),
LVSKEKDKDGKYSL    (SEQ.ID.NO. 5, residues 41–54),
KGTSDKNNGSGV      (SEQ.ID.NO. 2, residues 64–75),
KGTSDKTNGSGV      (SEQ.ID.NO. 5, residues 64–75),
KGTSDKNNGSGT      (SEQ.ID.NO. 8, residues 64–75),
LEGVKADKSKVKL     (SEQ.ID.NO. 2, residues 76–88),
LEGTKDDKSKAKL     (SEQ.ID.NO. 5, residues 76–88),
LEGEKTDKSKAKL     (SEQ.ID.NO. 8, residues 76–88),
KKVTSKDKSSTEEK    (SEQ.ID.NO. 2, residues 112–125),
RKVSSKDKTSTDEM    (SEQ.ID.NO. 5, residues 112–125),
KKVTLKDKSSTEEK    (SEQ.ID.NO. 8, residues 112–125),
KKTKDLVFTKEN      (SEQ.ID.NO. 2, residues 230–241),
KKTTQLVFTKQD      (SEQ.ID.NO. 5, residues 230–241),
RKTKNLVFTKED      (SEQ.ID.NO. 8, residues 231–242),
QYDSNGTKLEGS      (SEQ.ID.NO. 2, residues 247–258),
KYDSAGTNLEGT      (SEQ.ID.NO. 5, residues 247–258),
KYDSAGTNLEGK      (SEQ.ID.NO. 8, residues 248–259),
AVEITKLDEIKNALK   (SEQ.ID.NO. 2, residues 259–273),
AVEIKTLDELKNALK   (SEQ.ID.NO. 5, residues 259–273),
AVEITTLKELKDALK   (SEQ.ID.NO. 8, residues 260–274),
DLNLEDSSKKSHQNAK  (SEQ.ID.NO. 3, residues 31–46),
DQEIINSDNTPKDSKK  (SEQ.ID.NO. 6, residues 33–48),
DQDVEDLKKDQKDDSK  (SEQ.ID.NO. 9, residues 28–43),
KIFVSKEKNSSGK     (SEQ.ID.NO. 3, residues 64–76),
KIFVSKEKNSAGK     (SEQ.ID.NO. 6, residues 66–78),
EIFISKEKNEDDK     (SEQ.ID.NO. 9, residues 61–73),
KPDKSKVKLTVSAD    (SEQ.ID.NO. 3, residues 105–118),
KADKTKVAMTIAD     (SEQ.ID.NO. 6, residues 107–120),
KADKSKVTMLVSDD    (SEQ.ID.NO. 9, residues 102–115),
KKTGKWEDSTSTL     (SEQ.ID.NO. 3, residues 234–246),
KKTATWNETTNTL     (SEQ.ID.NO. 6, residues 237–249),
KKTAVWNDTSSTL     (SEQ.ID.NO. 9, residues 232–244),
KNLSELKNALK       (SEQ.ID.NO. 3, residues 286–296),
KDLAALKAALK       (SEQ.ID.NO. 6, residues 289–299),
and
KDLEALKAALK       (SEQ.ID.NO. 9, residues 284–294),
``` wherein the polypeptide elicits an immune response against B. burgdorferi with immunocompetent cells, and is smaller in size than naturally occurring OspA or OspB.

67. A substantially pure polypeptide comprising KYD-SAGTNLEGT (SEQ.ID.NO. 5, residues 247–258), wherein the polypeptide is smaller in size than naturally occurring OspA or OspB.

68. A substantially pure polypeptide having a sequence selected from the group consisting of the following sequences:

```
LVSKEKNKDGKYDL    (SEQ.ID.NO. 2, residues 41–54),
and
KGTSDKNNGSGV      (SEQ.ID.NO. 2, residues 64–75).
```

69. A substantially pure polypeptide comprising a sequence selected from the group consisting of:

```
LVSKEKNKDGKYDL    (SEQ.ID.NO. 2, residues 41–54),
KGTSDKNNGSGV      (SEQ.ID.NO. 2, residues 64–75),
LEGVKADKSKVKL     (SEQ.ID.NO. 2, residues 76–88),
KKVTSKDKSSTEEK    (SEQ.ID.NO. 2, residues 112–125),
KKTKDLVFTKEN      (SEQ.ID.NO. 2, residues 230–241),
QYDSNGTKLEGS      (SEQ.ID.NO. 2, residues 247–258),
AVEITKLDEIKNALK   (SEQ.ID.NO. 2, residues 259–273),
DLNLEDSSKKSHQNAK  (SEQ.ID.NO. 3, residues 31–46),
KIFVSKEKNSSGK     (SEQ.ID.NO. 3, residues 64–76),
KPDKSKVKLTVSAD    (SEQ.ID.NO. 3, residues 105–118),
KKTGKWEDSTSTL     (SEQ.ID.NO. 3, residues 234–246),
and
KNLSELKNALK       (SEQ.ID.NO. 3, residues 286–296)
``` wherein said polypeptide is capable of eliciting an immune response against B. burgdorferi of any of the strains B21, ACA1 and Ip90 with immunocompetent cells, and is smaller in size than naturally occurring OspA or OspB.

70. A substantially pure polypeptide comprising KYD-SAGTNLEGK (SEQ.ID.NO. 8, residues 248–259), wherein said polypeptide is smaller in size than naturally occurring OspA or OspB.

71. A substantially pure polypeptide having a sequence selected from the group consisting of:

```
LVSKEKDKDGKYSL   (SEQ.ID.NO. 5, residues 41–54),
KGTSDKTNGSGV     (SEQ.ID.NO. 5, residues 64–75),
LEGTKDDKSKAKL    (SEQ.ID.NO. 5, residues 76–88),
RKVSSKDKTSTDEM   (SEQ.ID.NO. 5, residues 112–125),
KKTTQLVFTKQD     (SEQ.ID.NO. 5, residues 230–241),
KYDSAGTNLEGT     (SEQ.ID.NO. 5, residues 247–258),
AVEIKTLDELKNALK  (SEQ.ID.NO. 5, residues 259–273),
DQEIINSDNTPKDSKK (SEQ.ID.NO. 6, residues 33–48),
KIFVSKEKNSAGK    (SEQ.ID.NO. 6, residues 66–78),
KADKTKVAMTIADD   (SEQ.ID.NO. 6, residues 107–120),
KKTATWNETTNTL    (SEQ.ID.NO. 6, residues 237–249),
and
KDLAALKAALK      (SEQ.ID.NO. 6, residues 289–299).
```

72. A substantially pure polypeptide comprising a sequence selected from the group consisting of:

```
LVSKEKDKDGKYSL   (SEQ.ID.NO. 5, residues 41–54),
KGTSDKTNGSGV     (SEQ.ID.NO. 5, residues 64–75),
LEGTKDDKSKAKL    (SEQ.ID.NO. 5, residues 76–88),
RKVSSKDKTSTDEM   (SEQ.ID.NO. 5, residues 112–125),
KKTTQLVFTKQD     (SEQ.ID.NO. 5, residues 230–241),
KYDSAGTNLEGT     (SEQ.ID.NO. 5, residues 247–258),
AVEIKTLDELKNALK  (SEQ.ID.NO. 5, residues 259–273),
DQEIINSDNTPKDSKK (SEQ.ID.NO. 6, residues 33–48),
KIFVSKEKNSAGK    (SEQ.ID.NO. 6, residues 66–78),
KADKTKVAMTIADD   (SEQ.ID.NO. 6, residues 107–120),
KKTATWNETTNTL    (SEQ.ID.NO. 6, residues 237–249),
and
KDLAALKAALK      (SEQ.ID.NO. 6, residues 289–299)
``` wherein said polypeptide is capable of eliciting an immune response against B. burgdorferi of any of the strains B31, ACA1 and Ip90 with immunocompetent cells, and is smaller in size than naturally occurring OspA or OspB.

73. A substantially pure polypeptide comprising AVEIKTLDELKNALK (SEQ.ID.NO. 5, residues 259–273), wherein said polypeptide is smaller in size than naturally occurring OspA or OspB.

74. A substantially pure polypeptide having a sequence selected from the group consisting of:

```
KGTSDKNNGSGT     (SEQ.ID.NO. 8, residues 64–75),
LEGEKTDKSKAKL    (SEQ.ID.NO. 8, residues 76–88),
KKVTLKDKSSTEEK   (SEQ.ID.NO. 8, residues 112–125),
RKTKNLVFTKED     (SEQ.ID.NO. 8, residues 231–242),
```

-continued

```
KYDSAGTNLEGK     (SEQ.ID.NO. 8, residues 248–259),
AVEITTLKELKDALK  (SEQ.ID.NO. 8, residues 260–274),
DQDVEDLKKDQKDDSK (SEQ.ID.NO. 9, residues 28–43),
EIFISKEKNEDDK    (SEQ.ID.NO. 9, residues 61–73),
KADKSKVTMLVSDD   (SEQ.ID.NO. 9, residues 102–115),
KKTAVWNDTSSTL    (SEQ.ID.NO. 9, residues 232–244),
and
KDLEALKAALK      (SEQ.ID.NO. 9, residues 284–294).
```

75. A substantially pure polypeptide comprising a sequence selected from the group consisting of:

```
KGTSDKNNGSGT     (SEQ.ID.NO. 8, residues 64–75),
LEGEKTDKSKAKL    (SEQ.ID.NO. 8, residues 76–88),
KKVTLKDKSSTEEK   (SEQ.ID.NO. 8, residues 112–125),
RKTKNLVFTKED     (SEQ.ID.NO. 8, residues 231–242),
KYDSAGTNLEGK     (SEQ.ID.NO. 8, residues 248–259),
AVEITTLKELKDALK  (SEQ.ID.NO. 8, residues 260–274),
DQDVEDLKKDQKDDSK (SEQ.ID.NO. 9, residues 28–43),
EIFISKEKNEDDK    (SEQ.ID.NO. 9, residues 61–73),
KADKSKVTMLVSDD   (SEQ.ID.NO. 9, residues 102–115),
KKTAVWNDTSSTL    (SEQ.ID.NO. 9, residues 232–244),
and
KDLEALKAALK      (SEQ.ID.NO. 9, residues 284–294)
``` wherein said polypeptide is capable of eliciting an immune response against B. burgdorferi of any of the strains B31, ACA1 and Ip90 with immunocompetent cells, and is smaller in size than naturally occurring OspA or OspB.

76. A substantially pure polypeptide comprising AVEITTLKELKDALK (SEQ.ID.NO. 8, residues 260–274), wherein said polypeptide is smaller in size than naturally occurring OspA or OspB.

77. An isolated polypeptide encoded by a DNA molecule comprising a nucleotide sequence of at least 25 coding nucleotides from ospA from strains ACA1 or Ip90, as shown in FIG. 3 (SEQ. ID. NOS: 4 or 7).

78. An isolated polypeptide encoded by a DNA molecule comprising a nucleotide sequence of at least 25 coding nucleotides from OspB from strains ACA1 or Ip90, as shown in FIG. 3 (SEQ ID NOS: 4 or 7).

79. An isolated polypeptide encoded by a DNA molecule having a nucleotide sequence encoding a lipoprotein signal peptide of at least contiguous 10 amino acids within SEQ. ID. NO: 3 and including the sequence L-y-x-C in the C-terminal region of the signal peptide, wherein y and x are independent of each other and each is a neutral amino acid.

80. An isolated polypeptide encoded by a DNA molecule having a nucleotide sequence encoding a lipoprotein signal peptide of at least 10 contiguous amino acids within SEQ. ID. NO: 5 and including the sequence L-y-x-C in the C-terminal region of the signal peptide, wherein y and x are independent of each other and each is a neutral amino acid.

81. An isolated polypeptide encoded by a DNA molecule having a nucleotide sequence encoding a lipoprotein signal peptide of at least 10 contiguous amino acids within SEQ. ID. NO: 6 and including the sequence L-y-x-C in the C-terminal region of the signal peptide, wherein y and x are independent of each other and each is a neutral amino acid.

82. An isolated polypeptide encoded by a DNA molecule having a nucleotide sequence encoding a lipoprotein signal peptide of at least 10 contiguous amino acids within SEQ. ID. NO: 8 and including the sequence L-y-x-C in the C-terminal region of the signal peptide, wherein y and x are independent of each other and each is a neutral amino acid.

83. An isolated polypeptide encoded by a DNA molecule having a nucleotide sequence encoding a lipoprotein signal peptide of at least 10 contiguous amino acids within SEQ. ID. NO: 9 and including the sequence L-y-x-C in the C-terminal region of the signal peptide, wherein y and x are independent of each other and each is a neutral amino acid.

84. Substantially pure Ip90 OspB which binds to an antibody elicited by a polypeptide comprising amino acids 17–294 of (SEQ. ID. NO. 9); wherein the antibody is specific to the polypeptide and does not bind to other cellular proteins.

85. The immunological composition of claim 84 wherein the polypeptide is lipidated.

86. A polypeptide comprising AVEITKLDEIKNALK (SEQ.ID.NO. 2, residues 259–273), wherein said polypeptide is smaller in size than naturally occurring OspA or OspB.

87. A substantially pure polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a sequence selected from the group consisting of:

| | |
|---|---|
| LVSKEKNKDGKYDL | (SEQ.ID.NO. 2, residues 41–54), |
| LVSKEKDKDGKYSL | (SEQ.ID.NO. 5, residues 41–54), |
| KGTSDKNNGSGV | (SEQ.ID.NO. 2, residues 64–75), |
| KGTSDKTNGSGV | (SEQ.ID.NO. 5, residues 64–75), |
| and | |
| KGTSDKNNGSGT | (SEQ.ID.NO. 8, residues 64–75), | or a DNA molecule complementary thereto, wherein said polypeptide elicits an immune response against B. burgdorferi of any of the strains B31, ACA1 and Ip90 with immunocompetent cells wherein the polypeptide is smaller in size than naturally occurring OspA or OspB.

88. An immunological composition comprising a combination of different polypeptides comprising (a) at least one polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a sequence selected from the group consisting of:

| | |
|---|---|
| LVSKEKNKDGKYDL | (SEQ.ID.NO. 2, residues 41–54), |
| KGTSDKNNGSGV | (SEQ.ID.NO. 2, residues 64–75), |
| LEGVKADKSKVKL | (SEQ.ID.NO. 2, residues 76–88), |

-continued

| | |
|---|---|
| KKVTSKDKSSTEEK | (SEQ.ID.NO. 2, residues 112–125), |
| KKTKDLVFTKEN | (SEQ.ID.NO. 2, residues 230–241), |
| QYDSNGTKLEGS | (SEQ.ID.NO. 2, residues 247–258), |
| AVEITKLDEIKNALK | (SEQ.ID.NO. 2, residues 259–273), |
| DLNLEDSSKKSHQNAK | (SEQ.ID.NO. 3, residues 31–46), |
| KIFVSKEKNSSGK | (SEQ.ID.NO. 3, residues 64–76), |
| KPDKSKVKLTVSAD | (SEQ.ID.NO. 3, residues 105–118), |
| KKTGKWEDSTSTL | (SEQ.ID.NO. 3, residues 234–246), |
| and | |
| KNLSELKNALK | (SEQ.ID.NO. 3, residues 286–296), | or a DNA molecule complementary thereto, (b) at least one polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a sequence selected from the group consisting of:

| | |
|---|---|
| LVSKEKDKDGKYSL | (SEQ.ID.NO. 5, residues 41–54), |
| KGTSDKTNGSGV | (SEQ.ID.NO. 5, residues 64–75), |
| LEGTKDDKSKAKL | (SEQ.ID.NO. 5, residues 76–88), |
| RKVSSKDKTSTDEM | (SEQ.ID.NO. 5, residues 112–125), |
| KKTTQLVFTKQD | (SEQ.ID.NO. 5, residues 230–241), |
| KYDSAGTNLEGT | (SEQ.ID.NO. 5, residues 247–258), |
| AVEIKTLDELKNALK | (SEQ.ID.NO. 5, residues 259–273), |
| DQEIINSDNTPKDSKK | (SEQ.ID.NO. 6, residues 33–48), |
| KIFVSKEKNSAGK | (SEQ.ID.NO. 6, residues 66–78), |
| KADKTKVAMTIAD | (SEQ.ID.NO. 6, residues 107–120), |
| KKTATWNETTNTL | (SEQ.ID.NO. 6, residues 237–249), |
| and | |
| KDLAALKAALK | (SEQ.ID.NO. 6, residues 289–299), | or a DNA molecule complementary thereto, and, (c) at least one polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a sequence selected from the group consisting of:

| | |
|---|---|
| KGTSDKNNGSGT | (SEQ.ID.NO. 8, residues 64–75), |
| LEGEKTDKSKAKL | (SEQ.ID.NO. 8, residues 76–88), |
| KKVTLKDKSSTEEK | (SEQ.ID.NO. 8, residues 112–125), |
| RKTKNLVFTKED | (SEQ.ID.NO. 8, residues 231–242), |

```
                 -continued
KYDSAGTNLEGK     (SEQ.ID.NO. 8, residues 248-259), AVEITTLKELKDALK  (SEQ.ID.NO. 8, residues 260-274), DQDVEDLKKDQKDDSK (SEQ.ID.NO. 9, residues 28-43), EIFISKEKNEDDK    (SEQ.ID.NO. 9, residues 61-73), KADKSKVTMLVSDD   (SEQ.ID.NO. 9, residues 102-115), KKTAVWNDTSSTL    (SEQ.ID.NO. 9, residues 232-244), and KDLEALKAALK      (SEQ.ID.NO. 9, residues 284-294),
``` or a DNA molecule complementary thereto, wherein each of said polypeptides is capable of eliciting an immune response against B. burgdorferi of any of the strains B31, ACA1 and Ip90 with immunocompetent cells.

89. A substantially pure polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising the amino acid sequence ACA1 or Ip90 in FIG. 5, or a DNA molecule complementary thereto; wherein said polypeptide is smaller in size than naturally occurring OspA or OspB.

90. A substantially pure polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a region in each of the amino acid sequences for B31, ACA1 and Ip90 in FIG. 5, wherein said polypeptide is capable of eliciting an immune response against a B. Burgdorferi strain selected from the group consisting of strains B31, ACA1, and Ip90 or a DNA molecule complementary thereto; and said polypeptide is smaller in size than naturally occurring OspA or OspB.

91. A substantially pure polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a sequence selected from the group consisting of:

```
LVSKEKNKDGKYDL   (SEQ.ID.NO. 2, residues 41-54),

KGTSDKNNGSGV     (SEQ.ID.NO. 2, residues 64-75),

LEGVKADKSKVKL    (SEQ.ID.NO. 2, residues 76-88),

KKVTSKDKSSTEEK   (SEQ.ID.NO. 2, residues 112-125),

KKTKDLVFTKEN     (SEQ.ID.NO. 2, residues 230-241),

QYDSNGTKLEGS     (SEQ.ID.NO. 2, residues 247-258),

AVEITKLDEIKNALK  (SEQ.ID.NO. 2, residues 259-273),

DLNLEDSSKKSHQNAK (SEQ.ID.NO. 3, residues 31-46),

KIFVSKEKNSSGK    (SEQ.ID.NO. 3, residues 64-76),

KPDKSKVKLTVSAD   (SEQ.ID.NO. 3, residues 105-118),

KKTGKWEDSTSTL    (SEQ.ID.NO. 3, residues 234-246),
```

```
                 -continued
and

KNLSELKNALK      (SEQ.ID.NO. 3, residues 286-296),
``` or a DNA molecule complementary thereto, wherein said polypeptide is capable of eliciting an immune response against B. burgdorferi of any of the strains B31, ACA1 and Ip90 with immunocompetent cells; and, said polypeptide is smaller in size than naturally occurring OspA or OspB.

92. A substantially pure polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a sequence selected from the group consisting of:

```
LVSKEKDKDGKYSL   (SEQ.ID.NO. 5, residues 41-54),

KGTSDKTNGSGV     (SEQ.ID.NO. 5, residues 64-75),

LEGTKDDKSKAKL    (SEQ.ID.NO. 5, residues 76-88),

RKVSSKDKTSTDEM   (SEQ.ID.NO. 5, residues 112-125),

KKTTQLVFTKQD     (SEQ.ID.NO. 5, residues 230-241),

KYDSAGTNLEGT     (SEQ.ID.NO. 5, residues 247-258),

AVEIKTLDELKNALK  (SEQ.ID.NO. 5, residues 259-273),

DQEIINSDNTPKDSKK (SEQ.ID.NO. 6, residues 33-48),

KIFVSKEKNSAGK    (SEQ.ID.NO. 6, residues 66-78),

KADKTKVAMTIADD   (SEQ.ID.NO. 6, residues 107-120),

KKTATWNETTNTL    (SEQ.ID.NO. 6, residues 237-249), and

KDLAALKAALK      (SEQ.ID.NO. 6, residues 289-299),
``` or a DNA molecule complementary thereto, wherein said polypeptide is capable of eliciting an immune response against B. burgdorferi of any of the strains B31, ACA1 and Ip90 with immunocompetent cells; and said polypeptide is smaller in size than naturally occurring OspA or OspB.

93. A substantially pure polypeptide encoded by a first isolated DNA molecule which specifically hybridizes under high stringency hybridization conditions comprising hybridization at 67° C. in 2×SSC and final washing at 67° C. in 1×SSC to a second DNA molecule encoding a polypeptide comprising a sequence selected from the group consisting of:

```
KGTSDKNNGSGT     (SEQ.ID.NO. 8, residues 64-75),

LEGEKTDKSKAKL    (SEQ.ID.NO. 8, residues 76-88),

KKVTLKDKSSTEEK   (SEQ.ID.NO. 8, residues 112-125),

RKTKNLVFTKED     (SEQ.ID.NO. 8, residues 231-242),

KYDSAGTNLEGK     (SEQ.ID.NO. 8, residues 248-259),

AVEITTLKELKDALK  (SEQ.ID.NO. 8, residues 260-274),

DQDVEDLKKDQKDDSK (SEQ.ID.NO. 9, residues 28-43),
```

```
           -continued
EIFISKEKNEDDK    (SEQ.ID.NO. 9, residues 61-73),

KADKSKVTMLVSDD   (SEQ.ID.NO. 9, residues 102-115),

KKTAVWNDTSSTL    (SEQ.ID.NO. 9, residues 232-244), and

KDLEALKAALK      (SEQ.ID.NO. 9, residues 284-294)
``` or a DNA molecule complementary thereto, wherein said polypeptide is capable of eliciting an immune response against B. burgdorferi of any of the strains B31, ACA1 and Ip90 with immunocompetent cells; and said polypeptide is smaller in size than naturally occurring OspA or OspB.

94. An immunological composition comprising, as an antigenic component, a polypeptide according to claim 50, and a pharmaceutically acceptable carrier or diluent.

95. An immunological composition according to claim 94 comprising a combination of polypeptides encoded by at least two of the OspA genes derived from B31, ACA1, and Ip90.

96. An immunological composition according to claim 94 comprising a combination of polypeptides encoded by at least two of the OspB genes derived B31, ACA1, and Ip90.

97. An immunological composition according to claim 94 wherein the polypeptides are lipidated.

98. An immunological composition according to claim 94, wherein the carrier is a macromolecular carrier.

99. An immunological composition according to claim 98 which additionally comprises an adjuvant.

100. An immunological composition according to claim 99, wherein the adjuvant is selected from the group consisting of Freund's complete, Freund's incomplete adjuvant, aluminum hydroxide, a saponin, a muramyl dipeptide, and an oil.

101. An immunological composition according to claim 98 which additionally comprises a peptide constituting a T-cell epitope.

102. A substantially pure polypeptide having a sequence selected from the group consisting of the following sequences:

```
LVSKEKNKDGKYDL   (SEQ.ID.NO. 2, residues 41-54),

KGTSDKNNGSGV     (SEQ.ID.NO. 2, residues 64-75),

LEGVKADKSKVKL    (SEQ.ID.NO. 2, residues 76-88),

KKVTSKDKSSTEEK   (SEQ.ID.NO. 2, residues 112-125),

KKTKDLVFTKEN     (SEQ.ID.NO. 2, residues 230-241),

QYDSNGTKLEGS     (SEQ.ID.NO. 2, residues 247-258), and

AVEITKLDEIKNALK  (SEQ.ID.NO. 2, residues 259-273).
```

103. A substantially pure polypeptide having a sequence selected from the group consisting of the following sequences:

```
LVSKEKDKDGKYSL   (SEQ.ID.NO. 5, residues 41-54),

KGTSDKTNGSGV     (SEQ.ID.NO. 5, residues 64-75),

LEGTKDDKSKAKL    (SEQ.ID.NO. 5, residues 76-88),
```

```
           -continued
RKVSSKDKTSTDEM   (SEQ.ID.NO. 5, residues 112-125),

KKTTQLVFTKQD     (SEQ.ID.NO. 5, residues 230-241),

KYDSAGTNLEGT     (SEQ.ID.NO. 5, residues 247-258), and

AVEIKTLDELKNALK  (SEQ.ID.NO. 5, residues 259-273).
```

104. A substantially pure polypeptide having a sequence selected from the group consisting of the following sequences:

```
KGTSDKNNGSGT     (SEQ.ID.NO. 8, residues 64-75),

LEGEKTDKSKAKL    (SEQ.ID.NO. 8, residues 76-88),

KKVTLKDKSSTEEK   (SEQ.ID.NO. 8, residues 112-125),

RKTKNLVFTKED     (SEQ.ID.NO. 8, residues 231-242),

KYDSAGTNLEGK     (SEQ.ID.NO. 8, residues 248-259), and

AVEITTLKELKDALK  (SEQ.ID.NO. 8, residues 260-274).
```

105. A substantially pure polypeptide having a sequence selected from the group consisting of the following sequences:

```
DLNLEDSSKKSHQNAK (SEQ.ID.NO. 3, residues 31-46),

KIFVSKEKNSSGK    (SEQ.ID.NO. 3, residues 64-76),

KPDKSKVKLTVSAD   (SEQ.ID.NO. 3, residues 105-118),

KKTGKWEDSTSTL    (SEQ.ID.NO. 3, residues 234-246), and

KNLSELKNALK      (SEQ.ID.NO. 3, residues 286-296).
```

106. A substantially pure polypeptide having a sequence selected from the group consisting of the following sequences:

```
DQEIINSDNTPKDSKK (SEQ.ID.NO. 6, residues 33-48),

KIFVSKEKNSAGK    (SEQ.ID.NO. 6, residues 66-78),

KADKTKVAMTIAD    (SEQ.ID.NO. 6, residues 107-120),

KKTATWNETTNTL    (SEQ.ID.NO. 6, residues 237-249), and

KDLAALKAALK      (SEQ.ID.NO. 6, residues 289-299).
```

107. A substantially pure polypeptide having a sequence selected from the group consisting of the following sequences:

```
LVSKEKDKDGKYSL   (SEQ.ID.NO. 5, residues 41-54), and

KGTSDKTNGSGV     (SEQ.ID.NO. 5, residues 64-75),
``` wherein said polypeptide is capable of eliciting an immune response against B. burgdorferi of any of the strains B31, ACA1 and Ip90 with immunocompetent cells, and is smaller in size than naturally occurring OspA or OspB.

108. A substantially pure polypeptide comprising: KGTS-DKNNGSGT (SEQ.ID.NO. 8, residues 64–75), wherein said polypeptide is capable of eliciting an immune response against B. burgdorferi of any of the strains B31, ACA1 and Ip90 with immunocompetent cells, and is smaller in size than naturally occurring OspA or OspB.

109. A substantially pure polypeptide comprising KGTS-DKNNGSGT (SEQ.ID.NO. 8, residues 64–75).

110. A substantially pure polypeptide having a sequence selected from the group consisting of the following sequences:

```
LVSKEKDKDGKYSL   (SEQ.ID.NO. 5, residues 41–54), and

KGTSDKTNGSGV     (SEQ.ID.NO. 5, residues 64–75).
```

111. A substantially pure polypeptide comprising KYD-SAGTNLEGK (SEQ.ID.NO. 8, residues 248–259).

112. A substantially pure polypeptide comprising AVEIK-TLDELKNALK (SEQ.ID.NO. 5, residues 259–273).

113. A substantially pure polypeptide comprising AVEIT-TLKELKDALK (SEQ.ID.NO. 8, residues 260–274).

114. A substantially pure polypeptide comprising KYD-SAGTNLEGT (SEQ.ID.NO. 5, residues 247–258).

115. A substantially pure polypeptide comprising KKT-TQLVFTKQD (SEQ.ID.NO. 5, residues 230–241).

116. A substantially pure polypeptide comprising KKT-KDLVFTKEN (SEQ.ID.NO. 2, residues 230–241).

117. A substantially pure polypeptide comprising RKT-KNLVFTKED (SEQ.ID.NO. 8, residues 231–242).

118. A substantially pure polypeptide comprising QYD-SNGTKLEGS (SEQ.ID.NO. 2, residues 247–258).

119. A polypeptide comprising AVEITKLDEIKNALK (SEQ.ID.NO. 2, residues 259–273).

120. Substantially pure ACA1 or Ip90 OspA or OspB which binds to an antibody elicited by a polypeptide comprising amino acids 17–273 of SEQ ID NO:5, amino acids 17–299 of SEQ ID NO:6, amino acids 17–274 of SEQ ID NO:8, or amino acids 17–294 of SEQ ID NO:9; wherein the antibody is specific to the polypeptide and does not bind to other cellular proteins.

121. Substantially pure ACA1 OspA which binds to an antibody elicited by a polypeptide comprising amino acids 17–273 of SEQ ID NO:5; wherein the antibody is specific to the polypeptide and does not bind to other cellular proteins.

122. Substantially pure ACA1 OspB which binds to an antibody elicited by a polypeptide comprising amino acids 17–299 of SEQ ID NO:6; wherein the antibody is specific to the polypeptide and does not bind to other cellular proteins.

123. Substantially pure Ip90 OspA which binds to an antibody elicited by a polypeptide comprising amino acids 17–274 of (SEQ. ID. NO. 8); wherein the antibody is specific to the polypeptide and does not bind to other cellular proteins.

124. An immunological composition comprising a carrier or diluent and a polypeptide as claimed in any of claim 4, 5, 6, 7, 8, 9, 10, 16, 23, 43, 50, 51, 52, 53, 54, 55, 56, 61, 62, 63, 64, 65, 66, 67, 68, 69, 70, 71, 72, 73, 74, 75, 76, 77, 78, 79, 80, 81, 82, 86, 87, 89, 90, 91, 92, 93, 102, 103, 104, 105, 106, 107, 108, 109, 110, 111, 112, 113, 114, 115, 116, 117, 118, 119, 120, 123, 84, 83.

* * * * *